000000000000000000000000000000000000000000000000000
US007828812B2

(12) United States Patent
Stokes et al.

(10) Patent No.: US 7,828,812 B2
(45) Date of Patent: Nov. 9, 2010

(54) SURGICAL SUTURING APPARATUS WITH NEEDLE RELEASE SYSTEM

(75) Inventors: Michael J. Stokes, Cincinnati, OH (US); Mark S. Zeiner, Mason, OH (US); Frederick E. Shelton, IV, New Vienna, OH (US); Mark S. Ortiz, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 537 days.

(21) Appl. No.: 11/394,125

(22) Filed: Mar. 31, 2006

(65) Prior Publication Data
US 2006/0282090 A1 Dec. 14, 2006

Related U.S. Application Data

(63) Continuation-in-part of application No. 11/150,481, filed on Jun. 13, 2005, now Pat. No. 7,615,060.

(51) Int. Cl.
*A61B 17/04* (2006.01)
(52) U.S. Cl. .................. 606/144; 606/139; 606/145
(58) Field of Classification Search ......... 606/139–148; 227/175.1–182.1
See application file for complete search history.

(56) References Cited

U.S. PATENT DOCUMENTS

| 1,822,330 | A |   | 9/1931  | George     |         |
|-----------|---|---|---------|------------|---------|
| 4,557,265 | A | * | 12/1985 | Andersson  | 606/144 |
| 4,899,746 | A | * | 2/1990  | Brunk      | 606/144 |
| 5,080,663 | A |   | 1/1992  | Mills et al. |       |
| 5,152,769 | A | * | 10/1992 | Baber      | 606/145 |
| 5,306,281 | A | * | 4/1994  | Beurrier   | 606/144 |
| 5,376,101 | A |   | 12/1994 | Green et al. |      |
| 5,437,681 | A |   | 8/1995  | Meade et al. |      |
| 5,462,558 | A |   | 10/1995 | Kolesa et al. |     |
| 5,470,338 | A | * | 11/1995 | Whitfield et al. | 606/144 |
| 5,474,568 | A | * | 12/1995 | Scott      | 606/144 |
| 5,514,159 | A |   | 5/1996  | Matula et al. |     |
| 5,527,321 | A | * | 6/1996  | Hinchliffe | 606/144 |
| 5,540,705 | A |   | 7/1996  | Meade et al. |      |
| 5,571,119 | A |   | 11/1996 | Atala      |         |
| 5,586,986 | A | * | 12/1996 | Hinchliffe | 606/147 |
| 5,709,693 | A | * | 1/1998  | Taylor     | 606/145 |
| 5,713,910 | A |   | 2/1998  | Gordon et al. |     |
| 5,741,277 | A |   | 4/1998  | Gordon et al. |     |
| 5,749,898 | A | * | 5/1998  | Schulze et al. | 606/228 |

(Continued)

FOREIGN PATENT DOCUMENTS

EP          1545336         6/2005

(Continued)

*Primary Examiner*—Darwin P Erezo
(74) *Attorney, Agent, or Firm*—Welsh Flaxman & Gitler LLC

(57) ABSTRACT

A surgical suturing apparatus includes a suture housing, a needle mounted within the suture housing for movement about an arcuate path, and a drive assembly operably associated with the needle for controlling movement of the needle with a suture secured thereto about the arcuate path in a manner facilitating application of the suture to tissue. The suture housing has an open position and a closed position, and the needle can be removed from the suture housing when in the open position.

18 Claims, 36 Drawing Sheets

U.S. PATENT DOCUMENTS

| | | |
|---|---|---|
| 5,766,186 A | 6/1998 | Faraz et al. |
| 5,792,153 A | 8/1998 | Swain et al. |
| 5,814,071 A | 9/1998 | McDevitt et al. |
| 5,860,992 A * | 1/1999 | Daniel et al. ............... 606/145 |
| 6,036,694 A | 3/2000 | Goble et al. |
| 6,168,606 B1 * | 1/2001 | Levin et al. ............... 606/181 |
| 6,238,336 B1 | 5/2001 | Ouchi |
| 6,346,111 B1 | 2/2002 | Gordon et al. |
| 6,352,503 B1 | 3/2002 | Matsui et al. |
| 6,443,962 B1 * | 9/2002 | Gaber .................. 606/144 |
| 6,454,778 B2 | 9/2002 | Kortenbach |
| 6,494,888 B1 | 12/2002 | Laufer et al. |
| 6,506,196 B1 | 1/2003 | Laufer |
| 6,551,329 B1 * | 4/2003 | Kortenbach et al. ......... 606/144 |
| 6,558,400 B2 | 5/2003 | Deem et al. |
| 6,656,194 B1 | 12/2003 | Gannoe et al. |
| 6,663,639 B1 | 12/2003 | Laufer et al. |
| 6,719,763 B2 | 4/2004 | Chung et al. |
| 6,719,764 B1 | 4/2004 | Gellman et al. |
| 6,746,460 B2 | 6/2004 | Gannoe et al. |
| 6,755,843 B2 | 6/2004 | Chung et al. |
| 6,773,440 B2 | 8/2004 | Gannoe et al. |
| 6,835,200 B2 | 12/2004 | Laufer et al. |
| 6,908,427 B2 | 6/2005 | Fleener et al. |
| 6,923,819 B2 | 8/2005 | Meade et al. |
| 6,955,643 B2 * | 10/2005 | Gellman et al. ............ 600/104 |
| 7,004,951 B2 | 2/2006 | Gibbens, III |
| 2002/0107530 A1 | 8/2002 | Sauer et al. |
| 2003/0083674 A1 | 5/2003 | Gibbens, III |
| 2003/0171760 A1 | 9/2003 | Gambale |
| 2003/0181924 A1 | 9/2003 | Yamamoto et al. |
| 2003/0208209 A1 * | 11/2003 | Gambale et al. ............ 606/144 |
| 2003/0233104 A1 | 12/2003 | Gellman et al. |
| 2003/0233108 A1 | 12/2003 | Gellman et al. |
| 2004/0034369 A1 | 2/2004 | Sauer et al. |
| 2004/0044354 A1 | 3/2004 | Gannoe et al. |
| 2004/0059350 A1 | 3/2004 | Gordon et al. |
| 2004/0082963 A1 | 4/2004 | Gannoe et al. |
| 2004/0088008 A1 | 5/2004 | Gannoe et al. |
| 2004/0122473 A1 | 6/2004 | Ewers et al. |
| 2004/0138682 A1 | 7/2004 | Onuki et al. |
| 2004/0147941 A1 | 7/2004 | Takemoto et al. |
| 2004/0147958 A1 | 7/2004 | Lam et al. |
| 2004/0162568 A1 | 8/2004 | Saadat et al. |
| 2004/0194790 A1 | 10/2004 | Laufer et al. |
| 2004/0210243 A1 | 10/2004 | Gannoe et al. |
| 2004/0260344 A1 | 12/2004 | Lyons et al. |
| 2005/0015101 A1 | 1/2005 | Gibbens, III et al. |
| 2005/0055038 A1 * | 3/2005 | Kelleher et al. .............. 606/151 |
| 2005/0070931 A1 | 3/2005 | Li et al. |
| 2005/0075653 A1 | 4/2005 | Saadat et al. |
| 2006/0020167 A1 | 1/2006 | Sitzmann |
| 2006/0069396 A1 * | 3/2006 | Meade et al. ................ 606/144 |

FOREIGN PATENT DOCUMENTS

| | | |
|---|---|---|
| EP | 1569709 | 9/2005 |
| EP | 1582138 | 10/2005 |
| EP | 1584295 | 10/2005 |
| EP | 1586275 | 10/2005 |
| EP | 1639936 | 3/2006 |
| WO | WO97/29694 | 8/1997 |
| WO | WO99/12482 | 3/1999 |
| WO | WO99/47050 | 9/1999 |
| WO | WO00/61012 | 10/2000 |
| WO | WO01/10312 | 2/2001 |
| WO | WO01/66001 | 9/2001 |
| WO | WO02/35980 | 5/2002 |
| WO | WO03/090630 | 11/2003 |
| WO | WO2004/021894 | 3/2004 |

* cited by examiner

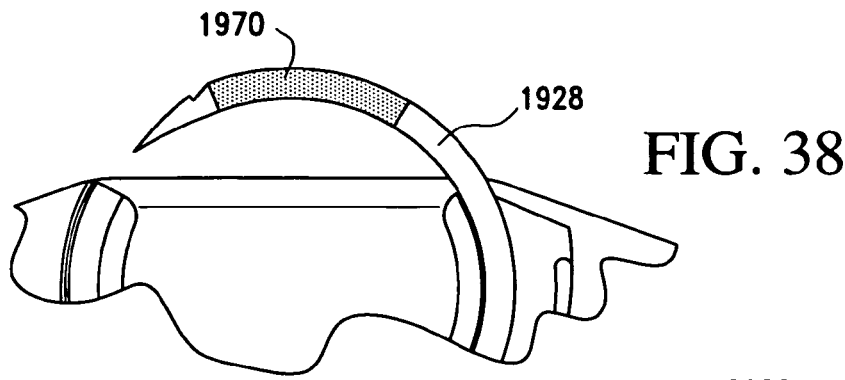
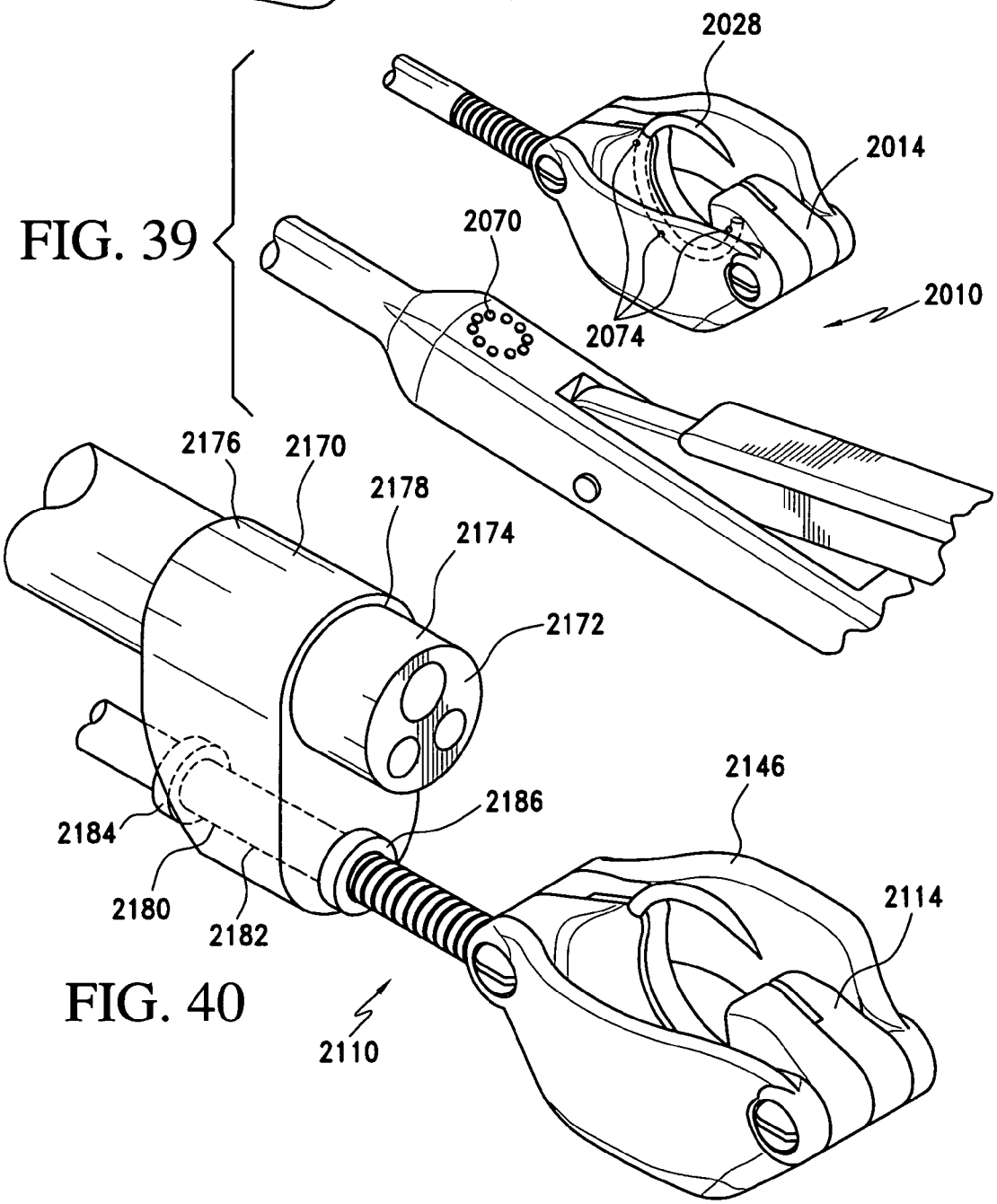
FIG. 38
FIG. 39
FIG. 40

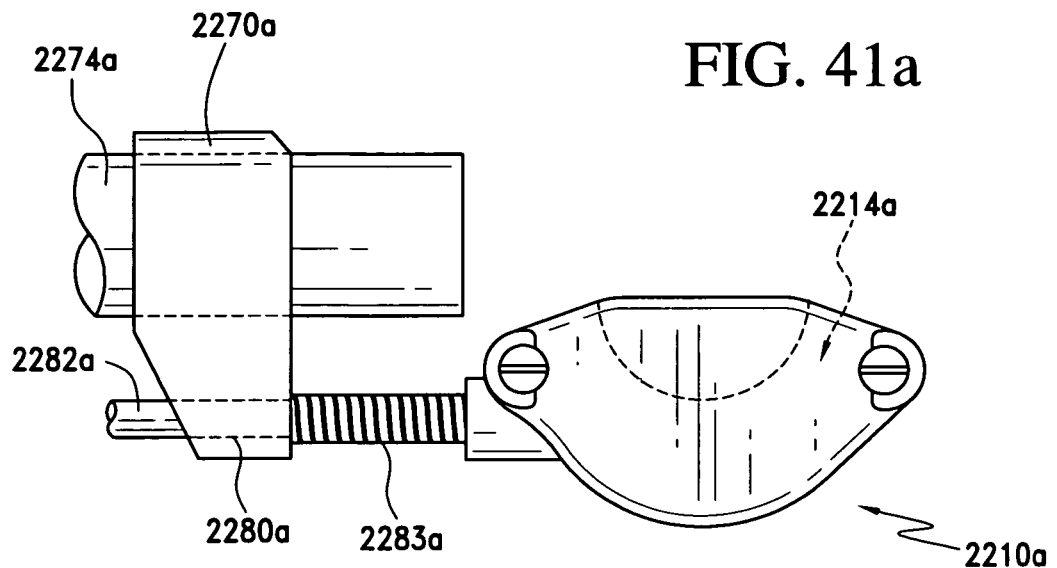
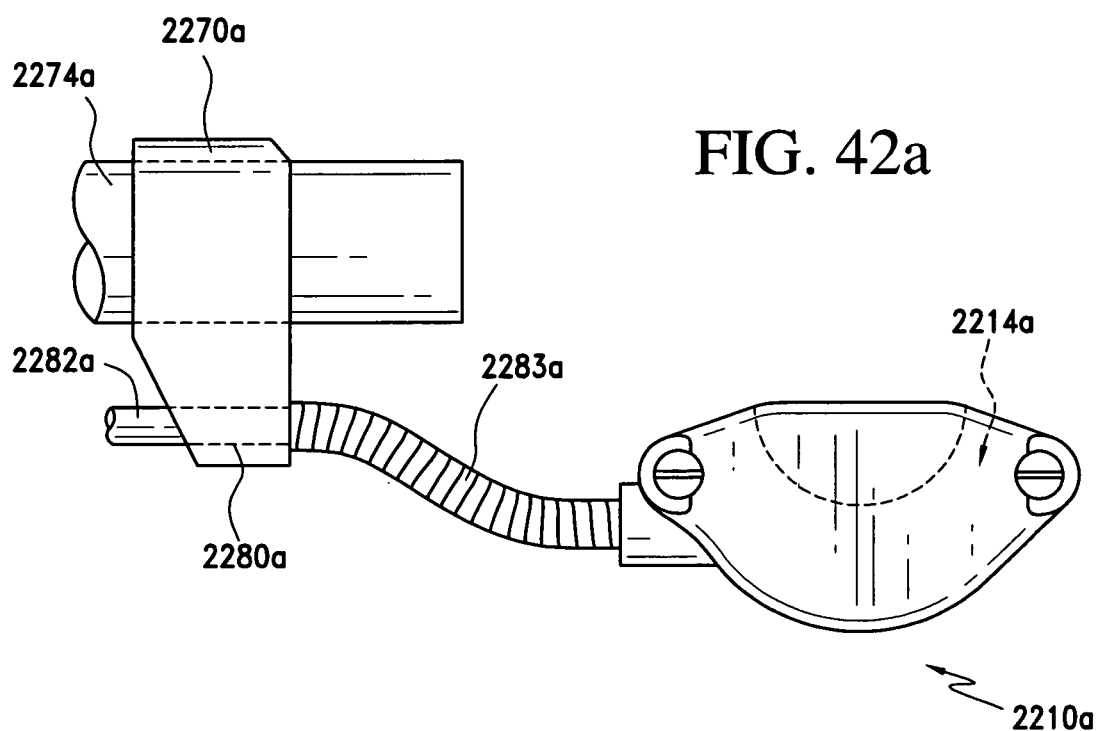

FIG. 44
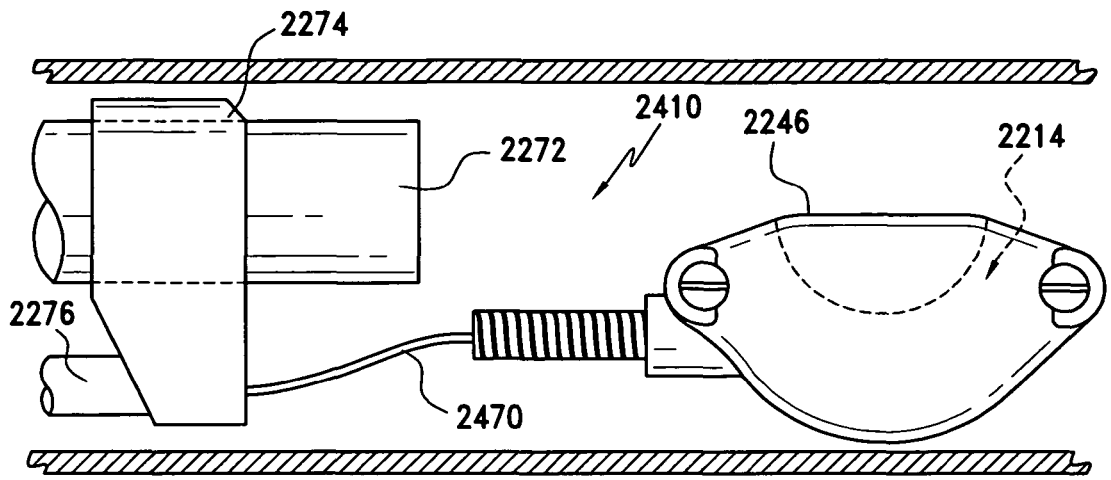
FIG. 45
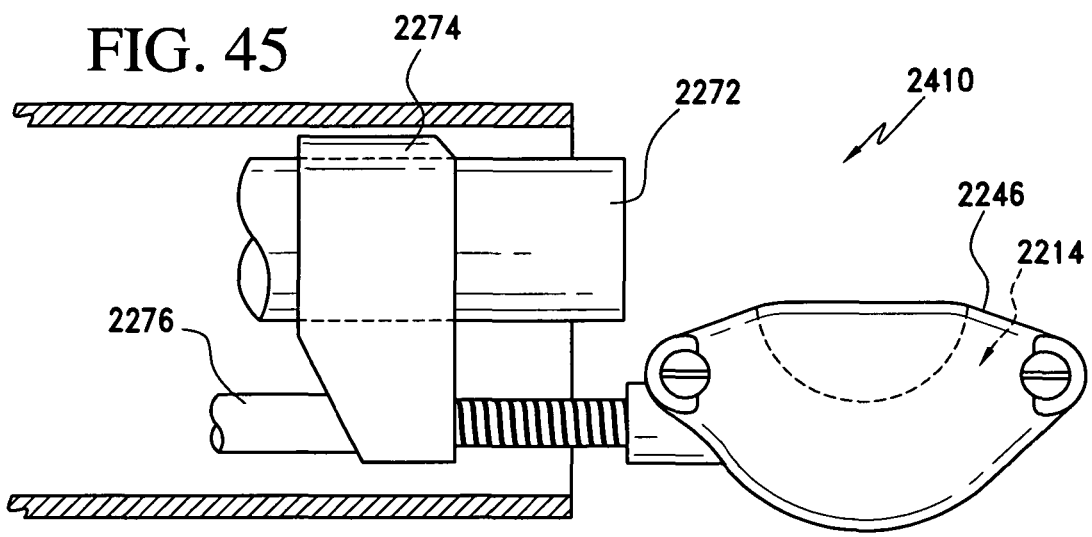
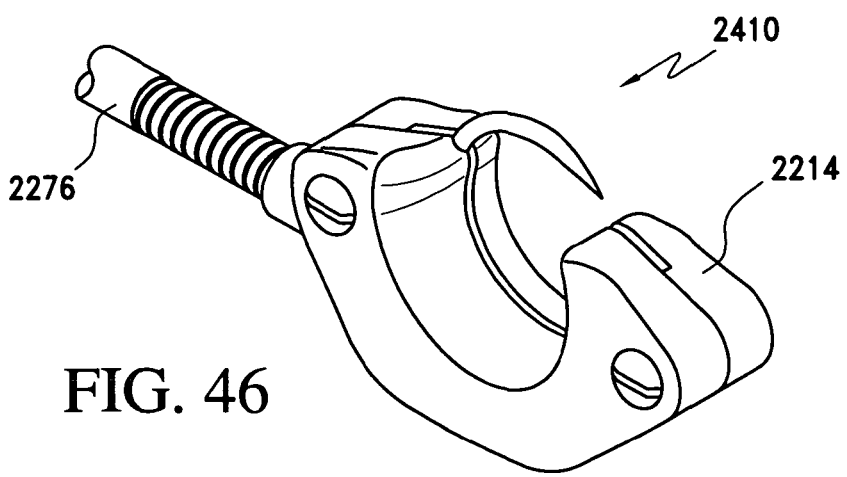
FIG. 46

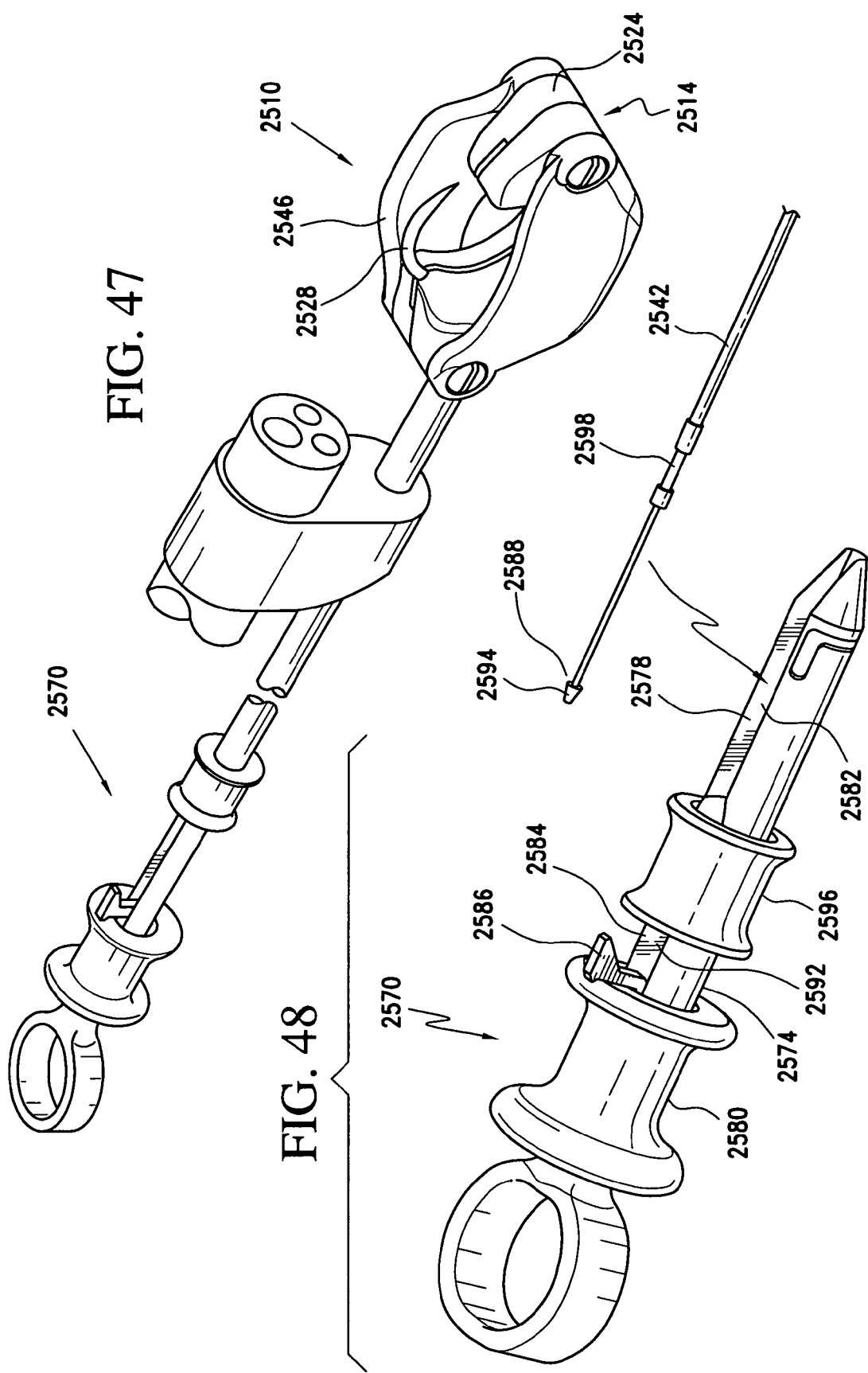

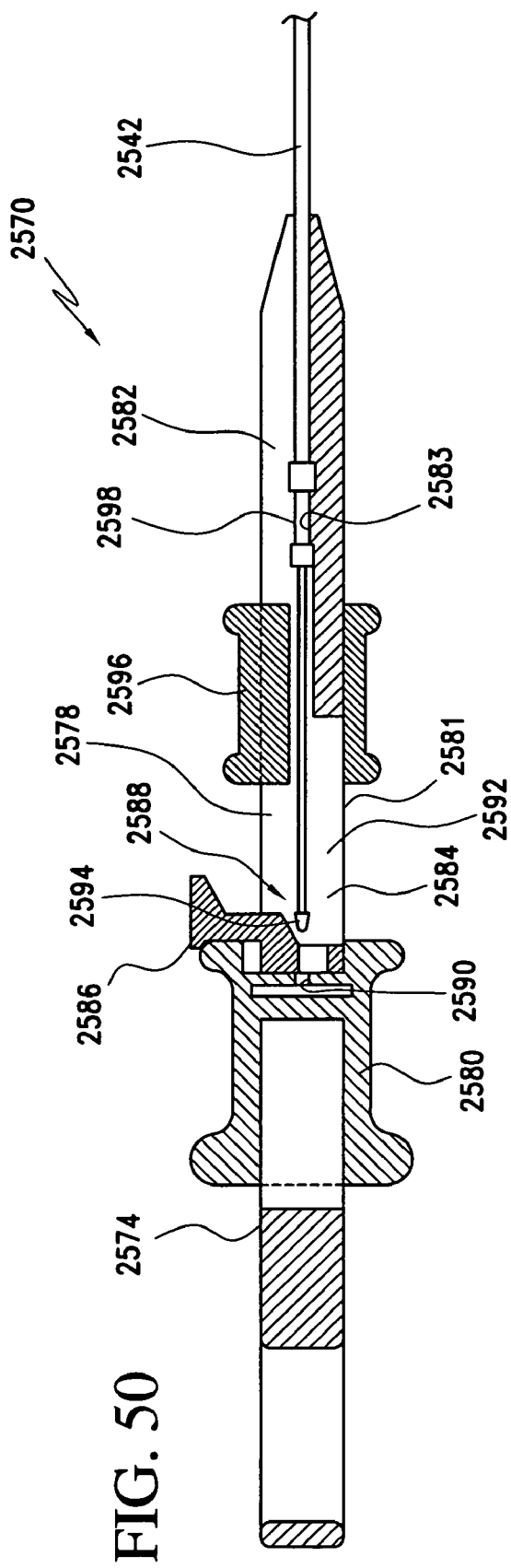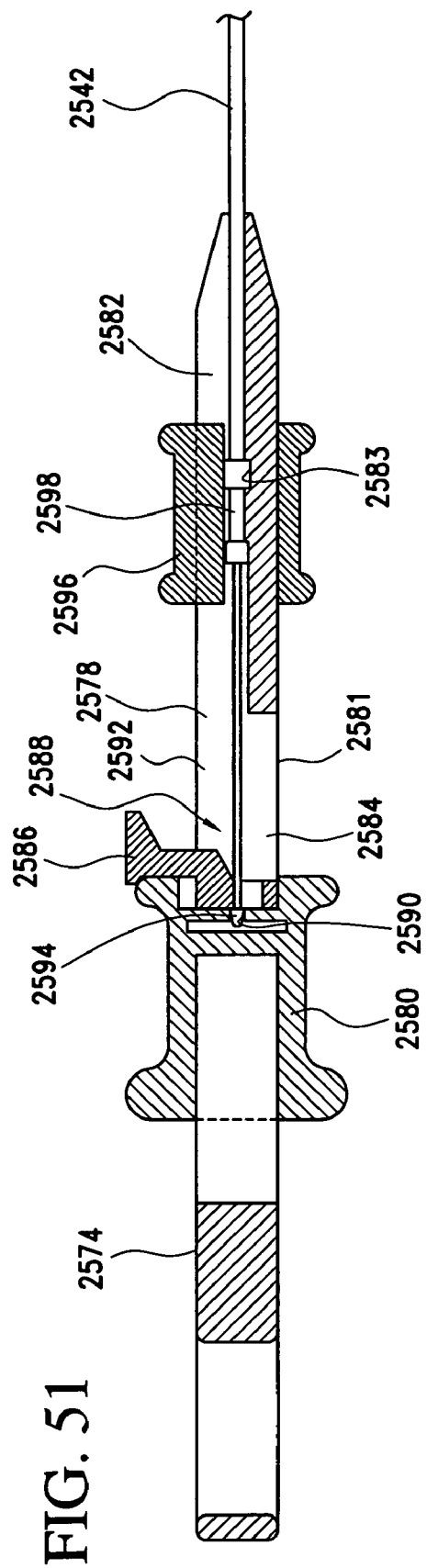
FIG. 50
FIG. 51

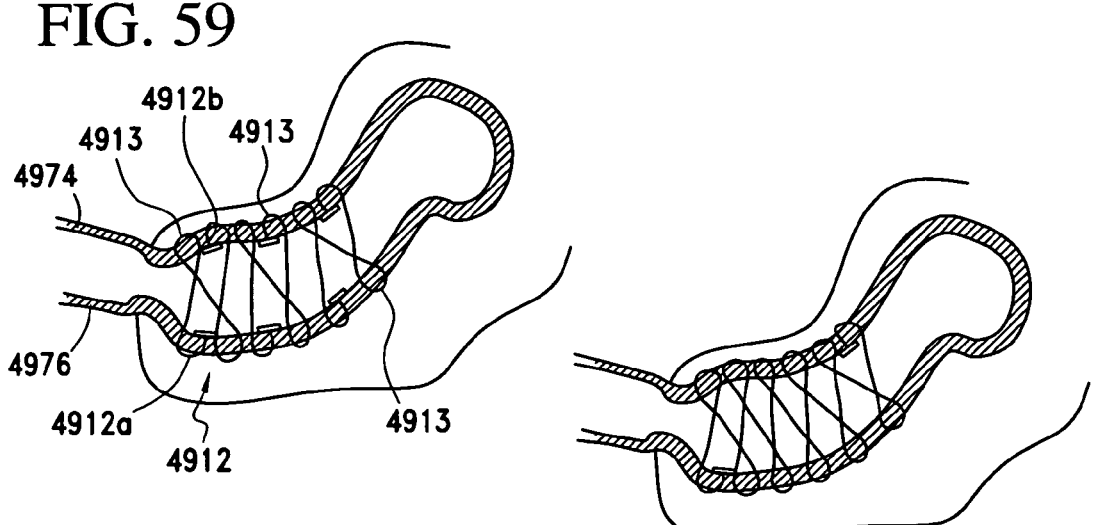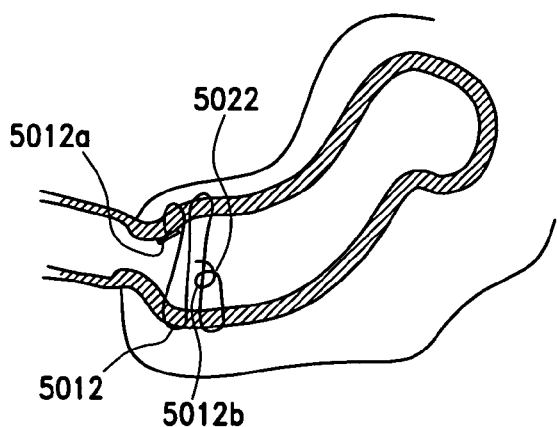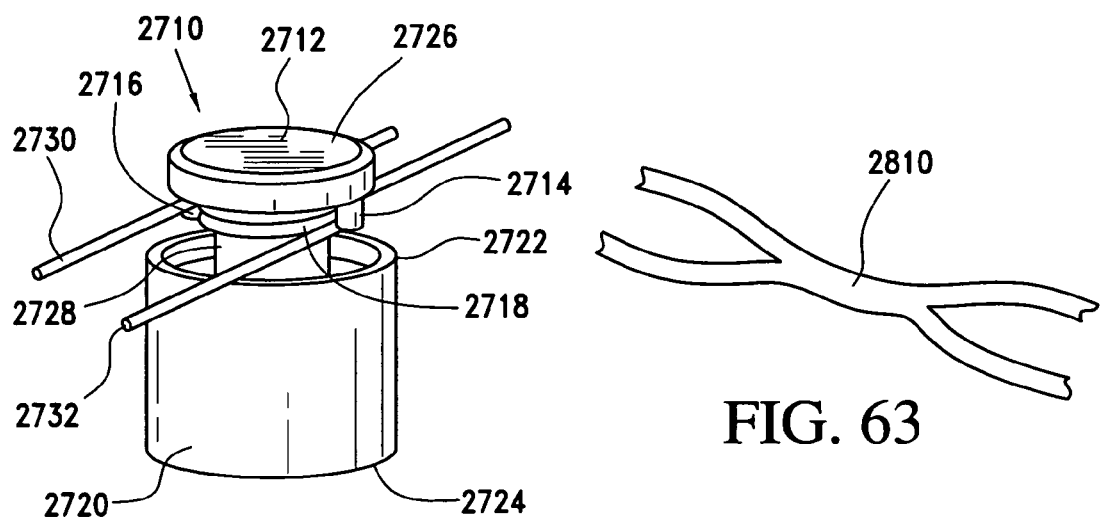

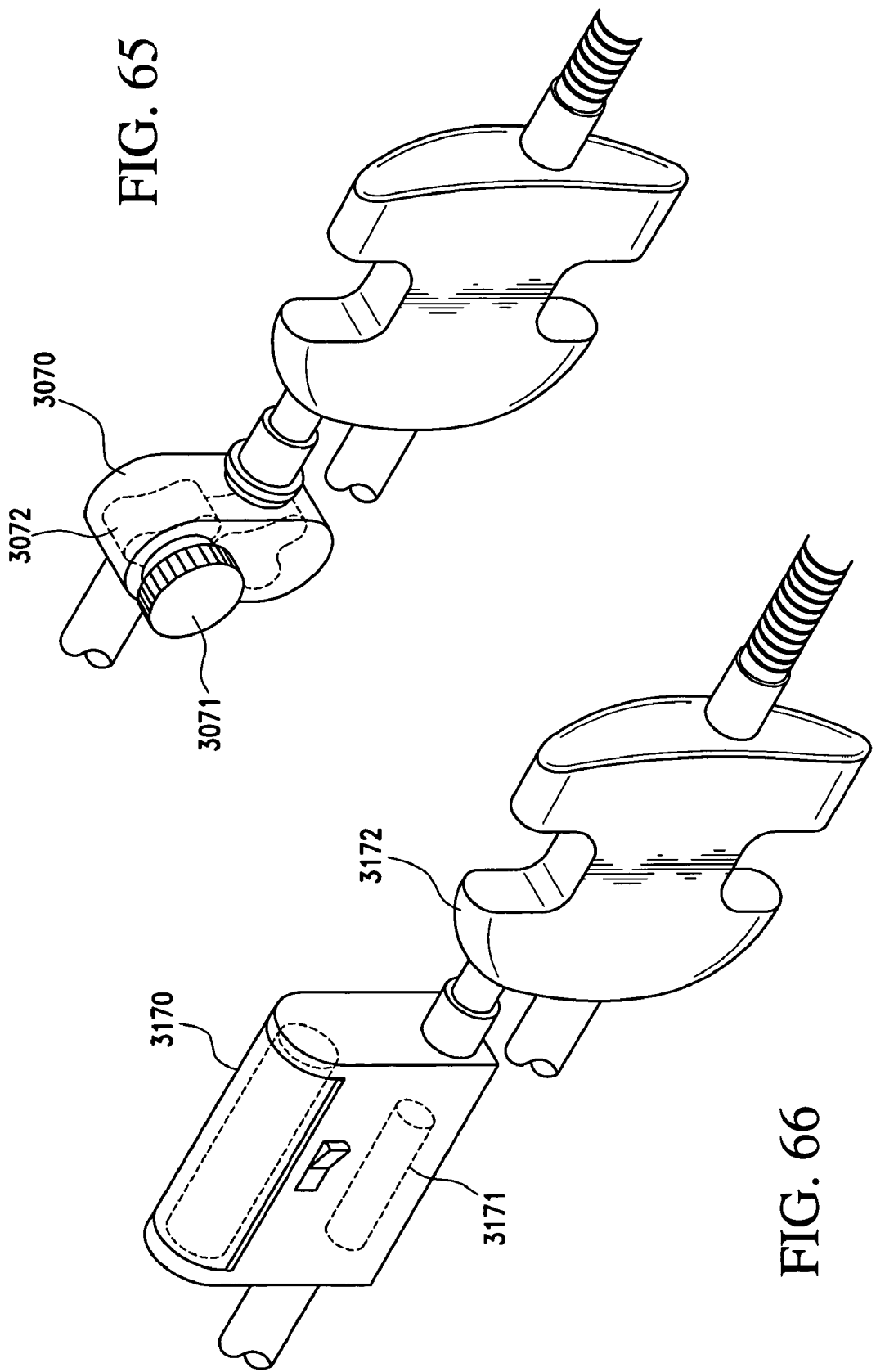

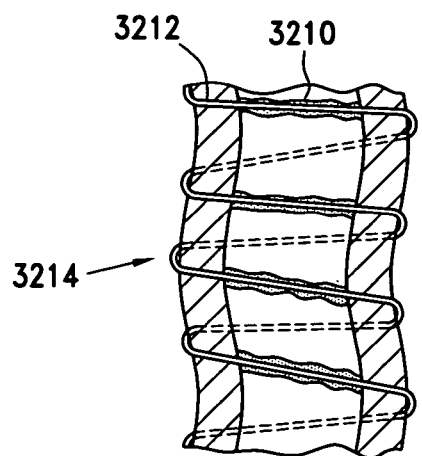
FIG. 69
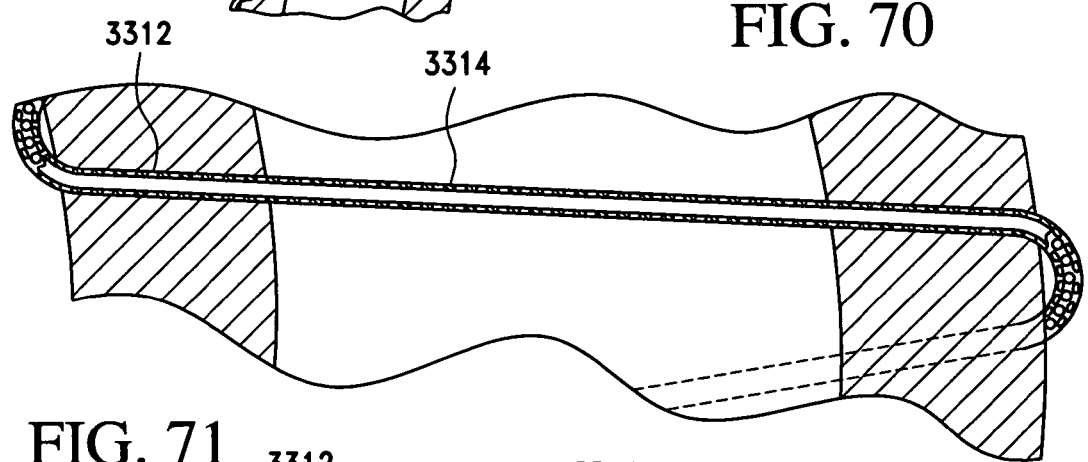
FIG. 70
FIG. 71
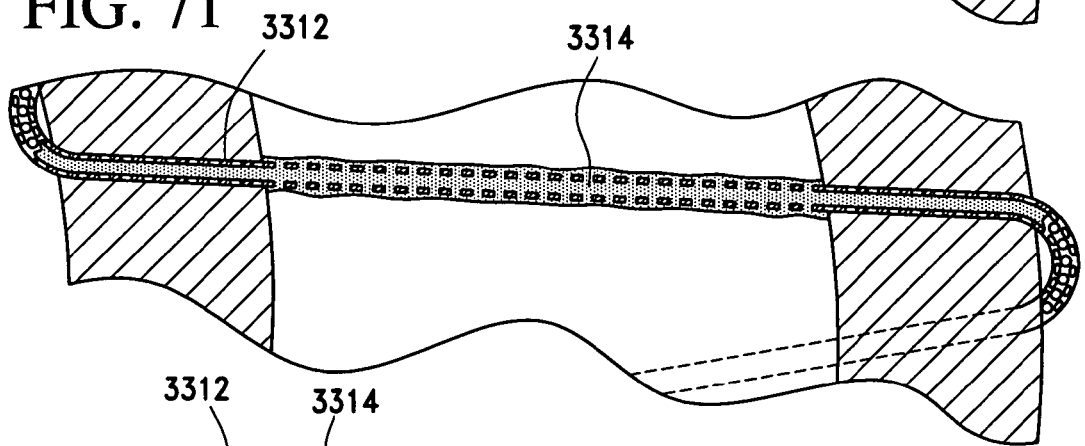
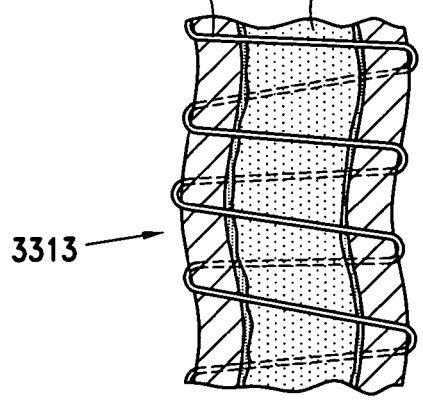
FIG. 72

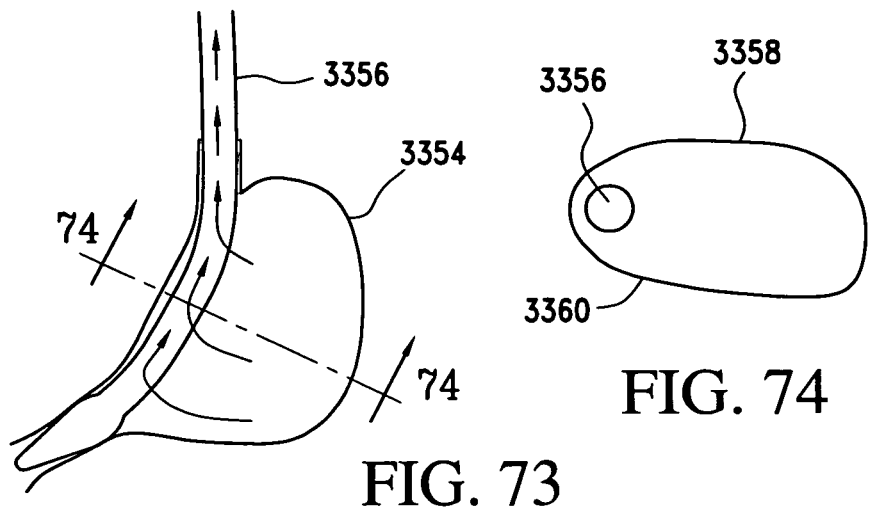
FIG. 73
FIG. 74
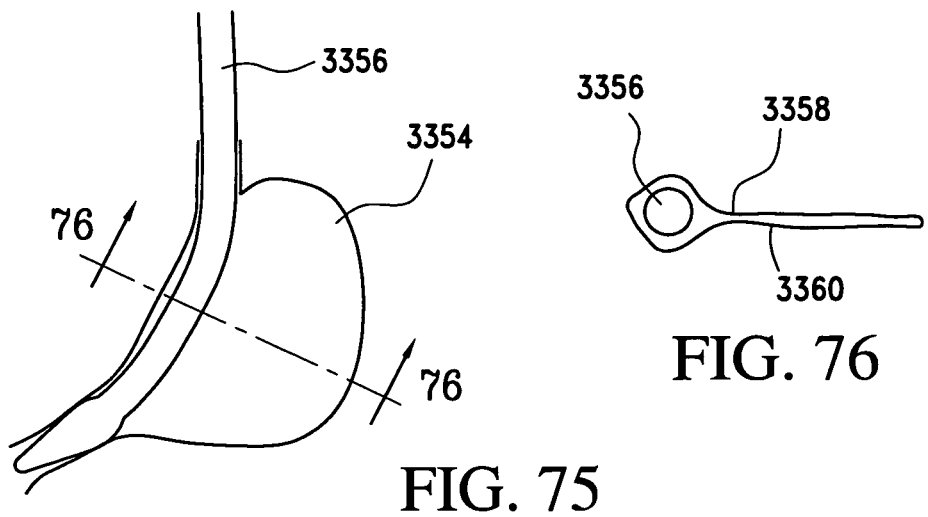
FIG. 75
FIG. 76
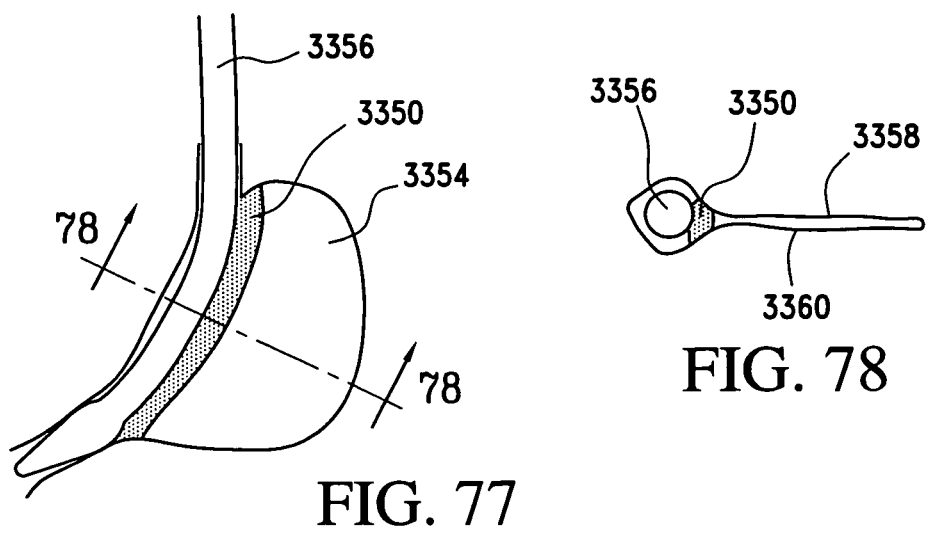
FIG. 77
FIG. 78

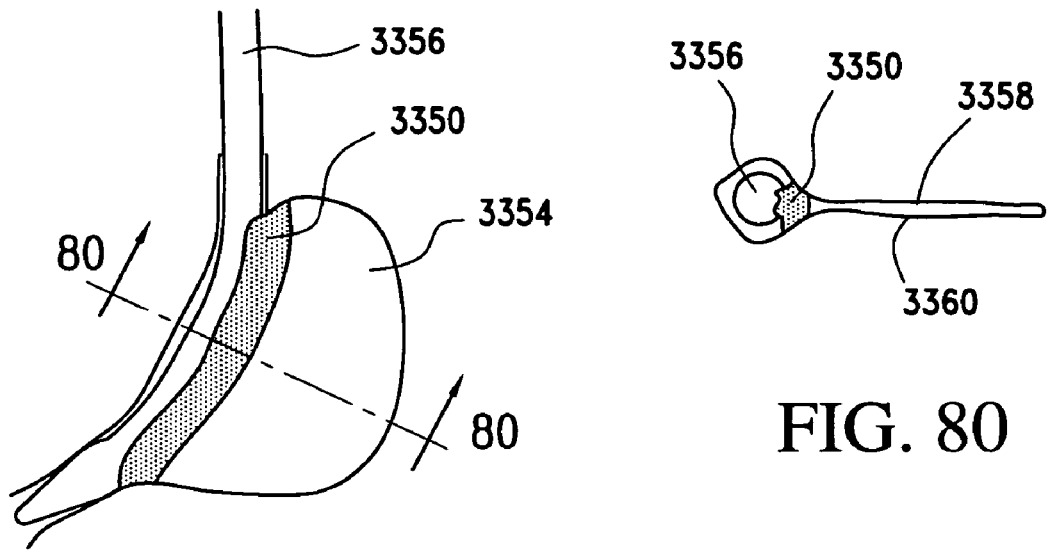
FIG. 79
FIG. 80
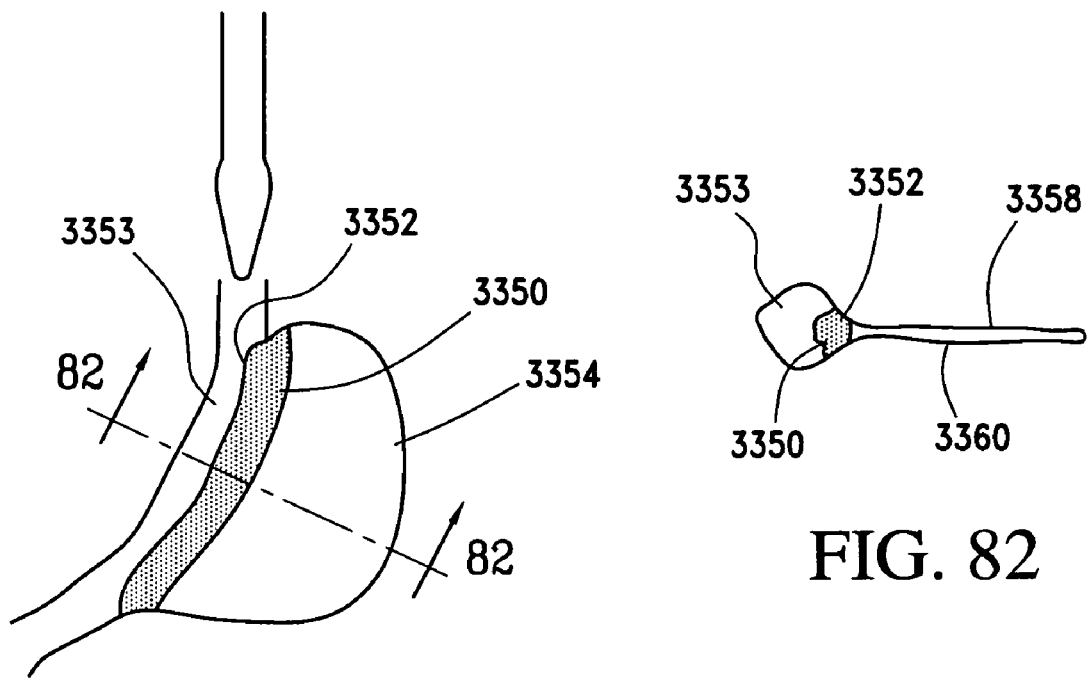
FIG. 81
FIG. 82

SURGICAL SUTURING APPARATUS WITH NEEDLE RELEASE SYSTEM

CROSS REFERENCE TO RELATED APPLICATION

This application is a continuation-in-part of U.S. patent application Ser. No. 11/150,481, entitled "ENDOSCOPIC SUTURING DEVICE", filed Jun. 13, 2005, now U.S. Pat. No. 7,615,060.

BACKGROUND OF THE INVENTION

1. Field of the Invention

The invention relates to a surgical suturing apparatus. More particularly, the invention relates to a surgical suturing apparatus with a needle release system.

2. Description of the Prior Art

Endoscopic procedures have been rapidly developing over the past decade. These procedures often allow for the performance of surgical procedures with minimal trauma when compared to prior techniques requiring a large external opening to expose the internal organ or tissue requiring repair.

In addition to the many areas in which endoscopic procedures have found use, endoscopic procedures have been developed for surgical procedures addressing morbid obesity. Morbid obesity is a serious medical condition. In fact, morbid obesity has become highly pervasive in the United States, as well as other countries, and the trend appears to be heading in a negative direction. Complications associated with morbid obesity include hypertension, diabetes, coronary artery disease, stroke, congestive heart failure, multiple orthopedic problems and pulmonary insufficiency with markedly decreased life expectancy. With this in mind, and as those skilled in the art will certainly appreciate, the monetary and physical costs associated with morbid obesity are substantial. In fact, it is estimated the costs relating to obesity are in excess of 100 billion dollars in the United States alone.

A variety of surgical procedures have been developed to treat obesity. One procedure is Roux-en-Y gastric bypass (RYGB). This operation is highly complex and is commonly utilized to treat people exhibiting morbid obesity. Around 35,000 procedures are performed annually in the United States alone. Other forms of bariatric surgery include Fobi pouch, bilio-pancreatic diversion, and gastroplasty or "stomach stapling". In addition, implantable devices are known which limit the passage of food through the stomach and affect satiety.

RYGB involves movement of the jejunum to a high position using a Roux-en-Y loop. The stomach is completely divided into two unequal portions (a smaller upper portion and a larger lower gastric pouch) using an automatic stapling device. The upper pouch typically measures less than about 1 ounce (or 20 cc), while the larger lower pouch remains generally intact and continues to secret stomach juices flowing through the intestinal track.

A segment of the small intestine is then brought from the lower abdomen and joined with the upper pouch to form an anastomosis created through a half-inch opening, also called the stoma. This segment of the small intestine is called the "Roux loop" Roux limb and carries the food from the upper pouch to the remainder of the intestines, where the food is digested. The remaining lower pouch and the attached segment of duodenum are then reconnected to form another anastomotic connection to the Roux loop limb at a location approximately 50 to 150 cm from the stoma, typically using a stapling instrument. It is at this connection that the digestive juices from the bypass stomach, pancreas, and liver, enter the jejunum and ileum to aide in the digestion of food. Due to the small size of the upper pouch, patients are forced to eat at a slower rate and are satiated much more quickly. This results in a reduction in caloric intake.

As those skilled in the art will certainly appreciate, the conventional RYGB procedure requires a great deal of operative time. Because of the degree of invasiveness, post-operative recovery time can be quite lengthy and painful. In view of the highly invasive nature relating to the current RYGB procedure, other less invasive procedures have been developed. With this mind other procedures for reducing the size of the stomach have been developed. The most common form of gastric reduction surgery involves the application of vertical staples along the stomach to create an appropriate pouch. This procedure is commonly performed laparoscopically and as such requires substantial preoperative, operative, postoperative resources.

As endoscopic devices and procedures have developed, surgeons have begun to employ endoscopic techniques to gastric procedures such as those discussed above in an effort to minimize trauma and reduce the time required for procedures and recovery. With the foregoing in mind, procedures and apparatuses that allow for the performance of gastric reduction surgery in a time efficient and patient friendly manner are needed.

One area that has not been adequately addressed is the need for the application of sutures as these gastric, and other endoscopic, procedures are being performed. The present invention provides an endoscopic suturing device adapted for the continuous application of sutures.

SUMMARY OF THE INVENTION

It is, therefore, an object of the present invention to provide a surgical suturing apparatus. The suturing apparatus includes a suture housing, a needle mounted within the suture housing for movement about an arcuate path, and a drive assembly operably associated with the needle for controlling movement of the needle with a suture secured thereto about the arcuate path in a manner facilitating application of the suture to tissue. The suture housing has an open position and a closed position, and the needle can be removed from the suture housing when in the open position.

It is also an object of the present invention to provide a suturing apparatus wherein the drive assembly moves the needle about a continuous circular path.

It is another object of the present invention to provide a suturing apparatus wherein the suture housing is shaped and dimensioned for insertion through a natural orifice of a patient.

It is a further object of the present invention to provide a suturing apparatus wherein the suture housing is shaped and dimensioned for passage through an orifice from approximately 3 mm to approximately 24 mm in diameter.

It is also another object of the present invention to provide a suturing apparatus wherein the suture housing is shaped and dimensioned for laparoscopic insertion through a trocar.

It is still another object of the present invention to provide a suturing apparatus wherein the suture housing is shaped and dimensioned for passage through an orifice from approximately 3 mm to approximately 18 mm in diameter.

It is yet a further object of the present invention to provide a suturing apparatus wherein the suture housing includes a first housing member and a second housing member, and the first housing member and the second housing member are selectively secured via a cam pin set.

It is also another object of the present invention to provide a suturing apparatus wherein the suture housing includes a first housing member and a second housing member, and the first housing member and the second housing member are selectively secured via a tear strip positioned along a seam of the first housing member and the second housing member.

It is also a further object of the present invention to provide a suturing wherein the suture housing includes a first housing member and a second housing member, and the first housing member and the second housing member are selectively secured via a pull cable laced along the first and second housing members.

It is also an object of the present invention to provide a suturing apparatus wherein the suture housing includes a first housing member and a second housing member, and a hinge connects the first housing member and the second housing member.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 13 and 14 are top views of yet another vacuum chamber secured to the suturing body, wherein FIG. 13 shows the vacuum chamber in its expanded configuration and FIG. 14 shows the vacuum chamber in its low profile configuration.

FIG. 38 is a detailed side, cut away view showing a colored needle utilized in needle position identification.

FIG. 39 is a perspective view showing a visual indicator linked to various sensors for identifying needle position.

FIGS. 40, 41, 41a, 42, 42a and 43 are various views showing an attachment mechanism for securing the present suturing apparatus to an endoscope.

FIGS. 44, 45 and 46 show a guidewire introducer mechanism for use in conjunction with the present suturing apparatus.

FIGS. 47, 48, 49, 50 and 51 disclose a detachable handle mechanism for utilization in conjunction with the present suturing apparatus.

FIGS. 52 through 61 disclose various techniques for suture lacing in accordance with the present invention.

FIG. 62 is a perspective view of a knotting element in accordance with the present invention.

FIG. 63 is a perspective view showing fusing of knotted sutures.

FIGS. 64, 65, 66, 67 and 68 are perspective views showing various suction vacuum assist mechanisms in accordance with the present invention.

FIG. 69 shows a suturing technique utilizing an adhesive/sealant.

FIGS. 70, 71 and 72 show a perforated suture utilized in supplying adhesive/sealant to a suture line.

FIGS. 73 through 82 disclose a procedure whereby a stomach pouch is created through the application of an adhesive/sealant.

DESCRIPTION OF THE PREFERRED EMBODIMENTS

Figure 1:
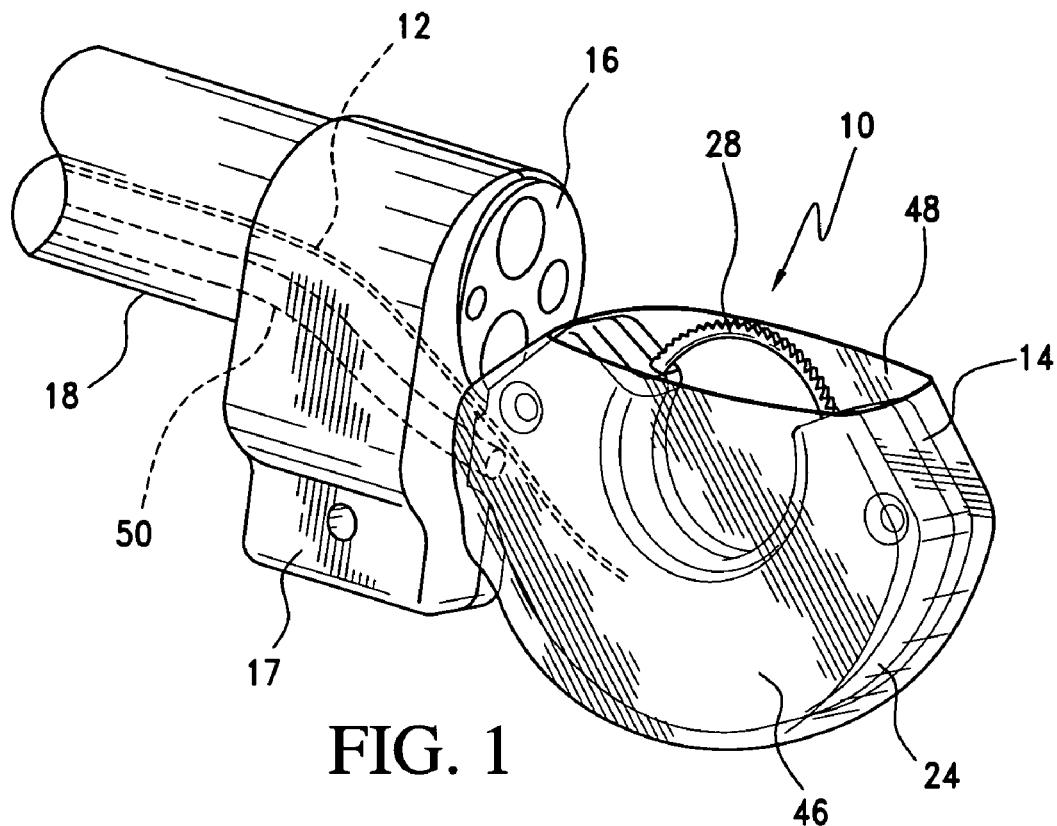
FIG. 1 is a perspective view of the present invention with the vacuum chamber secured thereto.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to FIGS. 1 to 10, an endoscopic suturing apparatus 10 for the continuous application of a suture 12 is disclosed. The term "suture" as used throughout the body of the present application is intended to refer to a variety of flexible securing filaments whether they be made of natural filament, synthetic or polymeric filaments, or metallic wire filaments.

Although the present suturing apparatus is particularly adapted for use in performing endoscopic gastric reduction procedures, those skilled in the art will certainly appreciate the apparatus may be used for a wide variety of applications without departing from the spirit of the present invention. More particularly, the present suturing apparatus is shaped and dimensioned for insertion through a natural orifice of a patient, for example, transorally, and is, therefore, shaped and dimensioned for insertion through an orifice from approximately 3 mm to approximately 24 mm in diameter. Although the present suturing apparatus is particularly adapted for insertion through a patient's natural orifice, the present suturing apparatus may be shaped and dimensioned for laparoscopic insertion through a trocar, and is, therefore, shaped and dimensioned for insertion through an orifice from approximately 3 mm to approximately 18 mm in diameter.

The suturing apparatus 10 includes a suturing body 14 shaped and dimensioned for attachment to the distal end 16 of a commercially available endoscope, or other supporting structure, 18 in a manner permitting actuation thereof and the creation of a vacuum. With this in mind, the suturing body 14 is secured to the endoscope 18 using known attachment structures appreciated by those skilled in the art.

The suturing body 14 is composed of a first housing member 20 and a second housing member 22 secured together to create a suture housing 24 in which the functional components of the present apparatus 10 are housed for movement in accordance with the present invention. The suture housing 24 includes an inner first track 26 in which a needle 28 is positioned for movement about a predetermined continuous circular path under the control of a drive assembly 30.

Although the present suturing apparatus is disclosed in accordance with a preferred embodiment as providing for the translation of the needle about a continuous circular path, it is contemplated many of the concepts underlying the present invention may be applied in systems wherein the needle is merely moved along an arcuate path, and not necessarily along a continuous circular path.

The drive assembly 30 is supported within second and third tracks 32, 34 positioned about the inner first track 26. The drive assembly 30 applies axial motion to cause movement of the needle 28 about its continuous circular path. The drive assembly 30 is generally composed of a friction plate 36 statically mounted along the second track 32 and a friction camming member 38 that moves along the second track 32 while a pin 40 moves along the outer third track 34. A drive cable 42 is coupled to the pin 40 for controlling actuation thereof in the manner described below in greater detail. The drive cable 42 is actuated for movement of the drive assembly 30 by a handle (for example, as shown in FIGS. 47 to 51). Although a preferred handle is disclosed below, it is contemplated a variety of handle structures may be utilized in the actuation of the drive cable without departing from the spirit of the present invention.

For reasons that will become apparent based upon the operation of the present suture apparatus 10 as described below in greater detail, the suturing body 14 is substantially C-shaped with a central opening 44 in which tissue is positioned during suturing. The C-shape of the suturing body 14 allows the needle 28 to move about a circular path during operation thereof and pass through tissue positioned with the central opening.

Figure 2:
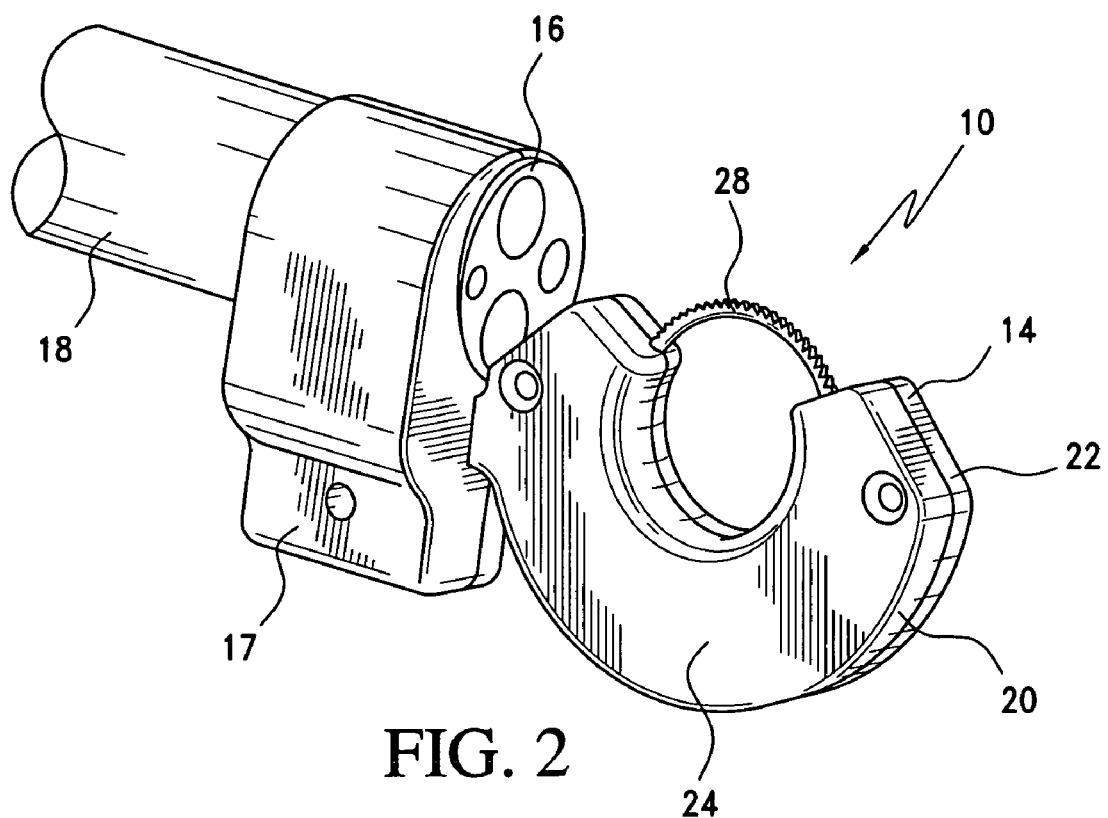
FIG. 2 is a perspective view of the present invention without the vacuum chamber.
Figure 3:
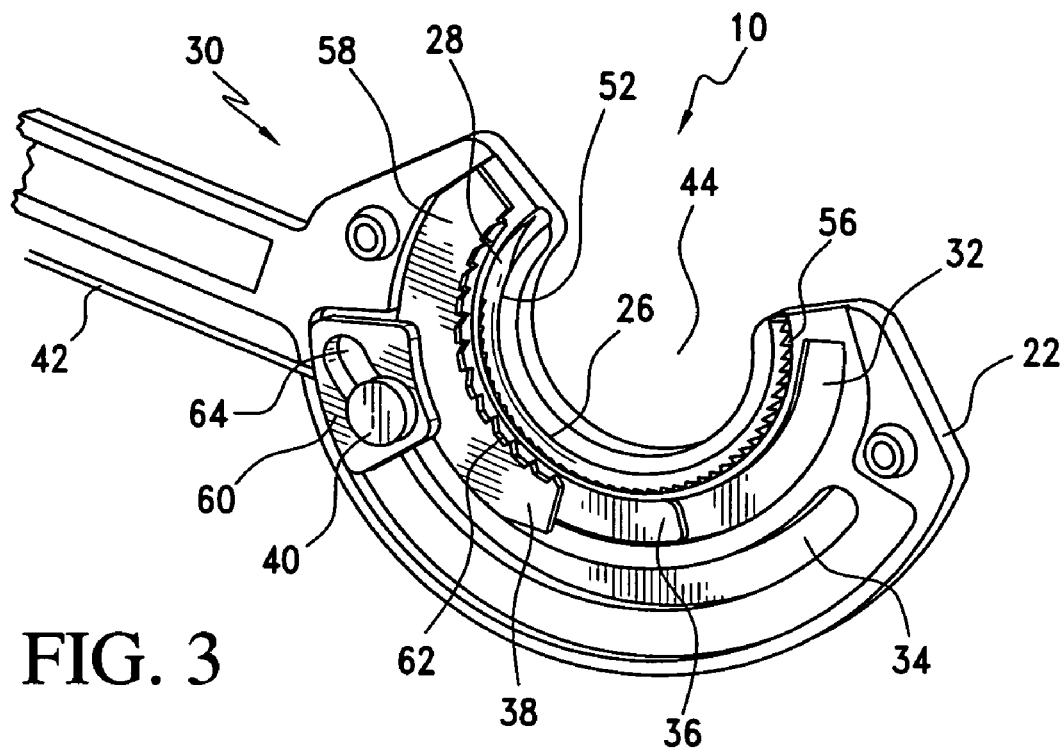
FIGS. 3 through 10 are cut away views demonstrating operation of the present invention.

Referring to FIGS. 1 and 2, and in accordance with a preferred embodiment, the present endoscopic suturing apparatus 10 is attached to a commercially available endoscope 18 by way of a clamp 17. As briefly mentioned above, and as discussed below in greater detail, the suturing apparatus 10 may be secured to the endoscope 18 in a variety of ways without departing from the spirit of the present invention. The suturing apparatus 10 is oriented in a way that allows the user to maintain visibility of the needle 28 and operative field, as well as create a small cross section to aid in transoral insertion (when the suturing apparatus 10 is used in gastric surgical procedures).

A vacuum chamber 46 surrounds and/or otherwise contains the suturing body 14 of the present suture apparatus 10. This defines a cavity 48 in which the suturing body 14 sits. The vacuum chamber 46 is coupled to the vacuum line 50, which is coupled in tandem to the endoscope 18, but not in the working channel of the endoscope 18, such that a vacuum is created within the cavity 48 defined by the vacuum chamber 46, as well as the central opening 44 of the suturing body 14. In this way, the application of the vacuum draws adjacent tissue into the central opening 44 of the suturing body 14.

As briefly mentioned above, the present suturing apparatus 10 is provided with a vacuum chamber 46 designed to enhance one's ability to draw tissue into a position for suturing. The vacuum chamber 46 is shaped and dimensioned to facilitate pulling the tissue wall into the vacuum chamber 46, and particularly, the central opening 44 of the suturing body 14, under the control of the applied vacuum. Once drawn within the vacuum chamber 46 and the central opening 44, the tissue is held therein as the needle 28 is passed therethrough while the suturing body 14 throws stitches. The required vacuum chamber 46 size is based upon the thickness of the tissue being sutured. The vacuum necessary to pull the desired tissue thickness is proportionate to both the thickness of the tissue and the size of the vacuum chamber 46.

As a result, the present vacuum chamber 46 attempts to increase the size thereof to minimize the required vacuum for accomplishing the task, without making the vacuum chamber 46 too large for passage into the stomach. The ability of the present vacuum chamber 46 to achieve desired suction with vacuum pressure provided at a hospital or other medical facility is especially important considering the magnitude of vacuum sources available at different hospitals, as well as within different surgical suites, varies greatly.

Figure 11:
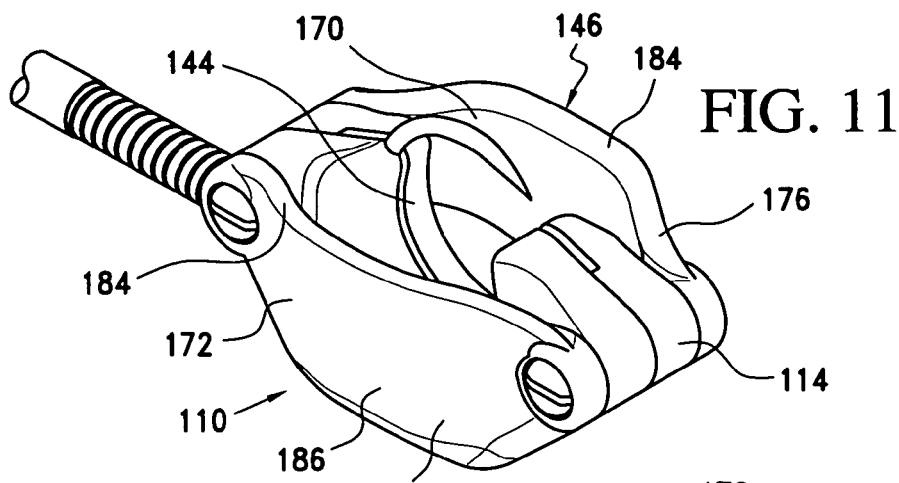
FIG. 11 is a perspective view showing a suturing body with a vacuum chamber in accordance with a preferred embodiment secured thereto.
Figure 12:
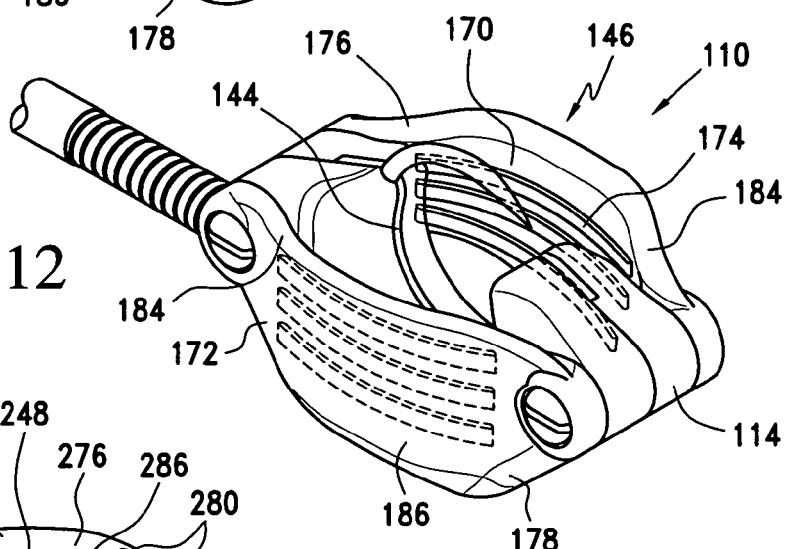
FIG. 12 shows an alternate vacuum chamber secured to the suturing body.

With this in mind, and in accordance with preferred embodiments of the present invention as shown in FIGS. 11 and 12, (where similar reference numerals are used for similar parts) the vacuum chamber 146 is constructed from a resilient elastomer. It is cup-like in its configuration and generally includes an inner wall 170 and an outer wall 172. The inner wall 170 of the vacuum chamber 146 is preferably provided with projections, for example, ribs and/or hooks, 174 (as shown in FIG. 12) to further improve the ability of the vacuum chamber 146 to retain tissue drawn thereon under suction. These projections 174 provide grabbing surfaces for the tissue to be pinned against when the vacuum is applied to the vacuum chamber 146. The projections 174 also increase the holding power of the vacuum thereby minimizing the amount of vacuum needed.

In accordance with a preferred embodiment, the vacuum chamber 146 is composed of first and second vacuum chamber members 176, 178 secured to opposite sides of the suturing body 114 in a manner containing, or otherwise surrounding, the functional components of the suturing body 114. The first and second chamber members 176, 178 are mirror images of each other and define a space surrounding the suturing body 114 for the creation of a vacuum. In accordance with a preferred embodiment, the first and second vacuum chamber members 176, 178 define a cup-like space in which the suturing body 114 is positioned.

Each of the first and second vacuum chamber members 176, 178 includes a semicircular upper edge 184 and a concave lower portion 186. As such, when the first and second vacuum chamber members 176, 178 are secured along opposite sides of the suturing body 114, the cup-like space is defined about the suturing body 114. The cup-like space provides a confined space in which the suction provided by the vacuum is constrained so as to securely and efficiently draw tissue into the central opening 144 of the suturing body 114.

The first and second vacuum chamber members 176, 178 of the vacuum chamber 146 are manufactured from an elastomer, for example, urethane, adiprene or santoprene. The vacuum chamber 146 is designed to permit expansion and contraction thereof. The provision of an expandable vacuum chamber 146 maximizes chamber size to increase tissue inclusion during vacuum application, while permitting reduced vacuum chamber 146 size during insertion of the suturing apparatus 110. More particularly, the ability of the vacuum chamber 146 to expand and contract facilitates trans-oral passage of the suturing apparatus 110 while similarly optimizing vacuum chamber 146 size during tissue suction.

As those skilled in the art will appreciate, the need for trans-oral passage of the suturing apparatus 110 defines an ultimate limit on the dimensions of the suturing apparatus 110 and, therefore, the vacuum chamber 146 that can be introduced to capture tissue in accordance with the present invention. The larger the vacuum chamber 146, the larger the "bite" of tissue that can be captured in one throw of the suturing apparatus 110. With this in mind, and as discussed above, the vacuum chamber 146 is made out of an elastomer allowing it to be collapsed during insertion and then "spring" back to its original shape after it is fully inserted.

Figure 13:
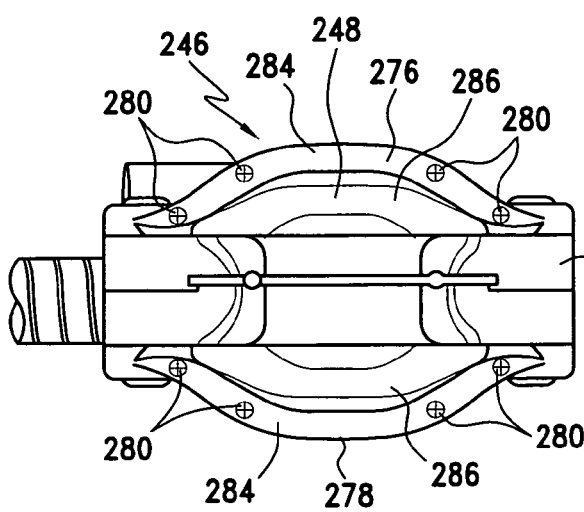
Figure 14:
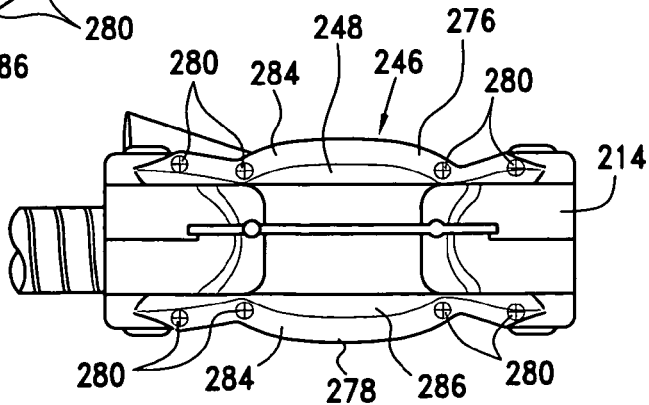

In accordance with an alternate embodiment, and with reference to FIGS. 13 and 14, expansion of the vacuum chamber 246 is further facilitated by the provision of living hinges 280 at predefined bending points of the cavity 248 defined by the vacuum chamber 246. This allows the vacuum chamber 246 to be constructed of a wider variety of materials, including non-elastic plastics, since the living hinges 280 permit the more rigid structures to "fold" rather than elastically bend. More particular, and with reference to the prior embodiment, the vacuum chamber 246 is composed of a first vacuum chamber member 276 and a second vacuum chamber member 278. The first and second vacuum chamber members 276, 278 are mirror images of each other, and each includes a semicircular upper section 284 and a concave lower section 286. As a result, the first and second vacuum chamber members 276, 278 are coupled to opposite sides of the suturing body 214 to form the present vacuum chamber 246, which can similarly include the ribs and/or hooks discussed above with regard to the prior embodiment.

In accordance with a preferred embodiment, the first and second vacuum chamber members 276, 278 are constructed of a semi-rigid material and, therefore, respectively include living hinges 280 permitting expansion and contraction thereof. The living hinges 280 are positioned at predefined bending points of the first and second vacuum chamber members 276, 278 in a manner optimizing folding thereof. The living hinges 280 permits controlled expansion and contraction of the vacuum chamber 246 as the first and second vacuum chamber members 276, 278 are moved relative to each other in accordance with the present invention. One is, therefore, able to pass a vacuum chamber 246 that is ultimately, when used, larger than the trans-oral space through which it is passed.

Those skilled in the art will appreciate it is would be desirable to make a vacuum chamber and central opening adapted to accommodate any type of tissue, any thickness of tissue and be able to allow the user to adjust the bite size (that is, the extent of tissue through which the suture is thrown). To this end, various embodiments for the adjustment of the effective vacuum chamber and central opening size have been developed and are disclosed herein. These embodiments also allow for longitudinal and lateral adjustment of the vacuum chamber, as well as depth adjustment of the central opening and vacuum chamber, to allow for use with different tissue thicknesses, different tissue types and variable tissue bites per suture throw. In this way the surgeon is allowed to readily adjust the effective vacuum chamber/central opening depth, width and/or length to allow for adjustment of the depth of the tissue bite, which controls the depth of the needle path through the tissue (i.e., full thickness or partial thickness). The ability for adjustment also allows the same suturing apparatus to be used for multiple tissue types and thicknesses. While limiting the maximum amount of tissue that may be drawn into the vacuum chamber and central opening, the present techniques may also be applied to ensure that a predetermined and controlled amount of tissue is drawn into the vacuum chamber and the central opening.

Figure 89:
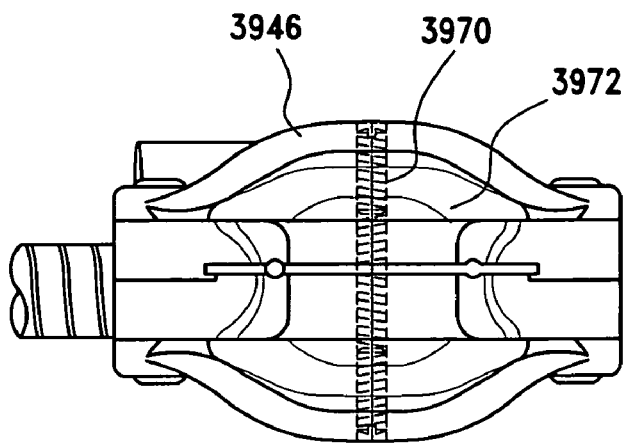
FIGS. 89, 90 and 91 disclose screw-based mechanisms for adjusting the size of the vacuum chamber and central opening.
Figure 90:
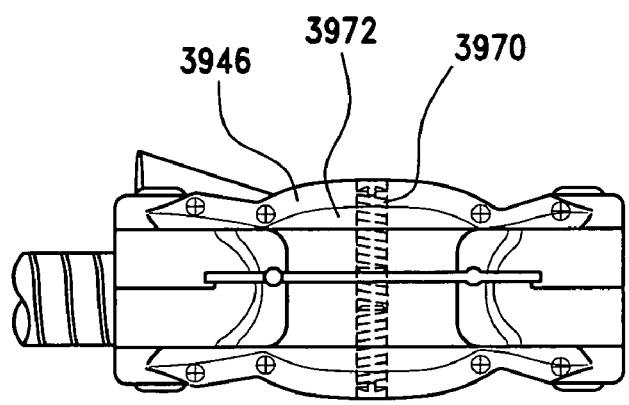
Figure 91:
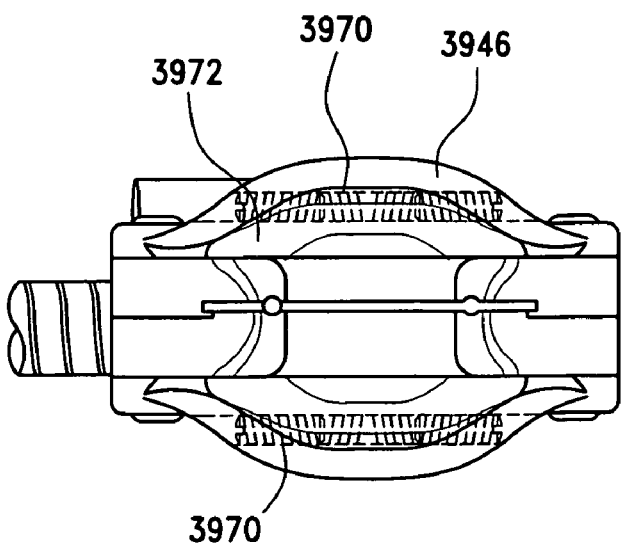

In accordance with a preferred embodiment, and with reference to FIGS. 89, 90 and 91, adjustment is accomplished by the provision of adjusting screws 3970 in the base 3972 of the vacuum chamber 3946. The screws 3970 respectively allow for longitudinal or lateral adjustment of the vacuum chamber 3946 by adjusting a screw 3970 in the base 3972 of the vacuum chamber 3946 that expands or contracts the vacuum chamber 3946 in a desired direction.

Figure 92:
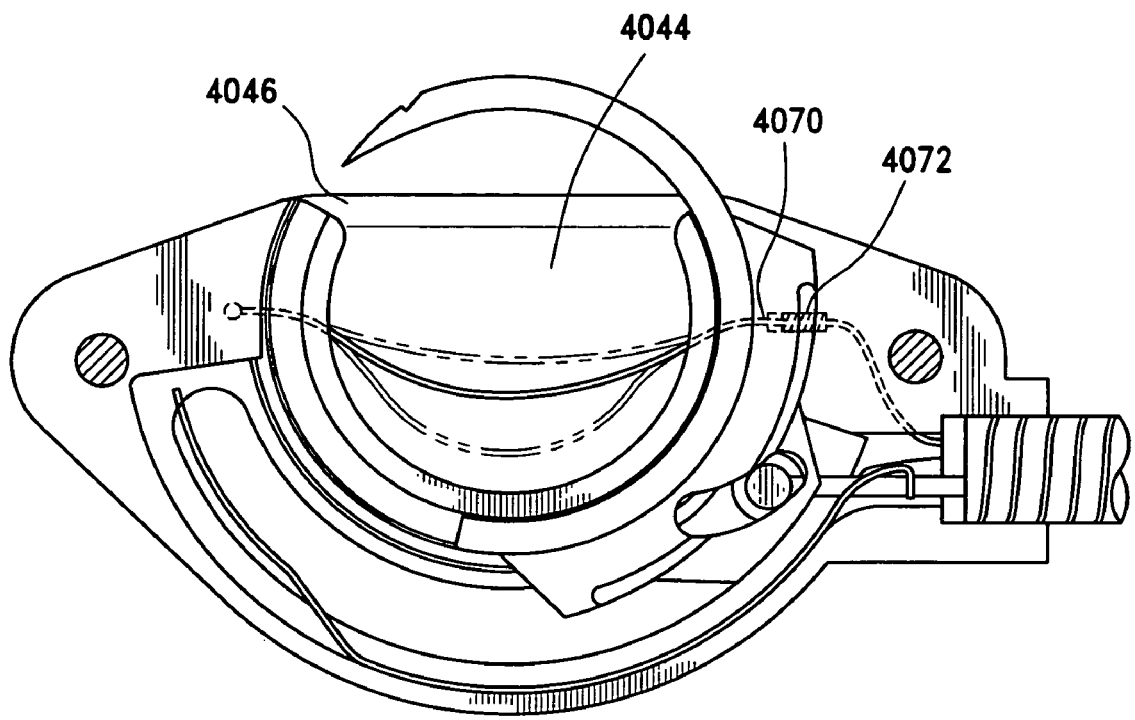
FIG. 92 is a cut away view showing a wire-based mechanism for adjusting the effective depth of the vacuum chamber and central opening.

In accordance with another embodiment, and with reference to FIG. 92 a wire 4070 is used to raise the effective base of the vacuum chamber 4046 and the central opening 4044 controlling the effective depth of the vacuum chamber 4046 and the central opening 4044. This wire 4070 is a buckled spacing wire that can be further buckled or allowed to straighten, effectively reducing the depth to which the tissue can enter the cavity defined by the central opening 4044 and the vacuum chamber 4046. The straighter the spring wire 4070 is allowed to be, the higher the effective bottom of the cavity is set. The spring wire 4070 thereby prevents deep entrance of tissue (that is, entrance beyond the barrier created by the spring wire 4070) into the central opening 4044. The slack in the wire 4070 is controlled via a screw member 4072 found within the suturing body 4014 for actuation of the wire 4070.

Figure 93:
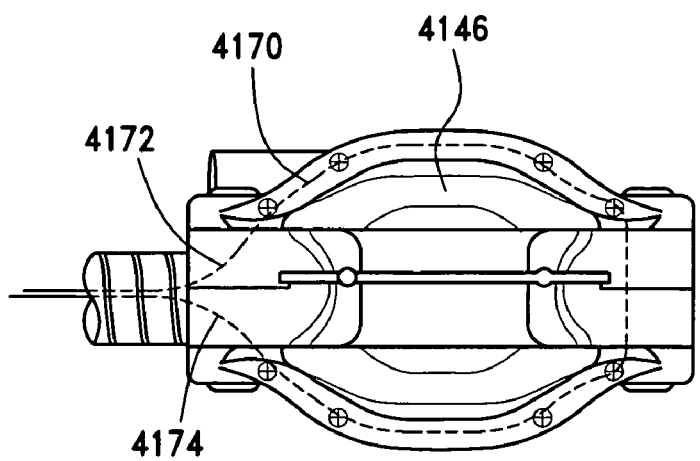
FIG. 93 is a top view showing a cinching line utilized in adjusting the effective size of the vacuum chamber and central opening.

Referring to FIG. 93, and in accordance with another embodiment, a cinching cable 4170 is used to adjust the effective length of the vacuum chamber 4148. In particular, a cinching cable 4170 is threaded about the outer perimeter of the vacuum chamber 4146, with the free ends 4172, 4174 thereof exiting at the proximal end of the vacuum chamber 4146. As such, the free ends 4172, 4174 may be tensioned to shorten the vacuum chamber 4146 length, and similarly released when it is desired to increase the length of the vacuum chamber 4146 by allowing the walls thereof to expand to their unbiased position.

As mentioned above, the housing 24 contains the needle 28 used in the application of a suture 12 to the tissue drawn within the central opening 44. The suture 12 is secured to the proximal end, that is, the blunt end, of the needle 28 and is drawn through the tissue as the needle 28 is actuated in accordance with the present invention as described herein. In accordance with a preferred embodiment, the needle 28 is curved to rotate about a predetermined continuous circular path and extends along an arc of 240 degrees creating an opening of 120 degrees. However, those skilled in the art will appreciate the opening may be varied; for example, it has been contemplated to use a needle offering an opening of 140 degrees.

The needle 28 includes an interior surface 52 along the inner surface of the arc defined by the needle 28 and an exterior surface 54 along the outer surface of the arc defined by the needle 28. A series of notches 56 are cut into the exterior surface 54 of the needle 28. As will be appreciated based upon the following description, the notches 56 are shaped and dimensioned for use by the drive assembly 30 in grabbing, driving and releasing the needle 28. Although notches along the exterior surface of the needle are disclosed for use in accordance with a preferred embodiment of the present invention, it is contemplated the needle may be formed without notches such that the drive assembly merely grips the substantially smooth exterior surface of the needle to drive it forward.

Operation of the drive assembly 30 and movement of the needle 28 is described with reference to FIGS. 3 to 10, wherein one half of the housing 24 is removed exposing internal components of the present suture apparatus 10. The drive cable 42 (shown in FIG. 3) is rigidly attached to the pin 40. As is described below in greater detail, the drive cable 42, pin 40 and friction camming member 38 are extended and retracted to engage and disengage the needle 28 for movement thereof about its circular path. The drive cable 42 is flexible enough to curve in the housing 24 and flex along with the endoscope 18, but is rigid enough to be compressed to drive the friction camming member 38 into its initial drive stage (see FIG. 4).

The friction camming member 38 is composed of an arcuate engagement member 58 and a camming member 60 working in conjunction with the pin 40 to control the position of the engagement member 58 for selective engagement with the needle 28. The engagement member 58 is constructed with internal notches 62 shaped and dimensioned for engaging the needle 28 to drive it in a clockwise direction, but permit free movement thereof as the friction camming member 38, that is, both the engagement member 58 and the camming member 60, is moved in a counter-clockwise direction toward the initial drive stage.

The engagement member 58 of the friction camming member 38 is designed to translate in the housing 24 both radially towards and away from the needle 28, as well as translate arcuately clockwise and counterclockwise about the arc defined by the housing 24. This is achieved through the camming action offered by the interaction between the camming member 60, the pin 40 and the engagement member 58. The camming member 60 is rigidly coupled to the engagement member 58 such that the engagement member 58 is moved into and out of engagement with the needle 28 as the radial position of the camming member 60 is altered based upon its interaction with the pin 40. As discussed below in accordance with an alternate embodiment, it is contemplated that a spring element may be employed to force the friction camming member 38 against the needle 28.

More particularly, as the drive cable 42 is compressed (that is, the drive cable 42 is pushed distally away from the operation of the suturing apparatus 10) to move the friction camming member 38 in a counter-clockwise direction, the pin 40 slides within a slot 64 formed in the camming member 60 forcing the engagement member 58 and camming member 60 to move counterclockwise as well as outwardly from the needle 28. The friction plate 36 aids in forcing the engagement member 58 outwardly from the needle 28 as the friction camming member 38 is moved in this counter-clockwise direction.

Figure 4:
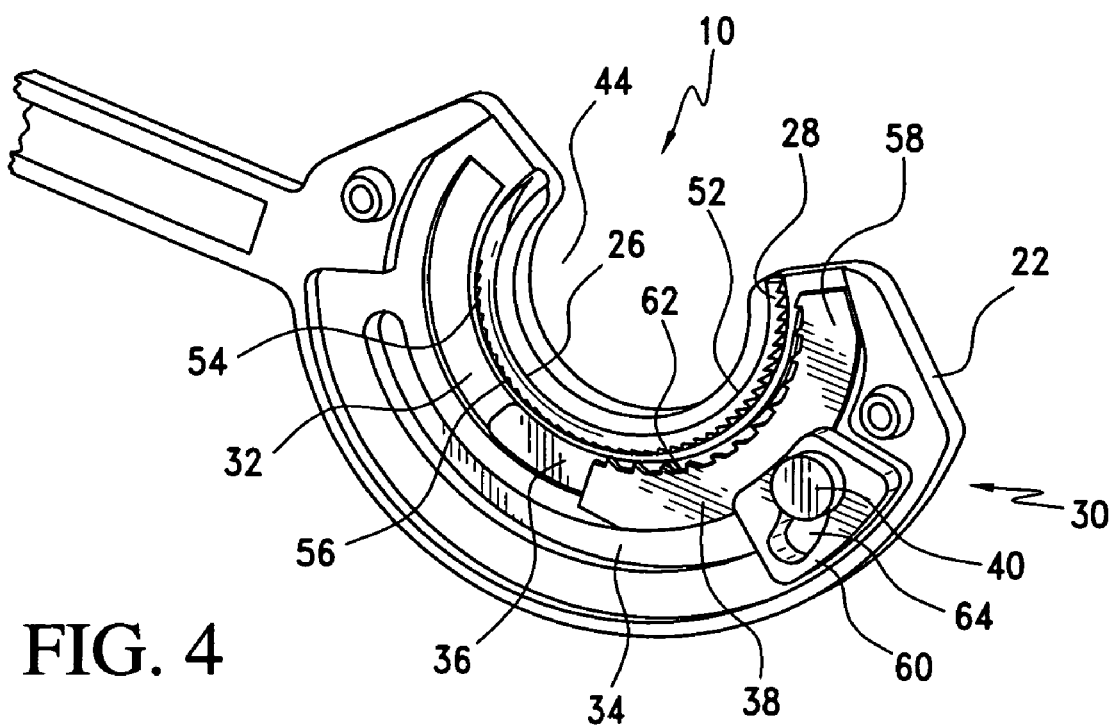
Figure 5:
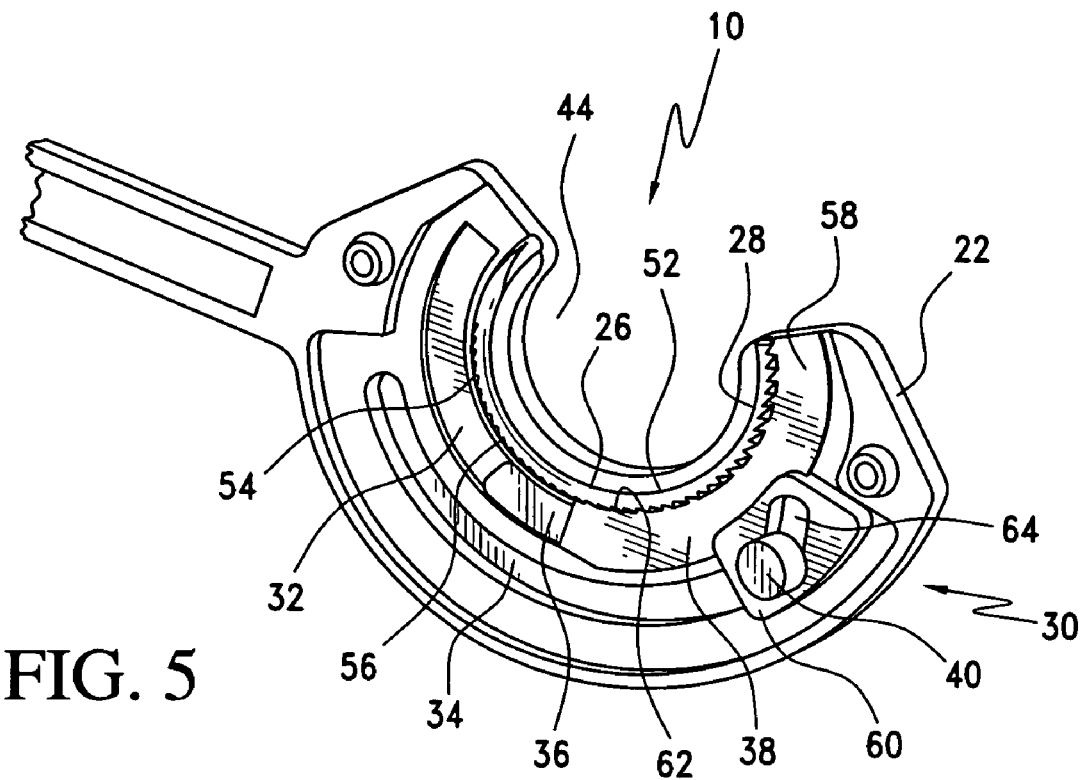

With the friction camming member 38 in its initial drive position as shown in FIG. 4, and as tension is applied to the drive cable 42 (that is, the drive cable 42 is pulled proximally toward the operation of the suturing apparatus 10) and ultimately the pin 40, the pin 40 engages the camming member 60 forcing friction camming member 38, and more particularly, the engagement member 58 to travel inwardly into contact with the exterior surface 54 of the needle 28 due to the camming action resulting from the interaction of the pin 40 and the slot 64 within the camming member 60 (see FIG. 5). As tension is continually applied to the drive cable 42 the notches 62 formed along the inner surface of the engagement member 58 grab into the notches 56 cut into the exterior surface 54 of the needle 28, causing the needle 28 to rotate clockwise until pin 40 reaches the limit of track 34 and the procedure must start all over (see FIG. 6).

Figure 6:
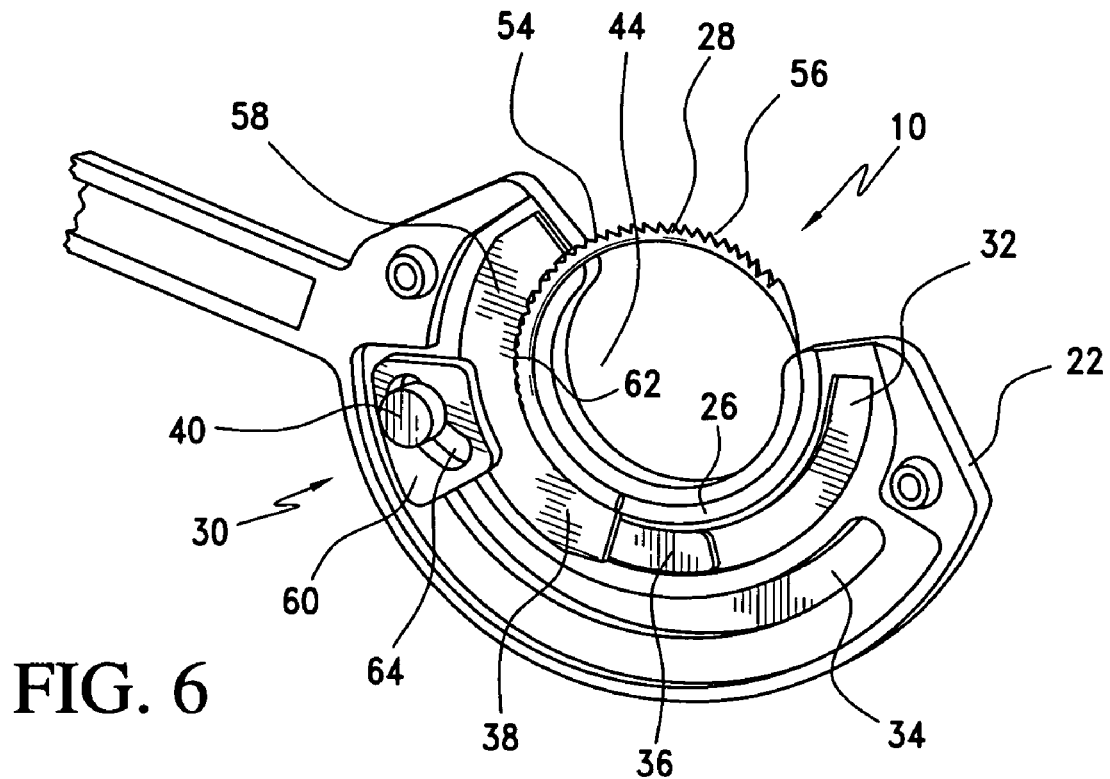
Figure 7:
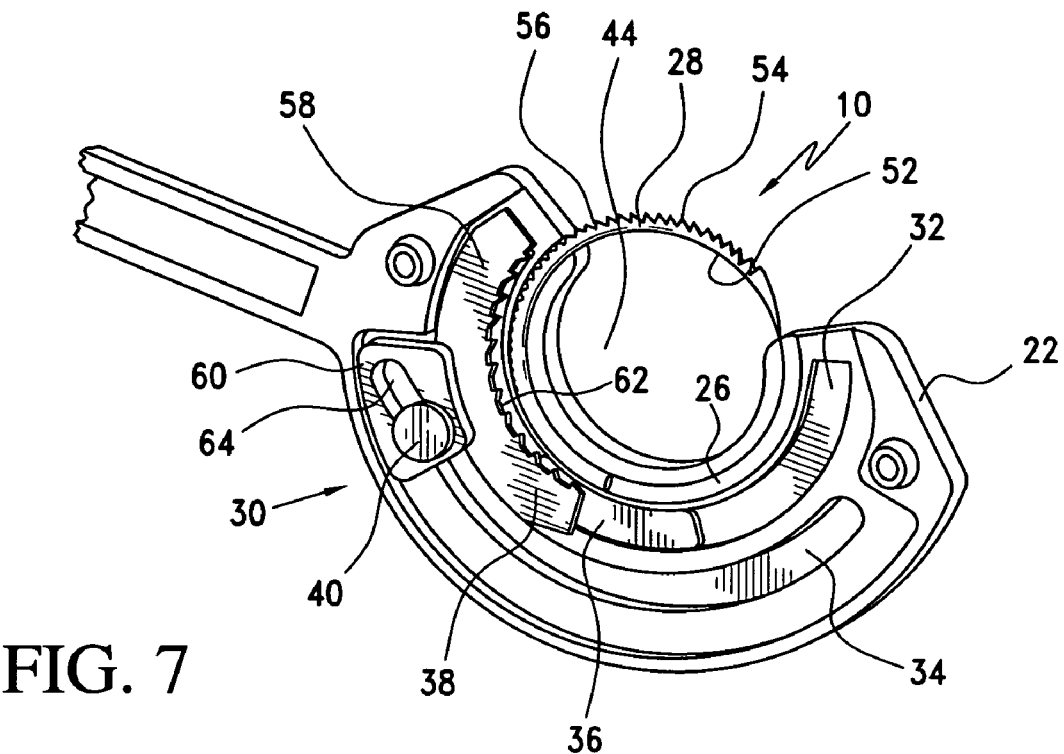

When the limit of the stroke is reached as shown in FIG. 6, the operator compresses the drive cable 42 causing the engagement member 58 to disengage from the needle 28 by way of the cam feature resulting from the interaction of the pin 40 within the slot 64 of the camming member 60 as the pin 40 slides within the slot 64 causing the engagement member 58 and camming member 60 to move outwardly and in a counterclockwise direction (see FIG. 7). The compression on the drive cable 42 is continued until the friction camming member 38 moves counterclockwise reaching the opposite end of the housing 24 (see FIG. 8). Tension is then applied to once again move the needle 28 in a clockwise direction and the procedure is repeated until the needle has traveled 360 degrees (see FIGS. 9 and 10).

Figure 15:
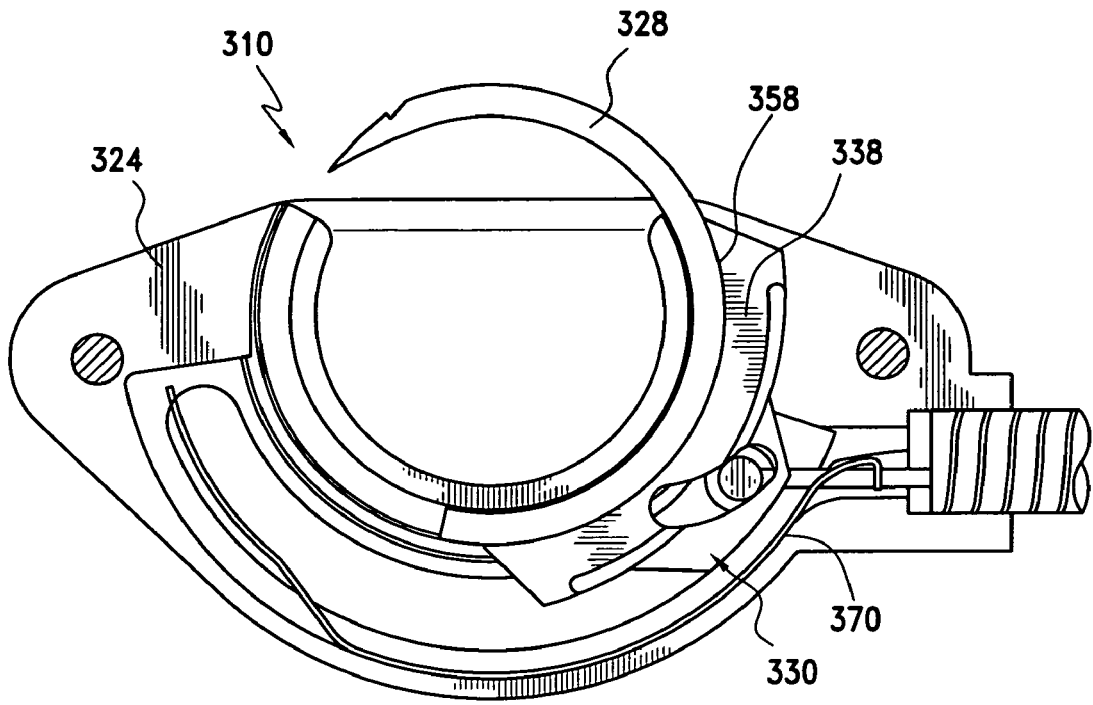
FIG. 15 is a cut away view of the suturing body showing a smooth friction camming member.

As briefly discussed above, the drive assembly 30 of the present invention is capable of driving the needle 28 about its circular path in a highly controlled and efficient manner. Referring to FIG. 15, the functionality of the present drive assembly 330 is enhanced by the provision of the friction camming member 338, which drives the needle 328 when pulling the needle 328 along its path through frictional means. The contact surface of the frictional interface 358 of the friction camming member 338 is manufactured to enhance its frictional relationship with the needle 328 so as to smoothly and reliably move the needle 328 in accordance with the present invention.

The interaction between the friction camming member 338 and the needle 328 is enhanced by the provision of a leaf spring 370. The leaf spring 370 extends within the suture housing 324 of the suturing apparatus 310 and is oriented to contact the friction camming member 338 during actuation of the needle 328 for forcing the friction camming member 338 into contact with the needle 328. The leaf spring 370 is a cantilever mounted spring member mounted proximally of the friction camming member 338. As the friction camming member 338 is forced distally, the leaf spring 370 increases the engagement forces radially the farther the friction camming member 338 is displaced. As those skilled in the art will certainly appreciate, a spring structure is disclosed in accordance with a preferred embodiment of the present invention and other spring structures could be employed without departing from the spirit of the present invention.

Figure 16:
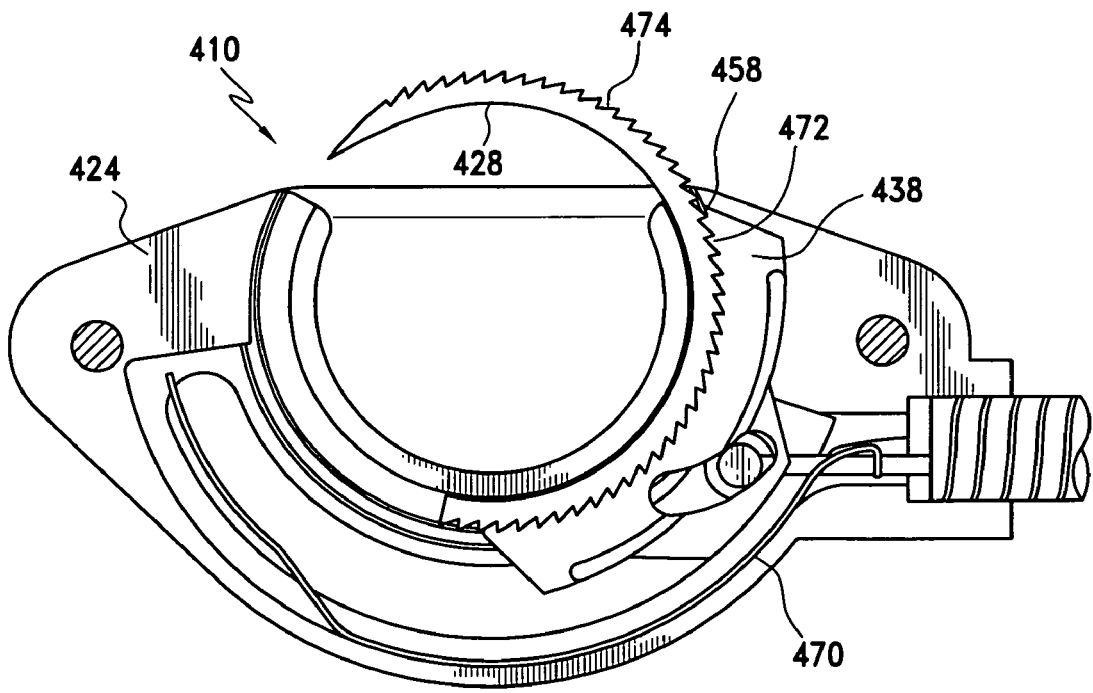
FIG. 16 is an alternate embodiment of the suturing body showing a toothed friction camming member.

In accordance with an alternate embodiment, and with reference to FIG. 16, the smooth friction camming member 338 discussed above may be replaced with a toothed friction camming member 438. In accordance with this embodiment, the contact surface of the frictional interface 458 of the friction camming member 438 is provided with teeth 472 shaped and dimensioned to engage similarly shaped teeth 474 formed along the exterior surface of needle 428. In this way, the teeth 472 along the frictional interface 458 of the friction camming member 438 engage teeth 474 cut into the needle 428 and drag the needle 428 along its drive path when pulled. As with the prior embodiment, the interaction between the friction camming member 438 and the needle 428 is enhanced by the provision of a leaf spring 470. The leaf spring 470 extends within the suture housing 424 of the suturing apparatus 410 and is oriented to contact the friction camming member 438 during actuation of the needle 428 for forcing the friction camming member 438 into contact with the needle 428.

Figure 17:
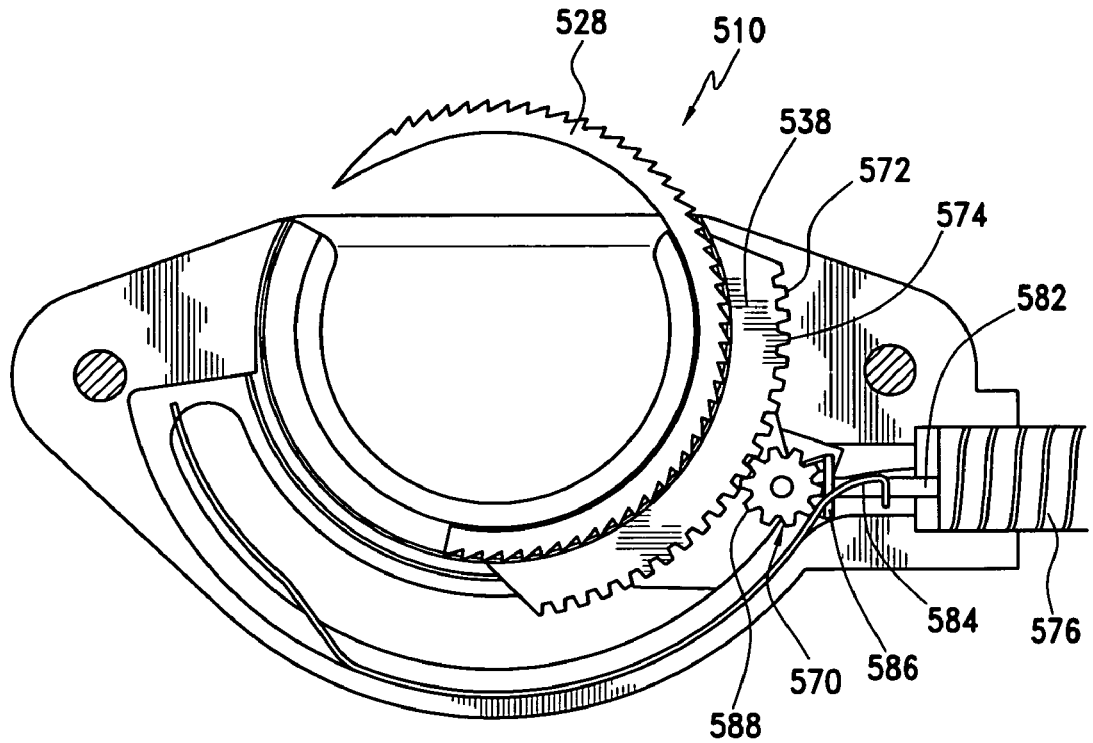
FIG. 17 is a cut away view of yet another embodiment of the suturing body with a gear driven friction camming member.

In accordance with an alternate embodiment, and with reference to FIG. 17, The motion of the friction camming member 538 (whether it be a smooth friction camming member 338 as shown in FIG. 15 or a toothed friction camming member 438 as shown in FIG. 16) used in driving the needle 528 can also be achieved through the use of a sprocket gear 570 engaging with teeth 572 on the back side 574 of the friction camming member 538 driving the needle 528 through the same motions the linear pull system created. Such a gearing arrangement provides for the translation of rotary motion along the drive cable 582, and about a first axis substantially aligned with the longitudinal axis of the suturing apparatus 510 extending through the suturing apparatus 510, into rotary motion of the needle 528 about an arcuate path having a central axis substantially perpendicular to the longitudinal axis of the suturing apparatus 510. In accordance with this embodiment, the sprocket gear 570 is rotated by a rotary cable drive system 576 linked to a rotary member in the handle (not shown) which would replace the linear pull system. In accordance with this embodiment, the rotary cable motion (rotating about the longitudinal axis of the device shaft) is converted to rotary motion (rotating perpendicular to the longitudinal axis of the device shaft) to drive the needle 528 directly along its circular path or to drive the toothed friction camming member 538 in its path.

More particularly, the drive cable 582 is designed for rotation about an axis substantially parallel to the longitudinal axis of the apparatus 510. The distal end 584 of the drive cable 582 is provide with spur gear 586 which is linked to a similar spur gear 588 mounted between the spur gear 586 at the distal end 584 of the drive cable 582 and a geared contact surface 574 of the friction camming member 538. As a result, rotation of the drive cable 582 causes the spur gear 586 to rotate, which in turns translates into motion of the friction camming member 538. Movement of the friction camming member 538 then causes the needle 528 to move in a desired arcuate path. Since the friction camming member 538 engages and disengages the needle 528 in a manner similar to the embodiment described above, movement of the needle 528 is achieved by alternately reversing the rotation of the rotary cable system. Forward rotation cams the friction camming member 538 into engagement and drives the friction camming member 538 counter-clockwise in a manner driving the needle 528. Reverse rotation of the drive cable 582 disengages the friction camming member 538 from the needle 528 and rotates the friction camming member 538 clockwise resetting it for the next driving motion.

Regardless of the friction camming member design, the drive mechanism employed in accordance with preferred embodiments of the present invention provides a rotary needle drive system for suture pass-through capable of multiple tissue pass-through during a single device insertion. As discussed above, in accordance with a preferred embodiment of the present invention, this is accomplished by a friction camming member that advances the needle by means of a toothed engagement or a frictional coupling, and provides for needle advancement permitting variation in the size of both the needle and suture used in accordance with the present invention.

Figure 8:
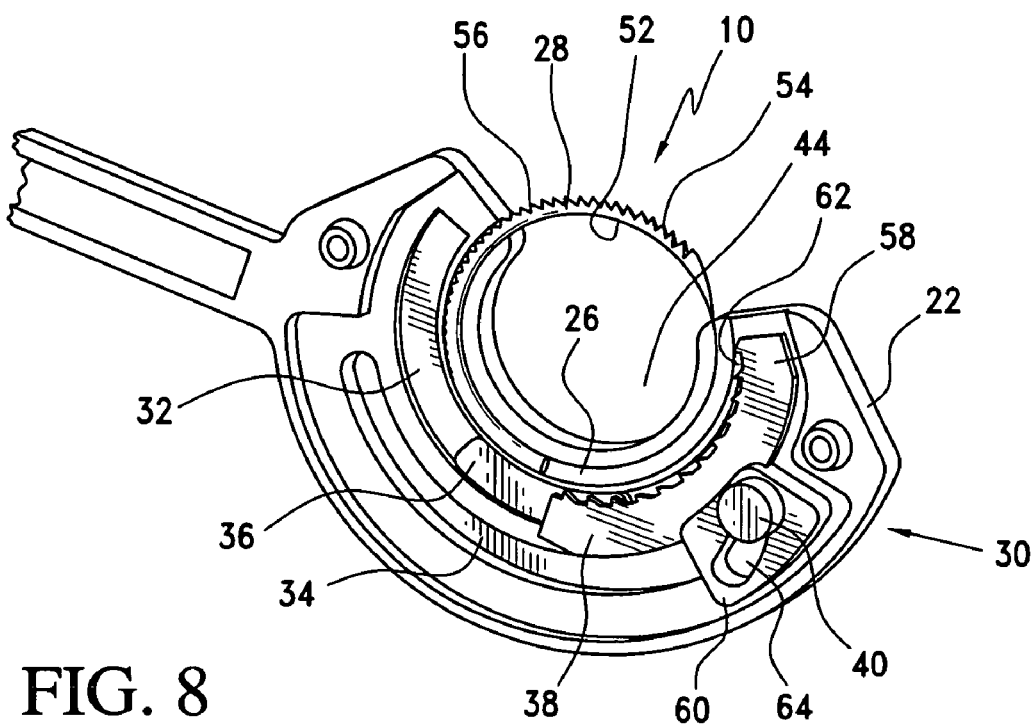
Figure 9:
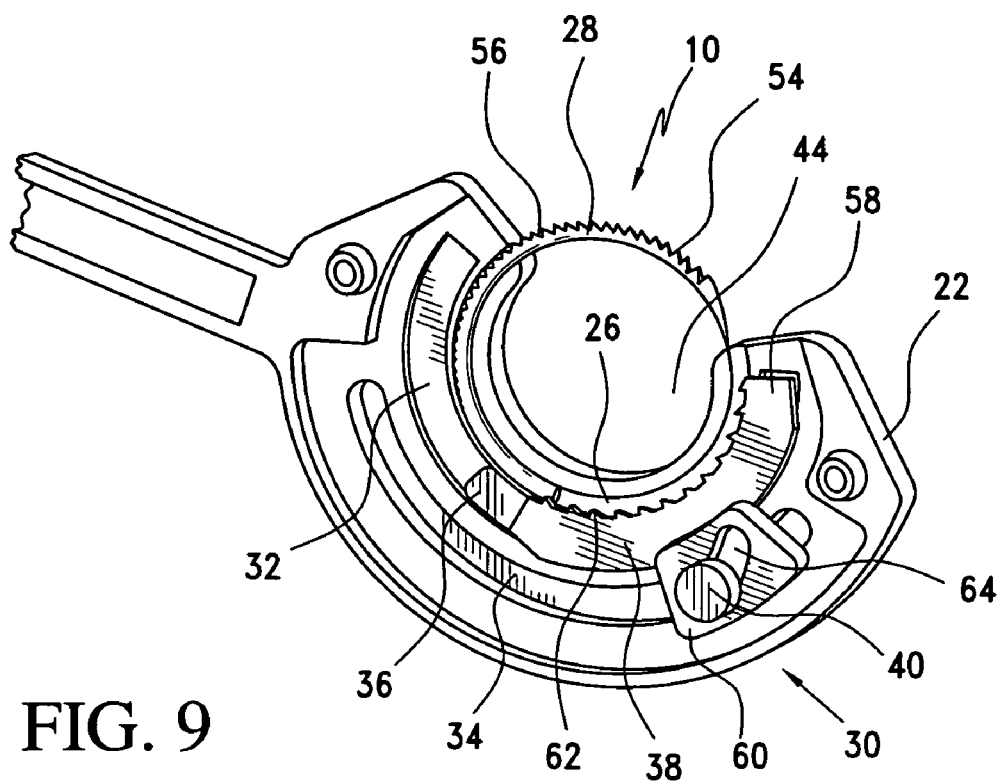
Figure 10:
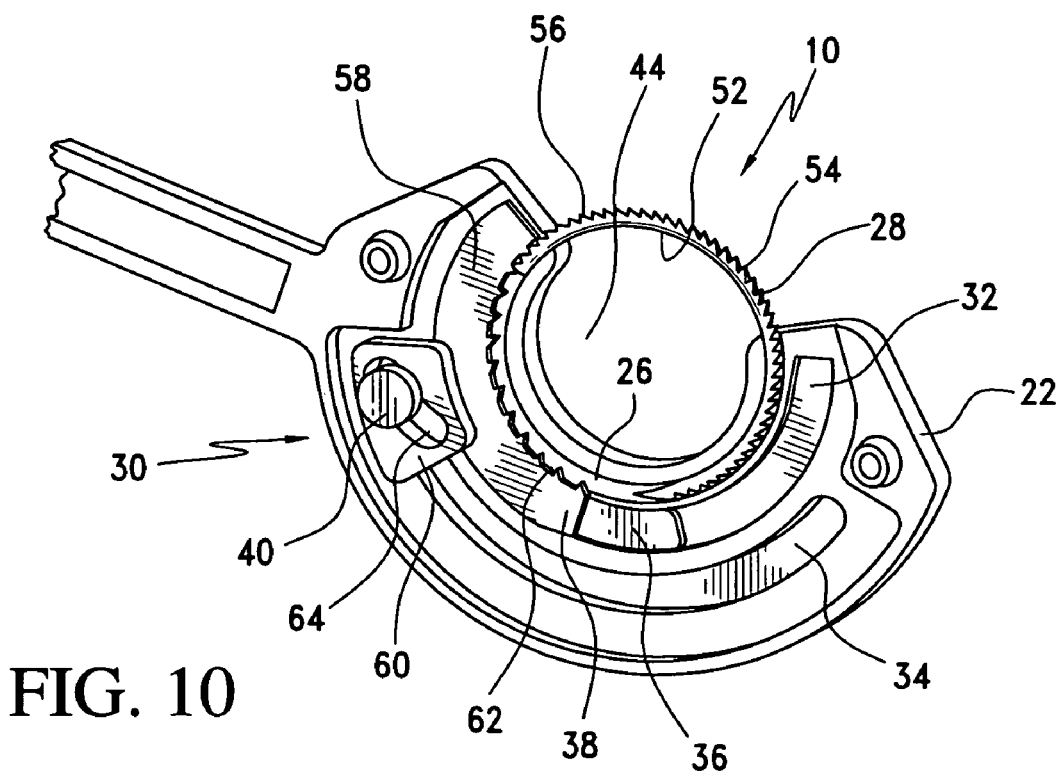
Figure 18:
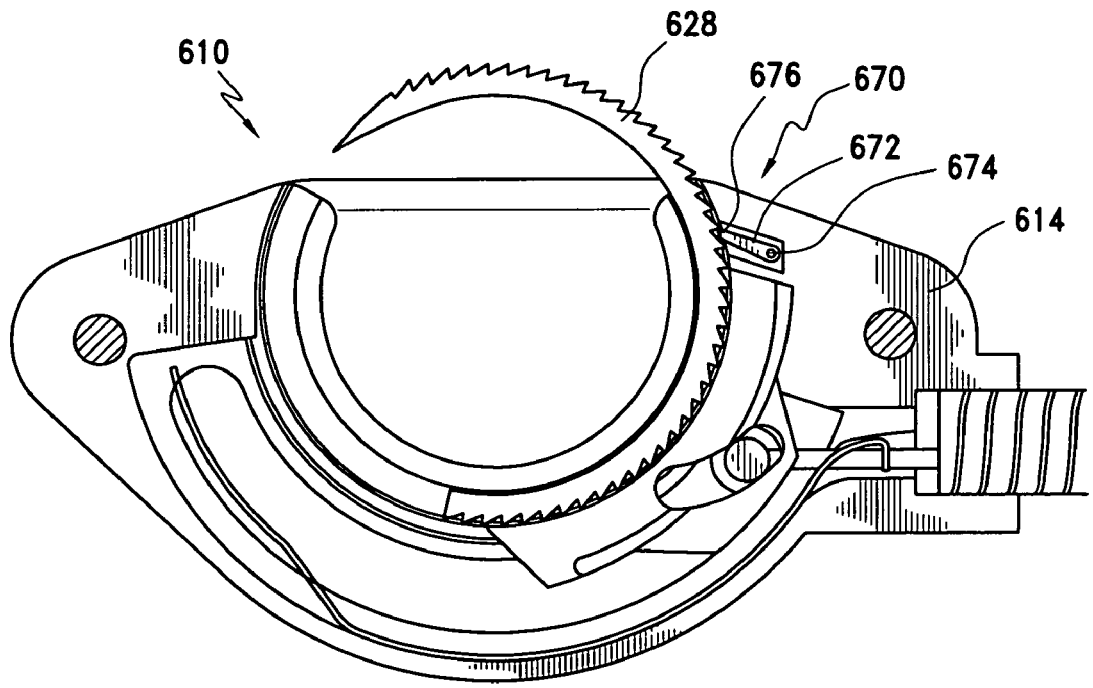
FIGS. 18 and 19 are cut away views of the suturing body showing alternate back-up mechanisms which may be utilized in accordance with the present invention.
Figure 19:
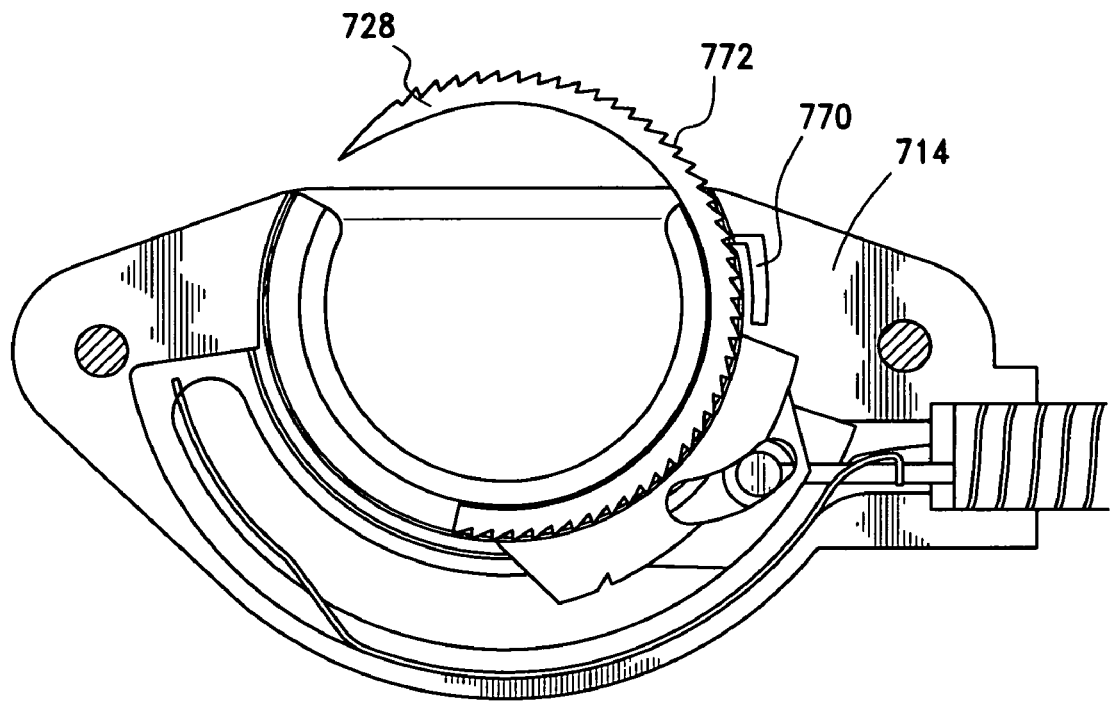

Two anti-backup structures are disclosed with reference to FIGS. 18 and 19. These anti-backup structures control needle movement so the needle is only allowed to pass in one direction. This prevents the needle from backing out between actuating strokes of the friction camming member as it moves between its end (or limit) of stroke position as shown in FIG. 6 and its initial drive position as shown in FIG. 8. More particularly, the needle of the present suturing apparatus is designed to move in a predetermined first direction about an arcuate path, and movement in an opposite second direction is undesired. As such, the present anti-backup structures prevent movement of the needle in the second direction while permitting free movement of the needle in the first direction.

More particularly, and in accordance with a preferred embodiment disclosed with reference to FIG. 18, a frictional anti-backup device 670 is secured along the forward end of the needle 628 path for contact with the needle 628 in a manner preventing undesired back-up thereof. The frictional anti-backup device 670 is a lever arm 672 including a first end 674 and second end 676. The first end 674 of the lever arm 672 is pivotally secured to the suturing body 614 of the suturing apparatus 610. The second end 676 of lever arm 672 extends toward, and into contact with, the contact surface of the needle 628. The lever arm 672 is oriented such that when the needle 628 is moved in a counter-clockwise direction as viewed in FIG. 18, the lever arm 672 slides over the exterior surface of the needle 628 permitting the needle 628 to freely rotate.

However, if the needle 628 attempts to rotate in a clockwise direction as viewed in FIG. 18, the second end 676 of the lever arm 672 frictionally engages the exterior surface of the needle 628 in a manner stopping clockwise rotation thereof. This is a result of the orientation of the lever arm 672 that creates a frictional impediment to movement of the needle 628, for example, similar to a ratchet mechanism. With this in mind, the lever arm 672 is biased to maintain engagement with the exterior surface of the needle 628 whether the needle is rotated in a clockwise direction or a counter-clockwise direction.

In accordance with an alternate embodiment and with reference to FIG. 19, the suturing body 714 is provided with an integral spring biased latch 770 shaped and dimensioned to fit within recesses 772 formed in the exterior surface of the needle 728. With this in mind, the latch 770 and the recesses 772 are shaped and dimensioned to permit substantially free rotation of the needle 728 in one direction while preventing rotation of the needle 728 in the opposite direction.

Since it is possible the needle may become jammed within the tissue during deployment, it sometimes becomes necessary to free the needle from the suturing apparatus for emergency extraction of both the suturing apparatus and the needle. With this in mind, and with reference to the various embodiments presented below, techniques have been developed for freeing the needle in the event it becomes jammed and requires release. In general, the embodiments described below are different methods of separating or opening the suture housing of the suturing apparatus to release the needle and allow the suturing apparatus to be removed. Release of the needle in this manner might necessitate subsequent removal of the needle from its jammed position, but will permit extraction of the remainder of the suturing apparatus as the suturing apparatus is no longer hung on the tissue based upon the release of the needle.

In accordance with the various embodiments disclosed below, a surgical suturing apparatus includes a suture housing and a needle mounted within the suture housing for movement about an arcuate path. The suturing apparatus also includes a drive assembly operably associated with the needle for controlling movement of the needle with a suture secured thereto about the arcuate path in a manner facilitating application of the suture to tissue. The suture housing has an open position and a closed position, and the needle can be removed from the suture housing when in the open position.

The various embodiments provide a user a controlled opening mechanism that allows the suture housing to be selectively opened should the needle fail to be able to advance and the suturing apparatus needs to be extracted. As will be described below in greater detail, this is achieved by employing either a spring biased, hinged clamshell suturing body opening when a crushable coupling mechanism is actuated, a removable pin/cable mechanism that holds the two halves of the suturing body together or an openable suture deployment system that can be re-closed for extraction from the body.

Figure 20:
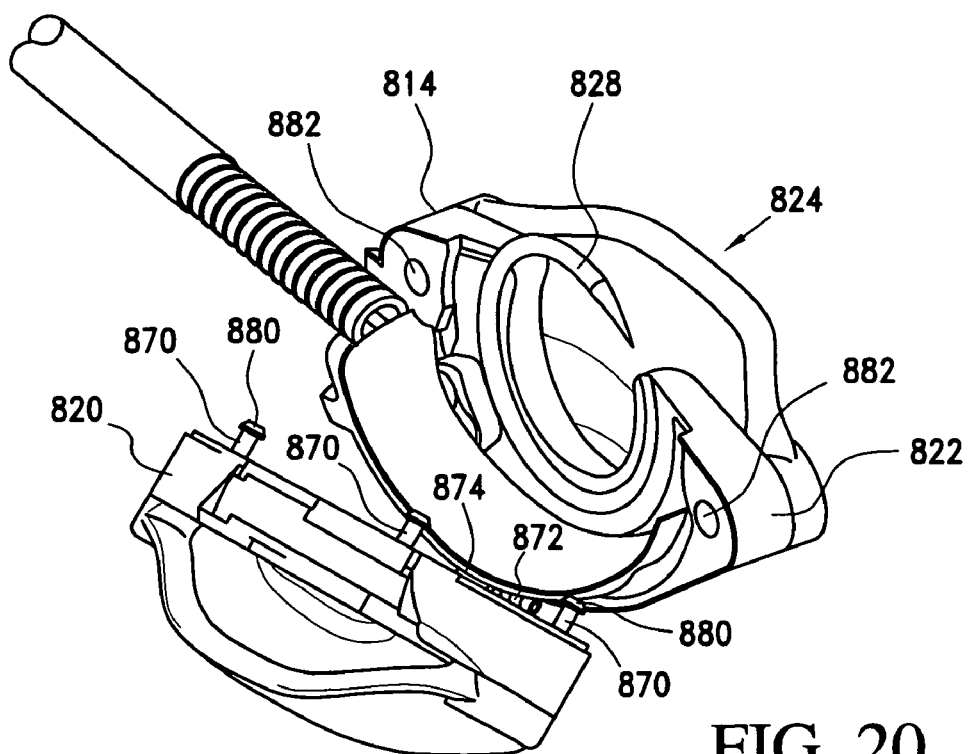
FIGS. 20, 21 and 22 are various views of a suturing body including a cam pin set mechanism utilized in selectively opening the suture housing.
Figure 21:
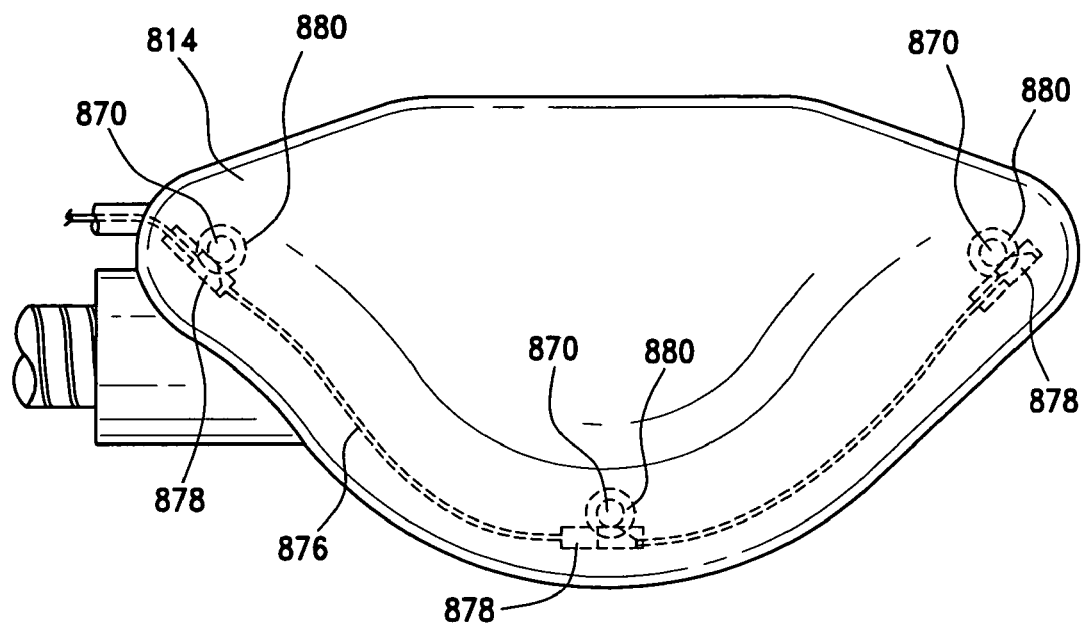
Figure 22:
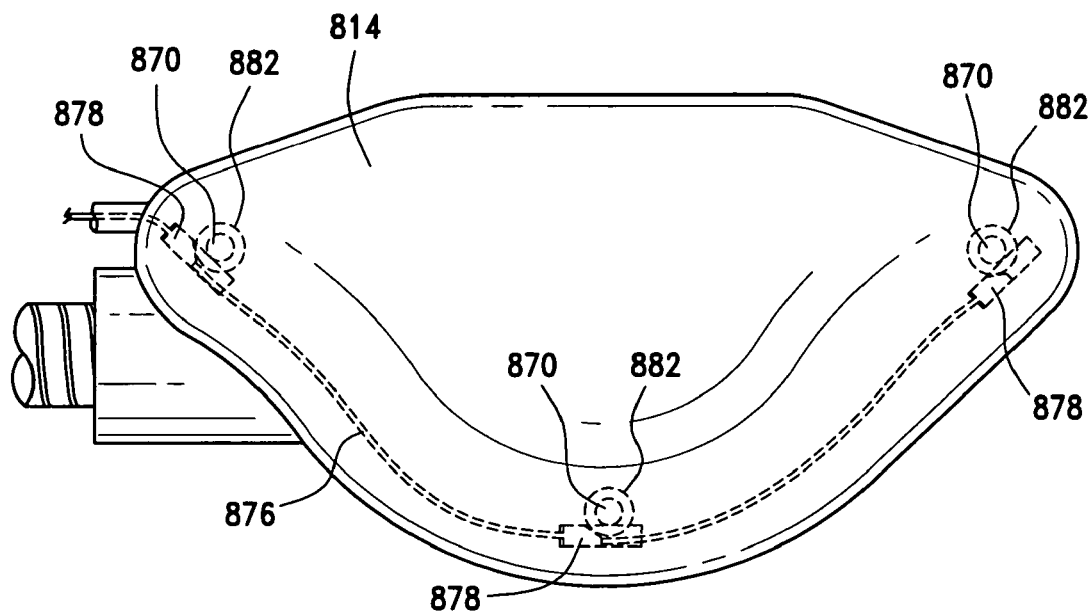

In accordance with a first embodiment, and with reference to FIGS. 20 to 22, and as discussed above in greater detail, the suturing body 814 is composed of a first housing member 820 and second housing member 822 making up the suture housing 824. A cam pin set 870 locks the first housing member 820 and the second housing member 822 together, with, however, the ability to remove the cam pin set 870 from the second housing member 822 when it is desired to separate the first and second housing members 820, 822 for removal of a jammed needle 828.

More particularly, the first and second housing members 820, 822 are hinged 872 along one end thereof, and the cam pin set 870 is positioned in a manner opposite the hinge 872 so the first and second housing members 820, 822 are securely held together. However, when the cam pin set 870 is removed, or otherwise removed from its locking position with a second housing member 822, the first and second housing members 820, 822 are free to move apart pivoting about the hinge 872. Opening of the suturing housing 824 is further facilitated by the inclusion of a spring 874 in the hinge 872 for encouraging opening of the suturing housing 824 upon removal of the cam pin set 870.

Actuation of the cam pin set 870 is achieved via the use of a release member 876 that interacts to permit controlled locking and release of the cam pin set 870. In particular, the release member 876 includes a series of interference members 878 which interact with the heads 880 of the cam pin set 870 to retain them within recesses 882 formed in the second housing member 822 (see FIG. 21). When it is desired to separate the first and second housing members 820, 822, the release member 876 is shifted, for example, via a cable 884 extending for actuation by a user, to move the interference member 878 and allow the cam pin set 870 to move from within the second housing member 822 (see FIG. 22).

Figure 23:
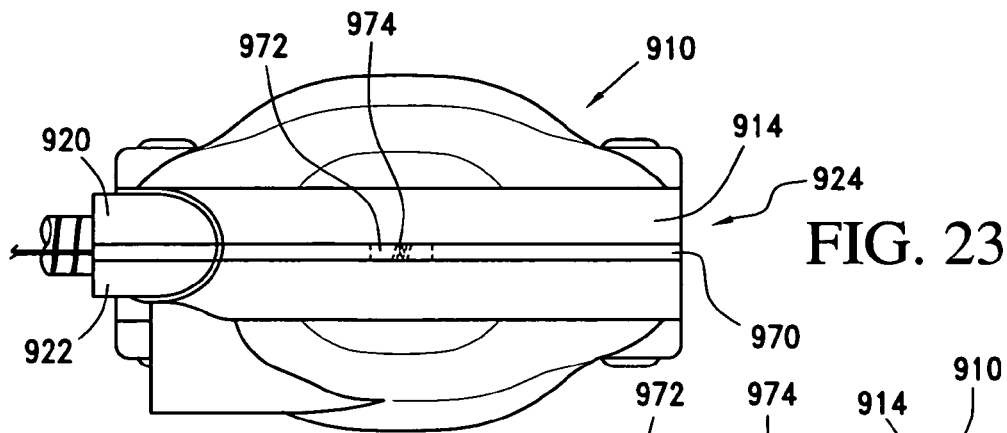
FIGS. 23 and 24 are bottom views of a suturing body showing a tear strip mechanism utilized in selectively opening the suture housing.
Figure 24:
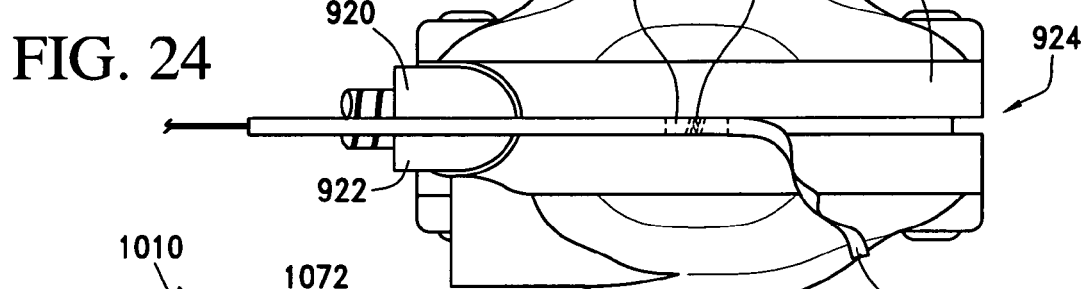

In accordance with another embodiment, and with reference to FIGS. 23 and 24, a tear strip 970 is disclosed. As with the prior embodiments, the suturing body 914 is composed of a first housing member 920 and second housing member 922 making up the suture housing 924. The first and second housing members 920, 922 are hinged 972 along one end thereof, with a spring 974 biasing the first and second housing members 920, 922 to an open orientation.

The tear strip 970 is positioned through the centerline of the first and second housing members 920, 922. In accordance with a preferred embodiment, the tear strip 970 is secured to the first and second housing members 920, 922 either through adhesive or other mechanical frangible, plastic coupling features. When pulled, the tear strip 970 "tears" the center out from between the first and second housing members 920, 922 allowing the suturing apparatus 910 to fall open. The tear strip 970 may be a straight adhesive or molded strip, or the tear strip 970 may include a camming feature (as discussed below) as part of the distal most end further spreading open the halves as it is removed.

Figure 25:
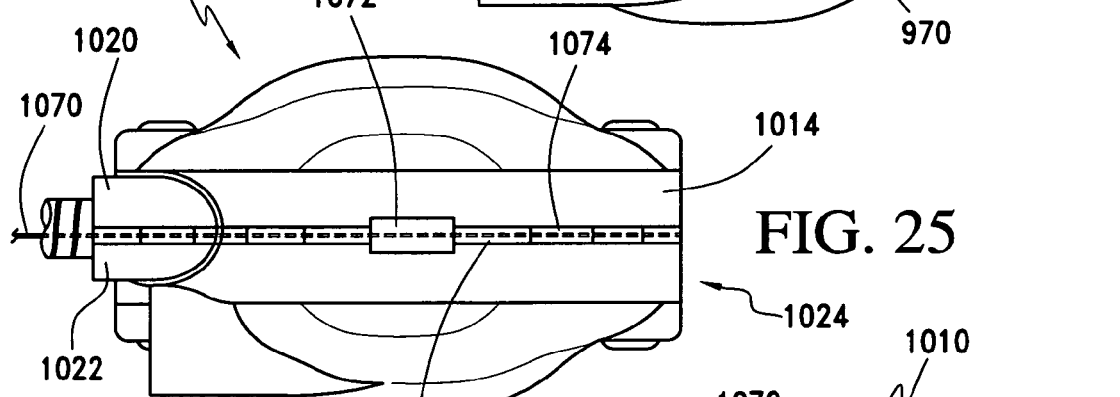
FIGS. 25 and 26 are bottom views of a suturing body showing yet another mechanism utilized in selectively opening the suture housing.
Figure 26:
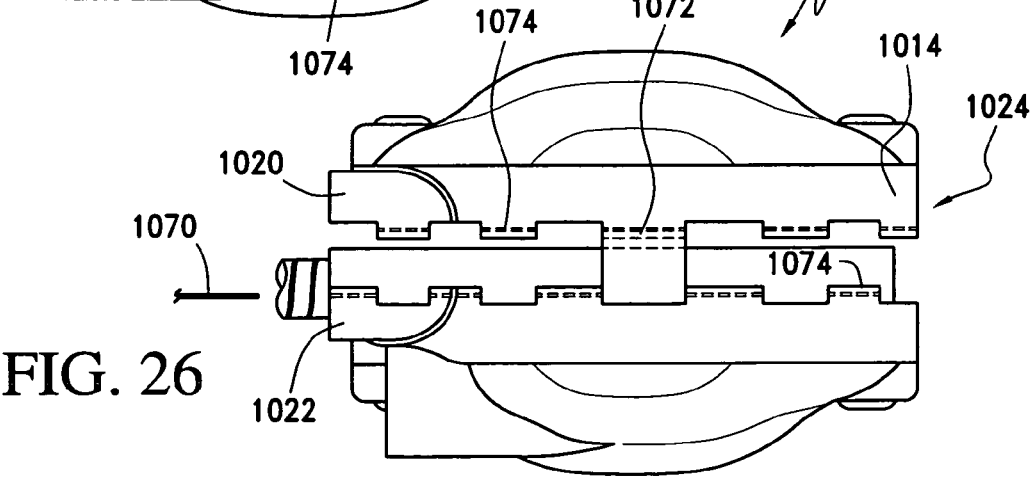

A further embodiment is disclosed with reference to FIGS. 25 and 26. This embodiment employs a pull cable 1070 to facilitate selective opening of the suturing body 1014 for release of a jammed needle therefrom. In accordance with this embodiment, the suturing body 1014 is composed of a first housing member 1020 and second housing member 1022 making up a suture housing 1024. The first and second housing members 1020, 1022 are hinged 1072 along one end thereof (or are separate non-associated halves). The first and second housing members 1020, 1022 are further provided with lacing loops 1074 along the open end thereof. The lacing loops 1074 are shaped and dimensioned to permit the placement of a pull cable 1070 therethrough in a manner which holds the first and second housing members 1020, 1022 together.

More particularly, the pull cable 1070 is laced through the lacing loops 1074 alternately positioned on the first and second housing members 1020, 1022 much like the hinge of a door. As long as the pull cable 1070 is present around the perimeter of the first and second housing members 1020, 1022, the first and second housing members 1020, 1022 are held together and the needle 1028 is retained therein. However, when it is desirable to remove the needle 1028 or otherwise open the suturing body 1014 of the suturing apparatus 1010, the pull cable 1070 is pulled withdrawing it from the lacing loops 1074 and releasing the first and second housing members 1020, 1022 from each other. With the first and second housing members 1020, 1022 released, the spring biased hinge 1072 draws the first and second housing members 1020, 1022 apart by pivoting them along the hinge 1072.

Figure 27:
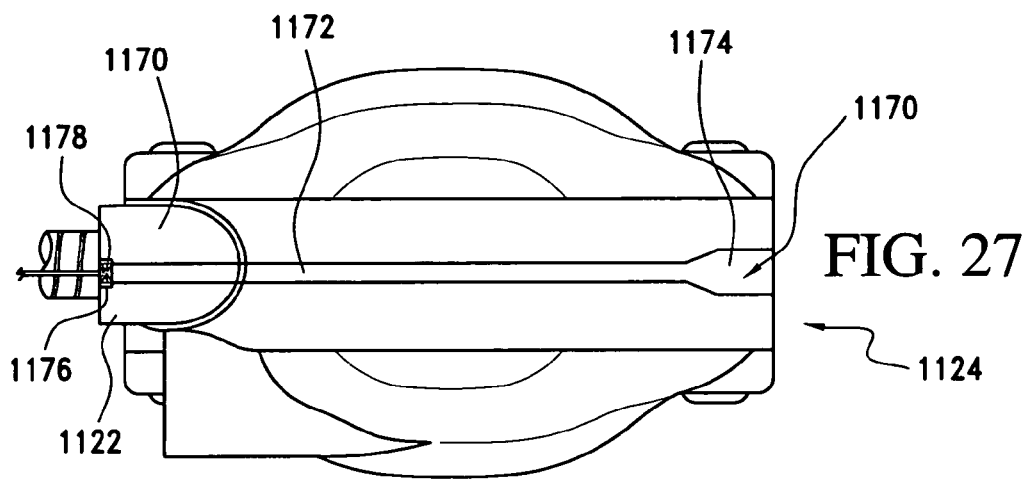
FIGS. 27 and 28 are bottom views of a suturing body showing a spreader plate mechanism utilized in selectively opening the suture housing.
Figure 28:
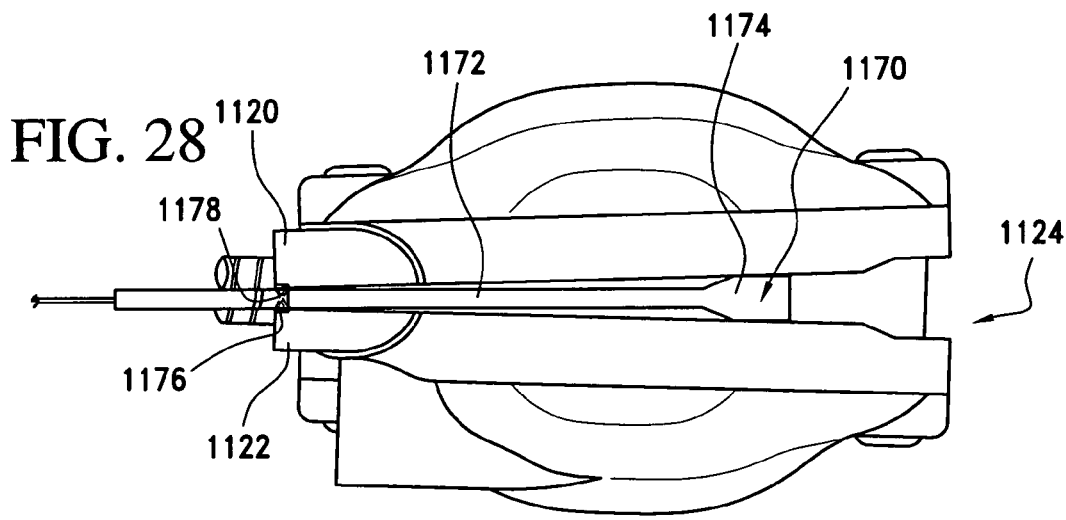

A spreader plate 1170 embodiment is disclosed with reference to FIGS. 27 and 28. This is a variation on the tear strip design disclosed above with reference to FIGS. 23 and 24. In accordance with this embodiment, the center connection member 1172 not only joins and releases the two housing members 1120, 1122, but has a camming member 1174 on the distal end of the center connection member 1172 that as it is pulled through the system actually cams the first and second housing members 1120, 1122 apart not just allowing them to freely fall apart.

More particularly, and as discussed above with the various other embodiments, the suturing body 1114 includes a first housing member 1120 and a second housing member 1122 making up the suture housing 1124. The first and second housing members 1120, 1122 are hinged 1176 along one end thereof, with a spring 1178 biasing the first and second housing members 1120, 1122 to an open orientation (or are separate non-associated non-spring biased halves). The central connection member 1172 is positioned through the centerline of the first and second housing members 1120, 1122. In accordance with a preferred embodiment, the central connection member 1172 is secured to the first and second housing members 1120, 1122 through a member that is rigid enough to prevent inadvertent deployment of the system but can be broken or disengaged from the distal end of the suture housing 1124. When pulled, the central connection member 1172 releases the first and second housing member 1120, 1122 allowing the suture housing 1124 to fall open.

The opening of the suturing body 1114 upon removal of the central connection member 1172 is facilitated by including a camming member 1174 at the distal end 1180 of the central connection member 1172. The camming member 1174 is positioned and shaped such that it extends between the first and second housing members 1120, 1122 in a manner pushing the first and second housing members 1120, 1122 apart for removal of the needle 1128 or to provide other access to the internal structure of the suturing body 1114.

Figure 29:
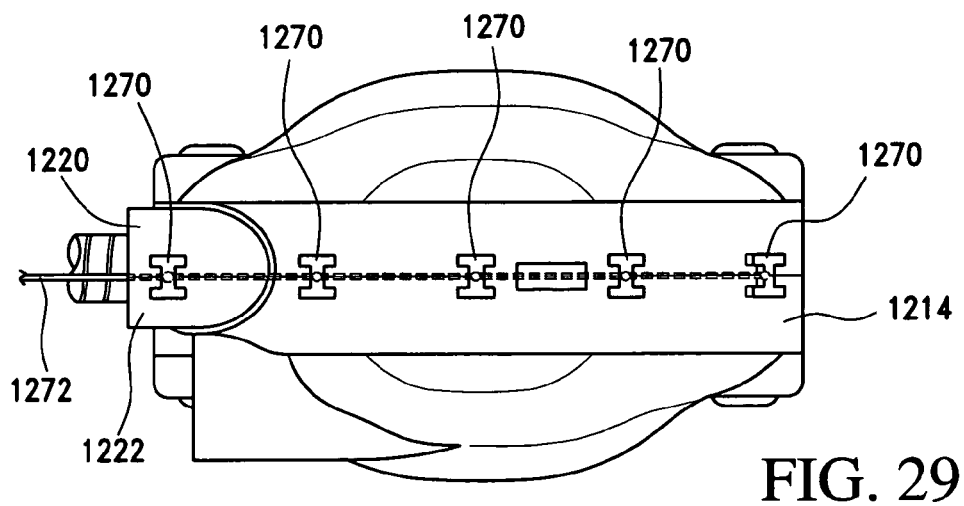
FIGS. 29, 30 and 31 are various views of a suturing body showing an alternate mechanism for selectively opening the suture housing.
Figure 30:
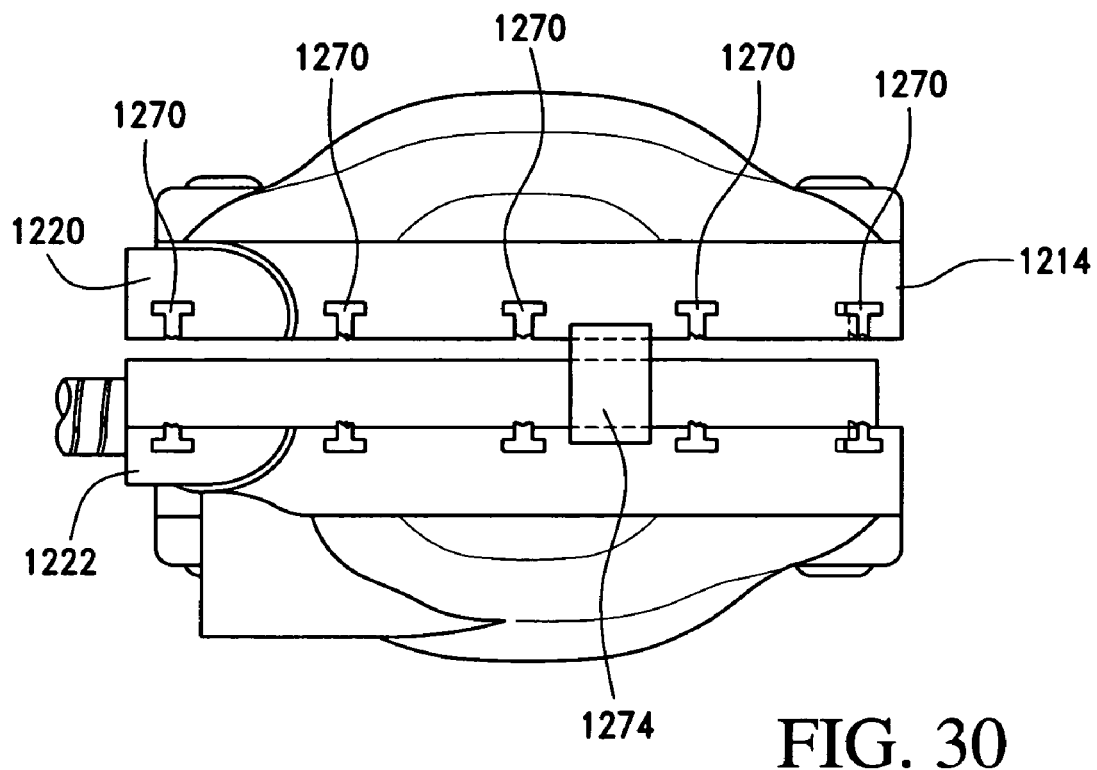
Figure 31:
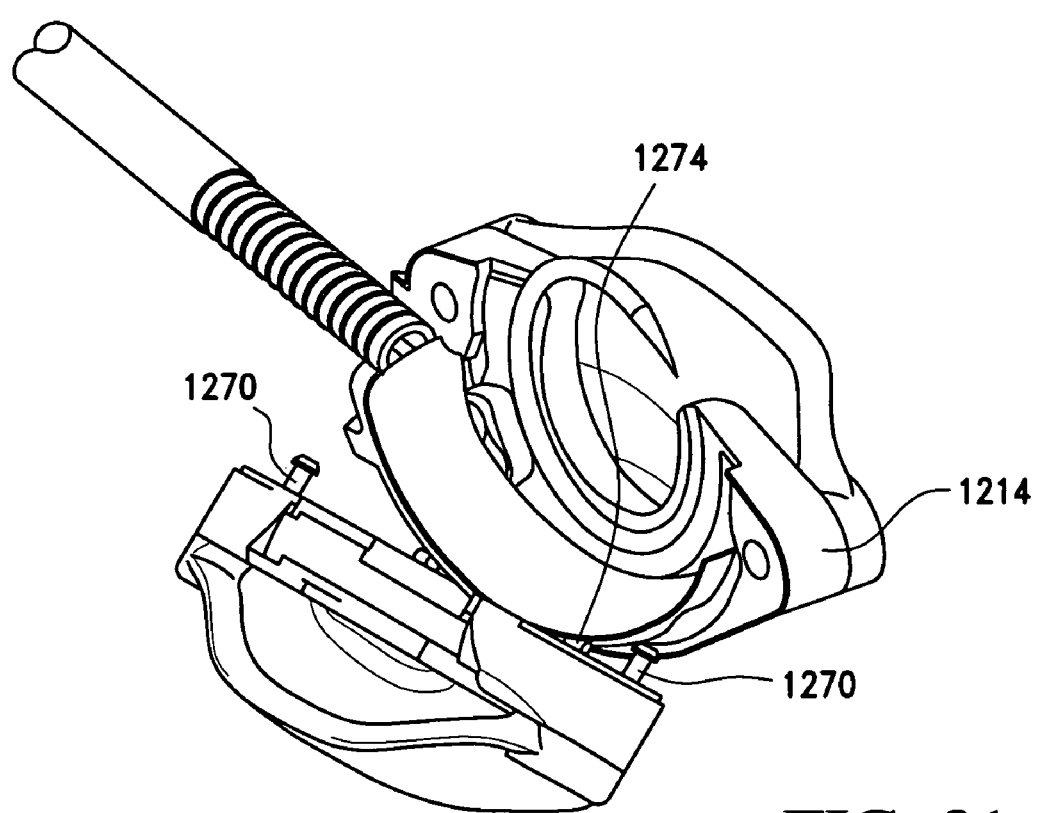

Referring to FIGS. 29, 30 and 31 yet a further embodiment of the present invention is disclosed. The embodiment employs a series of crushable interlocking clamps 1270 in the selective opening of the suturing body 1214. As with the cam pin set, the interlocking clamps 1270 hold the first and second housing members 1220, 1222 together during normal function. When a cable 1272 secured to the interlocking clamps 1270 is pulled, the interlocking clamps 1270 are crushed, unlocking the first and second housing members 1220, 1222 and allowing them to pivot open under the control of the spring biased hinge 1274.

In addition to the inclusion of a release structure for the housing structures described above, each of these embodiments is provided with a housing outer profile, shaped and dimensioned to permit limited closing of the suturing body as it is withdrawn from the stomach. In particular, the outer profile is rounded with a convex profile designed such that the first and second housing member are at least partially forced together when the suturing device is withdrawn through a trans-oral tube.

With the convex profile in mind, it is contemplated it may be desirable to hinge the first and second housing members along their proximal ends (see FIGS. 27 and 28). Either of the various release mechanism may be used in accordance with this embodiment. However, by positioning the hinge at the proximal end thereof the first and second housing members are directly connected to the shaft allowing them to be easily re-closed during extraction rather than having numerous loose parts free to move and fall wherever.

One of the challenges of a suturing apparatus offering a needle that moves through a continuous circular path is to identify to the user where the needle is in the stroke of the device as well as give the user a method to stop at the end of one full stroke around before starting the next stroke. Current imaging techniques allow doctors to visualize a variety of endoscopic procedures. However, the techniques and devices must be designed to permit visualization. In addition, and where visualization is important to completion of the technique, it is important that physical feedback be combined with the visual feedback to ensure redundancy in the event visualization is not possible.

As such, the present suturing apparatus is provided with a variety of indicators for both physical and visual identification of the procedure being performed. Briefly, and as will be discussed below in greater detail, the present endoscopic suturing device includes means for identifying the position of the needle along its path both locally in the surgical field and externally on the actuation mechanism. In addition, the endoscopic suturing device includes a secondary mechanism designed to stop the needle at the end of one full actuation to indicate to the user that it is the proper time in the sequence to re-position the device for subsequent actuations.

More particularly, and in accordance with the various embodiments described below, the surgical suturing apparatus includes a suture housing and a needle mounted within the suture housing for movement about an arcuate path. A drive assembly operably associated with the needle for controlling movement of the needle with a suture secured thereto about the arcuate path in a manner facilitating application of the suture to tissue. A mechanism is provided for determining the position of at least one of the distal end of the needle and the proximal end of the needle at all points along the arcuate path about which the needle moves.

Figure 32:
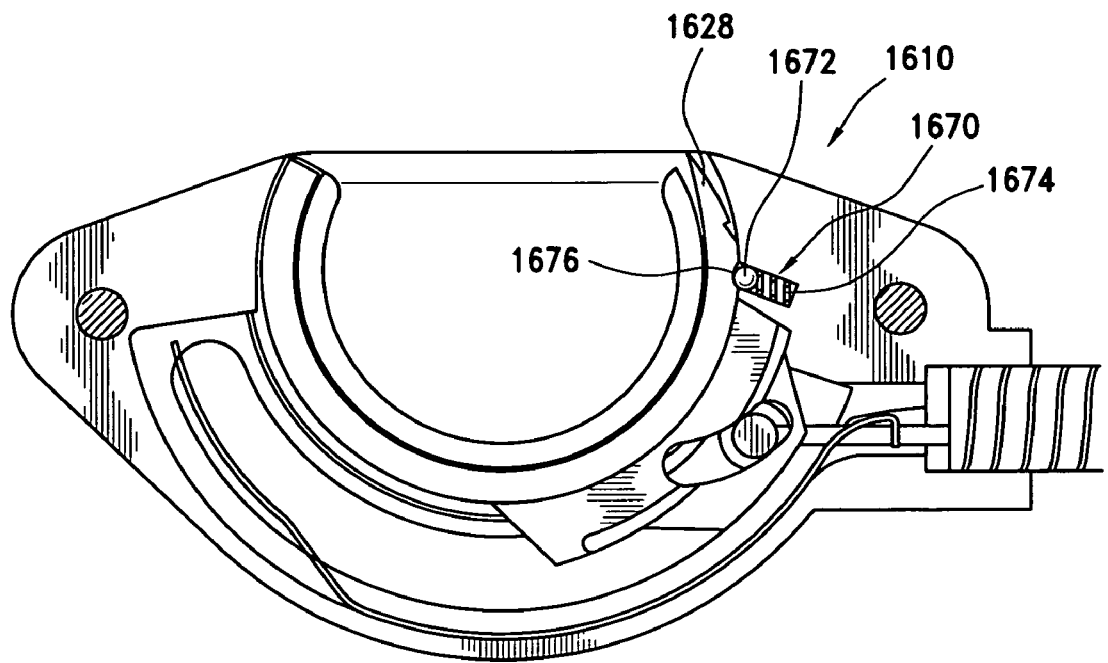
FIG. 32 is a cut away view of the suturing body showing a needle position indicating mechanism.

Referring to FIG. 32, the endoscopic suturing device 1610 includes a spring ball lock 1670 shaped and dimensioned to provide a physical indication of the needle 1628 position. In accordance with a preferred embodiment, a small ball bearing 1672 is spring 1674 biased into the path of the oncoming needle 1628 to stop its motion at the end of its travel. The ball bearing 1672 is mounted within the suturing body 1614 for access to and contact with the exterior surface of the needle 1628. The ball bearing 1672 is spring 1674 biased toward the exterior surface of the needle 1628. As such, when the needle 1628 is moved along its arcuate path and comes into contact with the ball bearing 1672, tactile feedback is provided to the user. The needle 1628 is provided with a recess 1676 along its exterior surface (preferably adjacent the tip of the needle, although multiple recesses may be employed at various locations along the length of the needle to provide physical indications of needle position). The recess 1676 is shaped and dimensioned to permit the ball bearing 1672 to seat therein when the needle recess 1676 comes into alignment with the ball bearing 1672 providing the user with tactile feedback of the needle positioned 1628. In accordance with a preferred embodiment, the ball bearing 1672 is positioned adjacent the entry point for the needle 1628 as it begins its throw loop and the recess 1676 of the needle 1628 is formed therealong at a position such that the operator is provided with additional tactile feedback that a complete needle loop is achieved.

It is contemplated the ball bearing may be used in combination with a camming mechanism to move it out of the path for the next stroke to occur or it can be used at a restricting force that only applies feedback to the user that the end of a stroke has been achieved, but can be overcome by the user though the application of more force.

Figure 33:
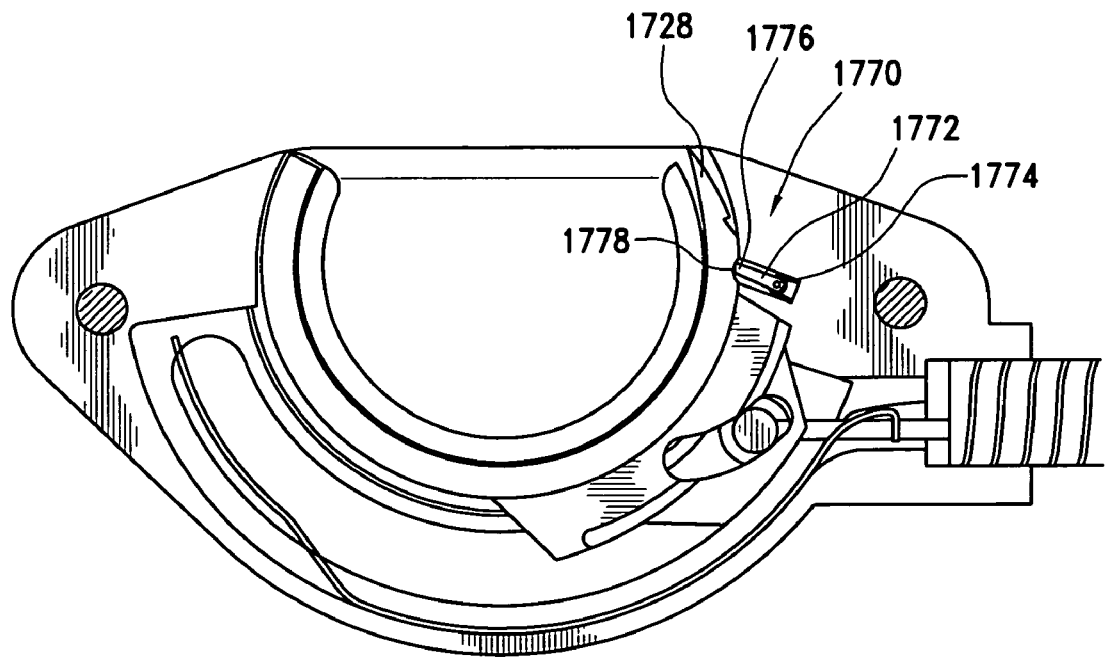
FIG. 33 is a cut away view of the suturing body showing an alternate needle position indicating mechanism.
Figure 34:
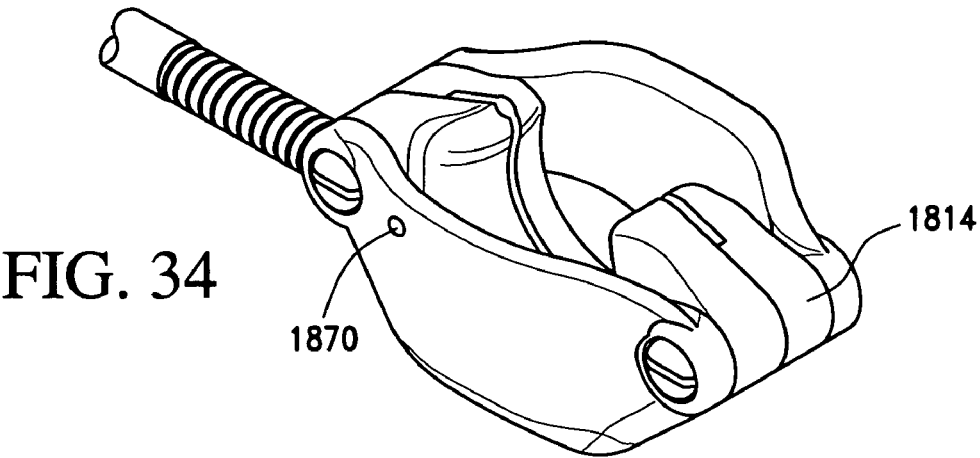
FIG. 34 is perspective view of a suturing body employing an alternate needle position indicating mechanism wherein an indicator pin is shown in its hidden position.
Figure 35:
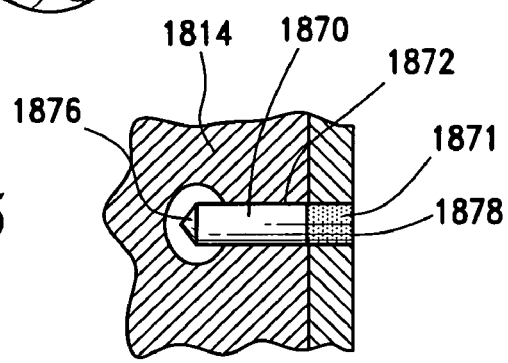
FIG. 35 is a cross sectional view of the needle position indicating mechanism shown in FIG. 34 with the indicator pin shown in its hidden position.
Figure 36:
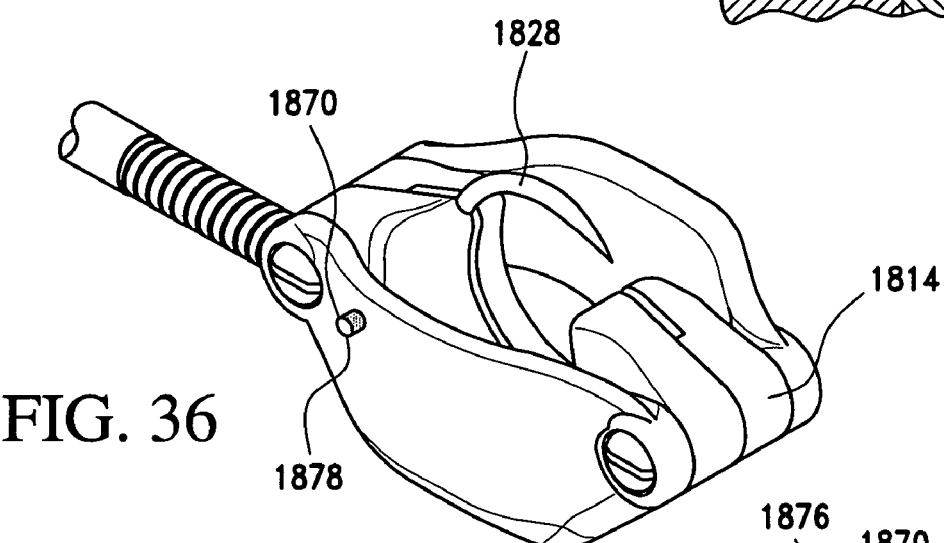
FIG. 36 is perspective view of the suturing body shown in FIG. 34 with the indicator pin in its exposed position.
Figure 37:
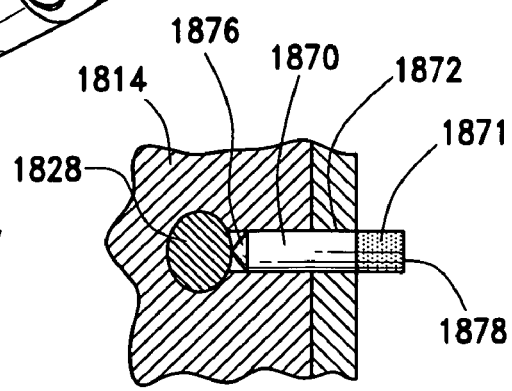
FIG. 37 is a cross sectional view of the needle position indicating mechanism shown in FIG. 36 with the indicator pin in its exposed position.

In accordance with an alternate embodiment, and with reference to FIG. 33, a spring ratchet pawl lock 1770 is oriented to interfere with movement of the needle 1728 for identifying needle 1728 position and the completion of a needle loop. More particularly, a pawl lock lever arm 1772 is secured along the forward end of the needle path for contact with the needle 1728 in a manner providing a physical indication as to the position of the needle 1728. The pawl lock lever arm 1772 is secured along the forward end of the needle path for contact with the needle 1728 in a manner providing a physical indication. The pawl lock lever arm 1772 includes a first end 1774 and second end 1776. The first end 1774 of the lever arm 1772 is pivotally secured to the suturing body 1714 of the suturing device 1710. The second end 1776 of lever arm 1772 extends toward and into contact with the exterior surface of the needle 1728. The lever arm 1772 is oriented such that when the needle 1728 is moved in a counter-clockwise direction, the lever arm 1772 slides over the exterior surface of the needle 1728.

However, and as with the prior embodiment, the exterior surface of the needle 1728 is provided with a recess 1778 along its exterior surface. The recess 1778 is shaped and dimensioned to permit the second end 1776 of the lever arm 1772 to seat therein when the needle recess 1778 comes into alignment with the second end 1776 of the lever arm 1772. As mentioned above, and in accordance with a preferred embodiment, the lever arm 1772 is positioned adjacent the entry point for the needle 1728 as it begins its throw loop and the recess 1778 of the needle 1728 is formed therealong at a position such that the operator is provided with a tactile feedback that a complete needle loop is achieved.

Referring to FIGS. 34, 35, 36 and 37, the suturing apparatus includes a pop-out indicator pin 1870. The pin 1870 is shaped and dimensioned to pop out the side of the suturing body 1814 when the needle 1828 is in its advanced position giving the surgeon visible feedback as to the needle 1828 position within the surgical site of the endoscope. Once the needle 1828 is fully advanced, the pin 1870 is spring biased to the hidden or in position indicating the suturing apparatus 1810 is ready for repositioning (see FIGS. 34 and 35). Visualization thereof is provided by coloring the exposed portion 1871 of the pin 1870 in a distinctive color to allow ready identification that the needle 1828 is positioned in a desired orientation.

More particular, the pin 1870 is spring biased within an aperture 1872 formed in the wall of the suturing body 1814. The pin 1870 is biased to a hidden position and includes a first end 1876 and a second end 1878. The first end 1876 is positioned for contact with the needle 1828 as it moves along its arcuate path, while the second end 1878 is positioned adjacent the outer surface of the aperture 1872 for movement between a hidden position and an exposed position. With this in mind, the second end 1878 of the pin 1870 is colored in a distinctive manner allowing ready visualization thereof.

Movement of the pin 1870 is facilitated by the movement of the needle 1828 into contact with the first end 1876 of the pin 1870. In particular, the first end 1876 of the pin 1870 is seated within the path of the needle 1828, although it is shaped and dimensioned to readily move once the needle 1828 moves into contact therewith (without unduly interfering with the movement of the needle as it makes its arcuate path).

In accordance with another embodiment and with reference to FIG. 38, the needle 1928 is colored to provide ready visualization thereof. More particularly, the needle 1928 is made with contrasting color to the surgical field to improve the visibility of the surgeon to identify where the needle 1928 is currently positioned. In accordance with a preferred embodiment, the tip 1970 is colored with the contrasting color to provide a ready identification the needle is exiting the suturing body.

Referring to FIG. 39, yet a further embodiment is disclosed. In accordance with this embodiment, the needle 2028 position is calibrated with an indicator 2070 secured at the handle of the suturing apparatus 2010. It is contemplated the indicator 2070 might be several hemispherical patterned lights, a dial indicator or other circular path indicator. In accordance with this embodiment, the suturing body 2014 is provided with one or multiple Hall effect sensors 2074 working in conjunction with the needle 2028 to provide the operator with an indication of the needle 2028 position. As the steel or magnetized steel needle 2028 passes adjacent the three sensors 2074 shown in FIG. 39 the system lights up the appropriate needle position indicator lights 2070 on handle 2072. Although Hall effect sensors are disclosed in accordance with a preferred embodiment of the present invention, other electronic means known to those skilled in the art could be used within the spirit of the present invention. For example, the sensors could be mechanical spring biased switches, or even extremely low voltage contact or inductance switches that make contact through needle itself making contact with both side of the switches (one placed on either side of the needle track).

Improved functionality of the present suturing apparatus is achieved by the provision of a mechanical attachment mechanism specifically adapted for attaching the vacuum chamber and suturing body to the end of the endoscope, allowing for rotational positioning of the endoscopic suturing device with respect to the endoscope. The various embodiments described below provide for a mechanical attachment mechanism that attaches the vacuum chamber and suturing body at the end of the endoscope, allowing for flexible positioning of the vacuum chamber and suturing body away from the endoscope to increase visibility of the pocket. In accordance with one embodiment described below, the mechanical attachment mechanism includes a flexible connection arm that collapses against the endoscope during insertion for a low profile insertion, but then springs away from the endoscope once in the body to improve visibility of the vacuum chamber and suturing body for positioning and suture deployment.

In accordance with another embodiment, the mechanical attachment mechanism attaches the vacuum chamber and suturing body to the end of the endoscope through the use of a detachable mechanism that can be removed and passed into a body cavity prior to the introduction of the endoscope, or for interchanging the suturing apparatus with another suturing body or even another endoscopic device. This could also allow for interchanging between a vacuum assist suture device and a non-assisted device.

The mechanisms provide for a unique method for access to a body cavity through either a natural orifice or a surgical initiated orifice. In particular, the present invention provides a method for inserting a suturing apparatus, or other surgical instrument, through a body orifice. The instrument has a low profile orientation and a deployed orientation which is larger than the size of the body orifice through which it is to be inserted. The method is achieved by coupling the instrument to an endoscope and placing the instrument in its low profile orientation, inserting the endoscope and the instrument through a natural orifice to a target position within a body while the instrument is in its low profile orientation, and actuating the instrument to it is deployed orientation. Finally, the instrument is returned to its low profile orientation and withdrawn from the body through the natural orifice.

Referring to FIG. 40, a first embodiment in accordance with the present invention is disclosed. In accordance with this embodiment, a scope attachment ring 2170 is secured about the distal end 2172 of the endoscope 2174 to which the present suturing apparatus 2110 is to be mounted. The attachment ring 2170 generally includes a ring body 2176 having parallel apertures 2178, 2180 respectively shaped for the receipt of the endoscope 2174 and the support shaft 2182 of the present suturing apparatus 2110 to which the suturing body 2114 and vacuum chamber 2146 are attached. With regard to the endoscope 2174, the first aperture 2178 is shaped for frictional engagement with the outer surface of the endoscope 2174 in a manner preventing rotation of the attachment ring 2170 relative to the endoscope 2174.

The second aperture 2180 is shaped and dimensioned for receiving the shaft 2182 of the suturing apparatus 2110, and in accordance with a preferred embodiment thereof, the second aperture 2180 is slightly larger than the shaft 2182 of the suturing apparatus 2110. In this way, the suturing apparatus 2110 may be rotated relative to the endoscope 2174 for improved access to tissue. Positioning of the suturing apparatus 2110 relative to the attachment ring 2170 is achieved by positioning abutment members 2184, 2186 along the shaft 2182 of the suturing apparatus 2110 on opposite sides of the attachment ring 2170. These members 2184, 2186 can be coupled to the shaft 2182 via screw threads during manufacturing, pressed into place during manufacturing or be molded as part of the attachment ring itself. In this way, the suturing apparatus 2110 may be freely rotated relative to the endoscope 2174 while the suturing apparatus 2110 is substantially prevented from longitudinal movement relative thereto.

Figure 41:
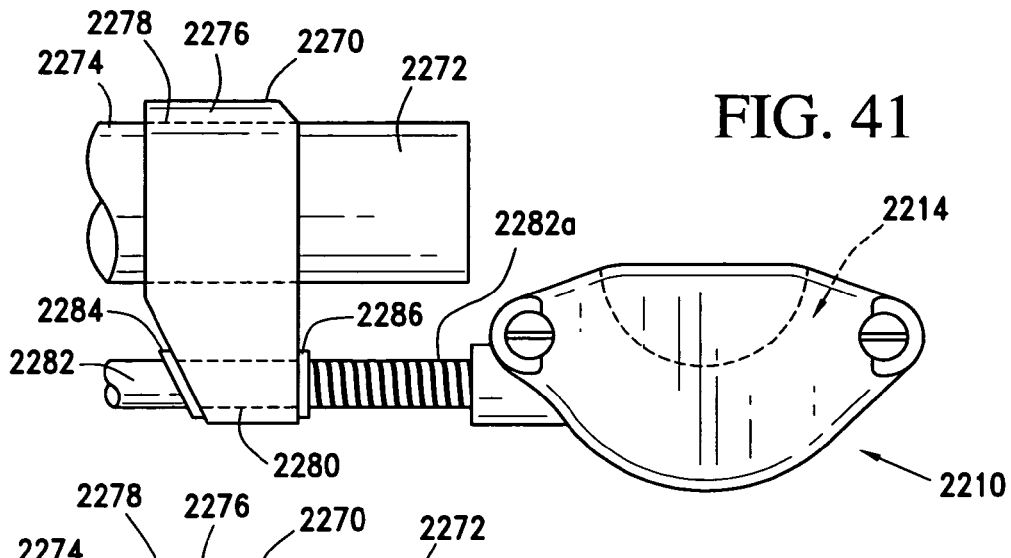
Figure 42:
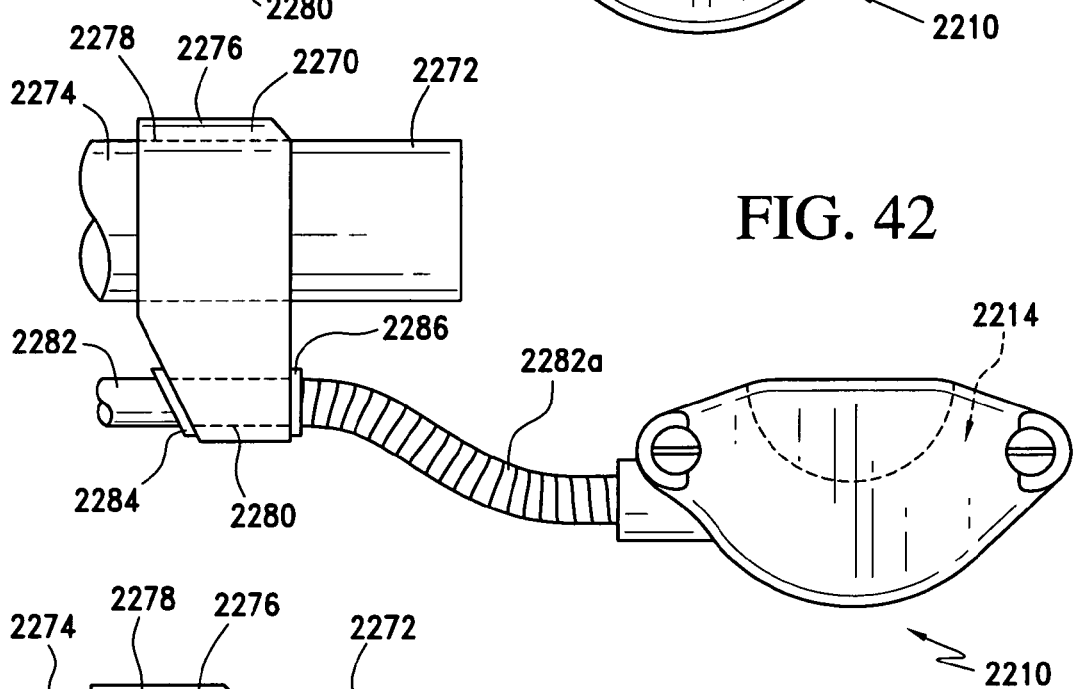
Figure 43:
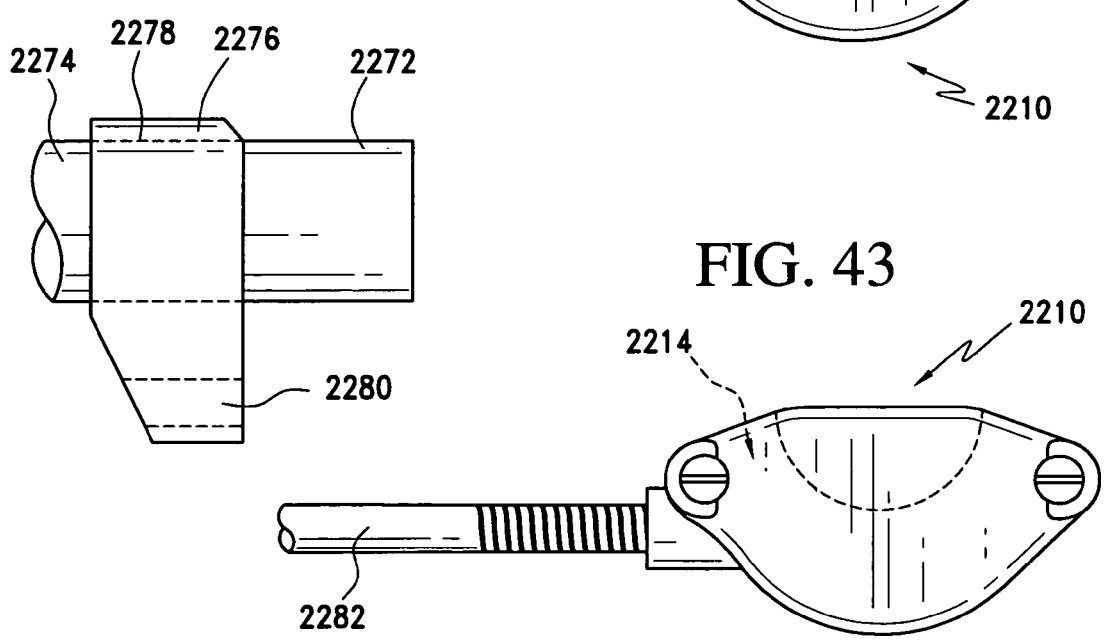
Figure 49:
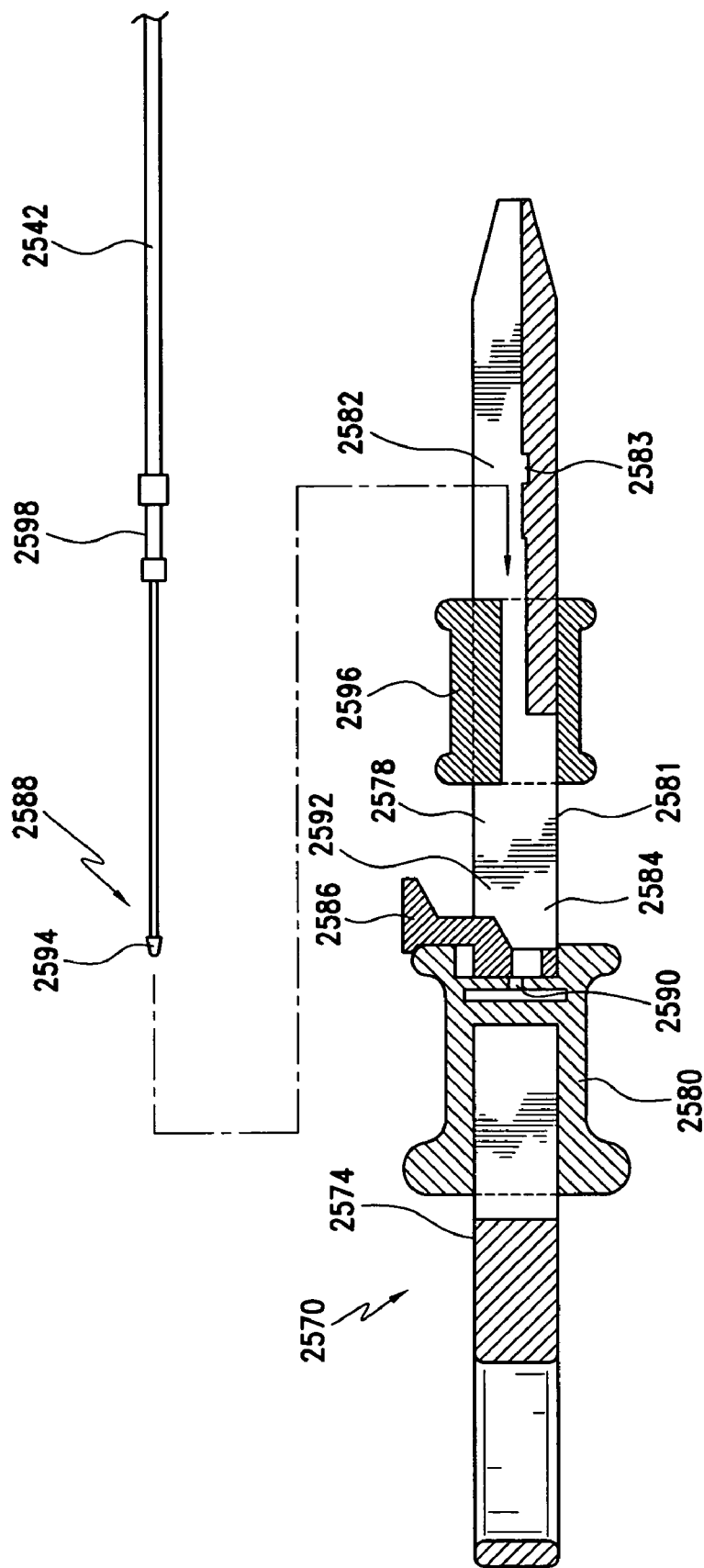

In accordance with another embodiment and with reference to FIGS. 41, 42 and 43, an endoscope attachment ring 2270 similar to that described above is secured about the distal end 2272 of the endoscope 2274 to which the present suturing apparatus 2210 is to be mounted. The attachment ring 2270 generally includes a ring body 2276 having parallel apertures 2278, 2280 respectively shaped for the receipt of the endoscope 2274 and the present suturing apparatus shaft 2282. With regard to the endoscope 2274, the aperture 2278 is shaped for frictional engagement with the outer surface of the endoscope 2274 in a manner preventing rotation of the attachment ring 2270 relative to the endoscope 2274.

As for the second aperture 2280 receiving the shaft 2282 of the suturing apparatus 2210, and in accordance with a preferred embodiment thereof, the second aperture 2280 is approximately the same size as the shaft 2282 of the suturing apparatus 2210. In this way, the suturing apparatus 2210 is prevented from rotating relative to the endoscope 2274 allowing for the elastic deployment off the axis of the endoscope 2274 to permit better visualization. Positioning of the suturing apparatus 2210 relative to the attachment ring 2270 is achieved by positioning abutment members 2284, 2286 along the shaft 2282 of the suturing apparatus 2210 on opposite sides of the attachment ring 2270. In an alternate embodiment the fit between the endoscope attachment ring and the elastic arm could be a loose fit as discussed above with regard to the embodiment shown in FIG. 40 permitting it to be freely rotated relative to the endoscope while the endoscopic suturing device is substantially prevented from longitudinal movement relative thereto.

Improved access of the suturing apparatus is further facilitated by manufacturing the shaft 2282 distal from the second aperture 2280 of the attachment ring 2270 from a flexible material that is biased to a position removed from the endoscope 2274. In this way, the suturing apparatus 2210 may be held close to the endoscope 2274 during insertion, reducing the profile of the structure being inserted trans-orally, while allowing for movement of the suturing apparatus 2210 away from the endoscope 2274 when the suturing apparatus 2210 reaches its desired location.

More particularly, the portion of the shaft 2282a providing for flexing of the suturing body 2214 away from the endoscope 2274 is an elastomer lever arm designed to move the suturing apparatus 2210 off axis from the endoscope 2274 in a manner improving visualization of the suturing apparatus 2210 and its usage while still allowing it to deflect against the endoscope during insertion and extraction, reducing its overall profile during these activities.

In accordance with an alternate embodiment of the present invention and with reference to FIGS. 41a and 42a, the attachment ring 2270a may be constructed with a connection member 2283a extending distally from second aperture 2280a. The connection member 2283a is an elastomer lever arm designed to move the suturing apparatus 2210a, with the shaft 2282a thereof extending through the connection member 2283a off axis from the endoscope 2274a in a manner improving visualization of the suturing apparatus 2210 and its usage while still allowing it to deflect against the endoscope 2274a during insertion and extraction, reducing its overall profile during these activities.

As briefly mention above, the connection member 2283a is shaped and dimensioned to fit about the shaft 2282a of the suturing apparatus 2210a. The connection member 2283a is constructed of a resilient material and is biased to a position removed from the endoscope 2274a. In this way, the connection member 2283a with the shaft 2282a of the suturing apparatus 2210 extending therethrough may be held close to the endoscope 2274a during insertion, reducing the profile of the structure being inserted trans-orally. However, once the suturing body 2214a is positioned within the body cavity, the connection member 2283a is released, allowing it to extend away from the endoscope 2274a. Because the shaft 2282a of the suturing apparatus 2210 is positioned within the connection member 2283a, the shaft 2282a and the suturing body 2214a are moved away from the endoscope 2274a as the connection member 2283a moves away from the endoscope 2274a.

In addition to the various embodiments discussed above and with reference to FIGS. 44, 45 and 46, it is contemplated a guidewire introducer 2470 for a suturing apparatus 2410 may be employed. Such a device is used in combination with a detachable vacuum chamber 2446 and suturing body 2414 detailed above. The distal end components, that is, the vacuum chamber 2446 and the suturing body 2414 are passed, for example, through the oral cavity in advance of the endoscope 2472 and subsequently attached to the endoscope attachment ring 2474 via a guide wire 2470 which is pulled through a support shaft 2476 in a manner drawing the suturing body 2414 and vacuum chamber 2446 onto the support shaft 2476. The endoscope 2472 itself can be used to advance the detached vacuum chamber 2446 and a suturing body 2414 down the oral cavity. The pre-positioned guide wire 2470 within the working channel of the endoscope 2472 is terminated at its distal end 2471 by connection to the vacuum chamber 2446 and suturing body 2414. Once passed into the stomach, the vacuum chamber 2446 and suturing body 2414 are pulled back into attachment to the distal end of the endoscope 2472 and onto a support shaft 2476 by pulling the suturing body 2414 and vacuum chamber 2446 into engagement with the endoscope 2472 through the action of the guidewire 2470 to which the vacuum chamber 2446 and suturing body 2414 are connected. This allows for use of a vacuum chamber 2446 and suturing body 2414 that are laterally and thickness wise larger than could be passed in fixed attachment to the endoscope during insertion.

As an alternative embodiment, the vacuum chamber can be interchangeable used with non-vacuum equipment that looks similar or identical to the vacuum version, but does not utilize the vacuum to position the tissue and merely relies upon placing the chamber adjacent to the tissue to be sutured. This drastically reduces the bite size, but also reduces the possible trauma to the tissue that vacuuming the tissue into the pocket may cause.

In particular, there are some procedures that would preferably be used without a vacuum assist to pull the tissue into the vacuum chamber, but rather would merely throw the suture with minimal tissue bite depth. There are even clinical situations where the vacuum could induce damage to the tissue. An interchangeable vacuum chamber that has a differing cavity depth and profile could be used with the suturing apparatus without a vacuum assist.

A quick handle disconnect is also contemplated in accordance with present invention and is shown with reference to FIGS. 47, 48, 49, 50 and 51. This feature may be used in combination with or separately from the guidewire introducer as described above. Briefly, this embodiment employs a suture housing 2524, a needle 2528 mounted within the suture housing 2524 for movement about an arcuate path, a drive assembly operably associated with the needle 2528 for controlling movement of the needle 2528 with a suture secured thereto about the arcuate path in a manner facilitating application of the suture to tissue, a handle 2570, an elongated flexible member, for example, a drive cable 2542 having a distal end attached to the suture housing 2524 and a proximal end attached to the handle 2570, and a mechanism for releasing and reattaching the handle 2570 to the flexible member 2542.

The utilization of a quick handle disconnect facilitates distal detachment and pre-passing of the suturing apparatus 2510 through the selective attachment and detachment of the handle 2570 from the flexible drive cable 2542 to which the suturing body 2514 and vacuum chamber 2546 are connected. In accordance with this embodiment, the drive cable 2542 may function much like the guidewire previously discussed in allowing one to pass the suturing body 2514 and the vacuum chamber 2546 into position prior to complete assembly. This improvement allows one to pre-pass the suturing apparatus 2510 from the distal end of the endoscope in manner reducing the required profile because the suturing apparatus 2510 is positioned distal of the endoscope during passage thereof rather than passing the suturing apparatus 2510 from the proximal end of the endoscope in a manner increasing the required passageway since the profile must accommodate both.

More particularly, the handle 2570 is composed of a handle body 2574 in which the drive cable 2542 is releasably secured for actuation. With this in mind, the handle body 2574 includes a central passageway 2578 in which the drive cable 2542 is stored and mounted. The handle body 2574 is composed of a central grip 2580 and a slide member 2581 that moves relative to the central grip 2580 in a manner discussed below in greater detail. The central passageway 2578 includes a first open end 2582 and a second closed end 2584. Adjacent the second closed end 2584 is a spring loaded trigger lock 2586 secured to the central grip 2580. The trigger lock 2586 is shaped and dimensioned to engage a protrusion 2594 (for example, a bullet nose tip) along the proximal tip 2588 of the drive cable 2542. In this way, the proximal tip 2588 of the drive cable 2542 is mounted within a recess 2590 in the proximal end 2592 of the passageway 2578 and within the central grip 2580 (for centering thereof), and the trigger lock 2586 is moved downward into engagement with the protrusion 2594 for maintaining the drive cable 2576 within the handle body 2574. When it is desired to remove the handle 2570 from the drive cable 2578, one need only actuate the trigger lock 2586 to its release position and the handle body 2574 may be freely removed from the drive cable 2542. Retention of the drive cable 2542 within the handle body 2574 is further facilitated by the inclusion of a locking slide 2596 along the slide member 2581. The locking slide 2596 frictionally interacts with a collar 2598 formed on drive cable 2542 for retention of the handle body 2574 thereon.

In practice, the distal end of the drive cable 2542 is inserted within the passageway 2578 formed in the slide member 2581. The drive cable 2542 is inserted to such a point that the collar 2598 of the drive cable 2576 is aligned with openings 2583 formed along the slide member 2581. At this point, the locking slide 2596 is slid along the slide member 2581 and is moved over the collar 2598 into engagement therewith. The drive cable 2542 is, at this point, secured to the slide member 2581. The slide member 2581 is then moved proximally relative to the central grip 2580 until the proximal end 2588 of the drive cable 2542 is seated within the recess 2590 formed in the central grip 2580. The trigger lock 2586 is then spring actuated to engage the protrusion 2594 at the proximal tip 2588 of the drive cable 2542 for securing it to the central grip 2580 and the handle body 2574.

Once the handle 2570 is secured to the drive cable 2542, release thereof is achieved by reversing the attachment steps discussed above. In particular, the trigger lock 2586 is rotated forward to permit release of the protrusion 2594 from within the recess 2590 of the central grip 2580.

As discussed above, the present handle 2570 allows for actuation of the drive cable 2542 in a manner operating the present suturing apparatus 2510. In particular, relative movement of the central grip 2580 and the slide member 2581 while the drive cable 2542 is seated within the central grip 2580 causes actuation thereof permitting the drive assembly to function in the manner described above.

Although the selectively releasable connection is described above with reference to the handle of a suturing apparatus, it is contemplated the releasable connection could similar be applied in the selective connection of the suturing body to the shaft connecting the suturing body to the handle. In this way, one could selectively connect the suturing body to the shaft once the suturing body is positioned within the body cavity and ready for use in the application of a suture to tissue.

The vacuum pressure available in different operating room suites varies greatly from location to location. Improvements to the vacuum chamber minimizing the necessary vacuum required have been discussed above. However, such structural changes might not be sufficient to ensure the present endoscopic suturing apparatus can be used in any location. The embodiments detailed herein are improvements to the handle to locally increase the vacuum in the vacuum chamber.

Each of these embodiments provides an endoscopic instrument, for example, a suturing apparatus, adapted for use with an endoscope. The instrument includes an elongated tube having a distal end and a proximal end, an end effector, for example, the suturing body of the suturing apparatus, attached to the distal end of the elongated tube, and a handle attached to the proximal end. The handle includes a mechanism for attaching the instrument to a first vacuum source. The handle further includes a second vacuum source integral with the handle for amplifying the first vacuum source, whereby the first and second vacuum sources combine to operate the end effector.

Figure 64:
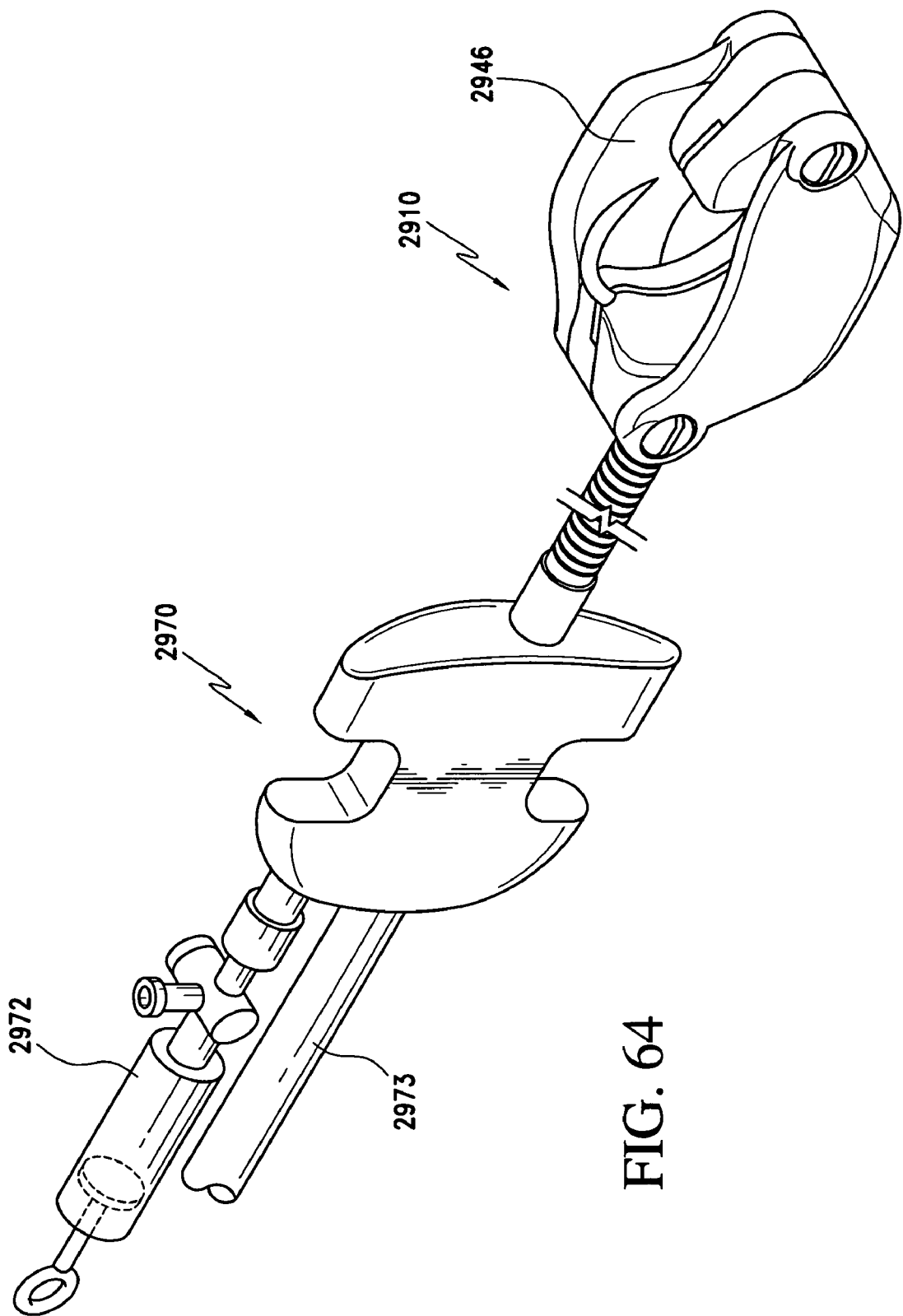

Referring to FIG. 64, this problem is addressed by the provision of a syringe based handle vacuum assist device 2970. In accordance with a preferred embodiment of the present invention, a syringe mechanism 2972 is placed in parallel to the main vacuum attachment 2973 to the suturing apparatus 2910. This allows the normal operating room vacuum source to be used to accomplish as much as it is capable of and, if additional vacuum is still necessary to get a good tissue bite, the syringe mechanism 2972 can be pulled by the surgeon to increase the vacuum in the vacuum chamber 2946. Since the normally available vacuum source of the operating room is the primary mechanism for drawing tissue into the vacuum chamber 2946, the volume necessary in the syringe mechanism 2972 is minimized as the tissue will already be engaged in the vacuum chamber 2946, although not to its full depth. An additional benefit of this method of assisting an operating room vacuum source is that fluids will have already been evacuated from the vacuum chamber 2946 by the normal or primary operating room suction means and the syringe mechanism 2972 will not be filled with bodily fluids.

In accordance with another embodiment, and with reference to FIG. 65, a battery 3071 powered multi-stroke vacuum assist device 3070 for suction actuation is provided. The vacuum assist device 3070 includes a rotary fluid pump 3072 (lobe pump, gear pump, peristalsis pump, etc.) to be used in a multi-stroke fashion to increase the maximum volume of gasses that can be extracted from the vacuum chamber after the primary vacuum source of the operating room is completely engaged. This has the same benefits of the syringe based system, but provides for the ability to exchange a greater volume of gas.

Similarly, and with reference to FIG. 66, a battery 3171 operated disposable vacuum pump 3170 is associated with a disposable deployment handle 3172 used in conjunction with the present suturing apparatus 3110. Like the mechanical multi-stroke mechanism detailed above, a battery operated, motor driven, disposable fluid pump 3170 is included in the handle 3172 to supplement the vacuum available from the operating room.

Figure 67:
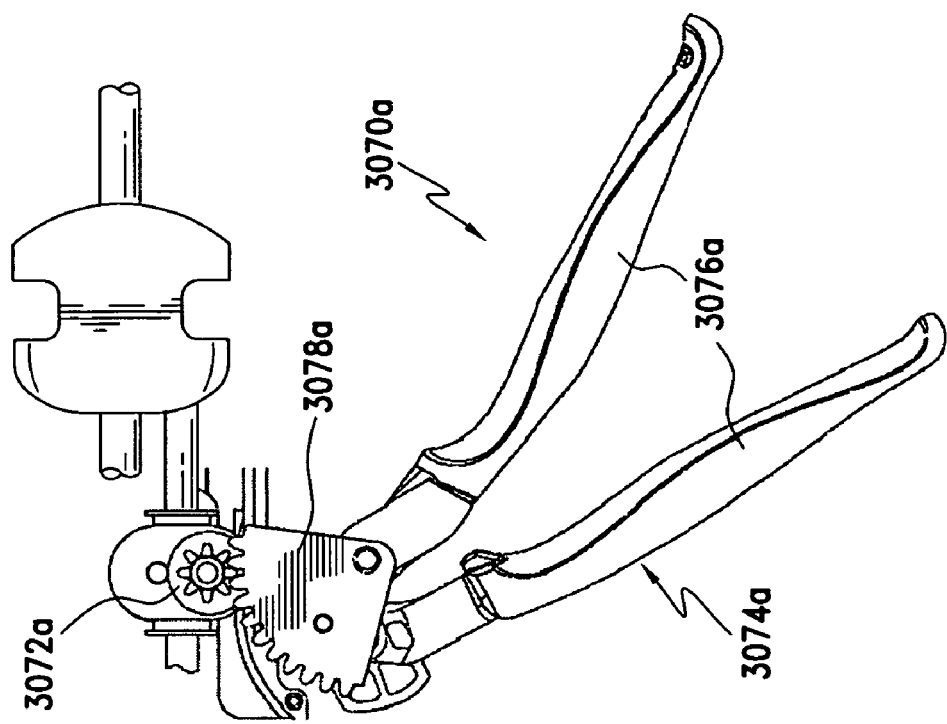

Although FIGS. 65 and 66 disclose systems that are automatically actuated to create a secondary vacuum source, FIG. 67 discloses a trigger actuated system 3070*a*. The trigger 3074*a* employs trigger handles 3076*a* in conjunction with a gearing arrangement 3078*a* to drive a fluid pump, for example, a single lobe fluid pump 3072*a*. As with the prior embodiments, actuation of the trigger 3074*a* and the fluid pump 3072*a* increases the maximum volume of gases that may be extracted from the vacuum chamber after the primary vacuum source of the operating room is completely engaged. This has the same benefits of the syringe based system and the automated system, but provides for manual actuation offering a surgeon greater control.

Figure 68:
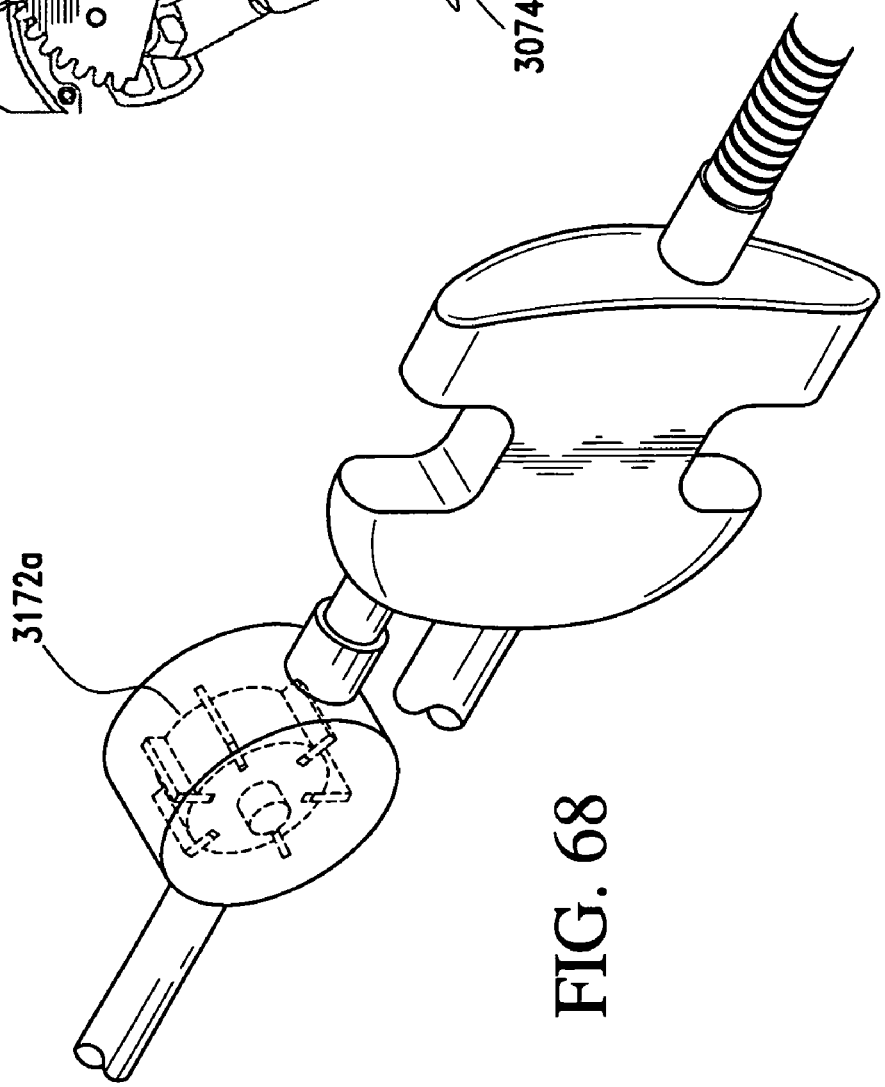

It is further contemplated the vacuum assist may be created via a squeeze bulb with a one-way valve or a bellow mechanisms with a one-way valve or a secondary suction line. In addition, an idling vane 3172*a* could also be incorporated to intermittently provide vacuum assist (see FIG. 68).

As discussed above, visualization of the suturing apparatus 3510 is often critically important to the proper use thereof. With this in mind, the suturing apparatus 3510 may be modified to improve imaging thereof. In particular, the apparatus 3510 includes a flexible member 3516, for example, a support shaft or endoscope, having a distal end attached to a suturing body 3514 for insertion of the suturing body 3514 through an orifice and into a body cavity. The suturing body 3514 includes a suture housing 3524 in which a needle 3528 and drive assembly are housed for movement of the needle 3528 with a suture secured thereto about an arcuate path facilitating application of the suture to tissue. A non-visible spectrum sensing member 3570 is associated with the suturing body 3514 for communicating a parameter of the procedure to a visual display 3572. In accordance with a preferred embodiment, the non-visible spectrum sensing member is wirelessly linked to the visual display.

Figure 83:
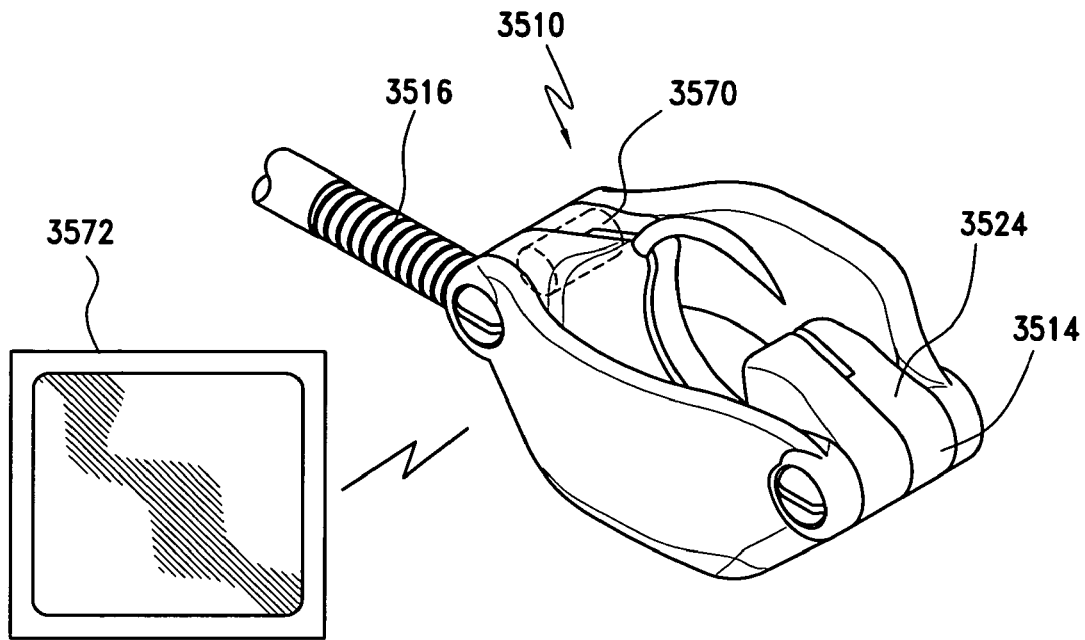
FIGS. 83 and 84 are perspective views of a suturing apparatus incorporating an imaging device within the suturing body.
Figure 84:
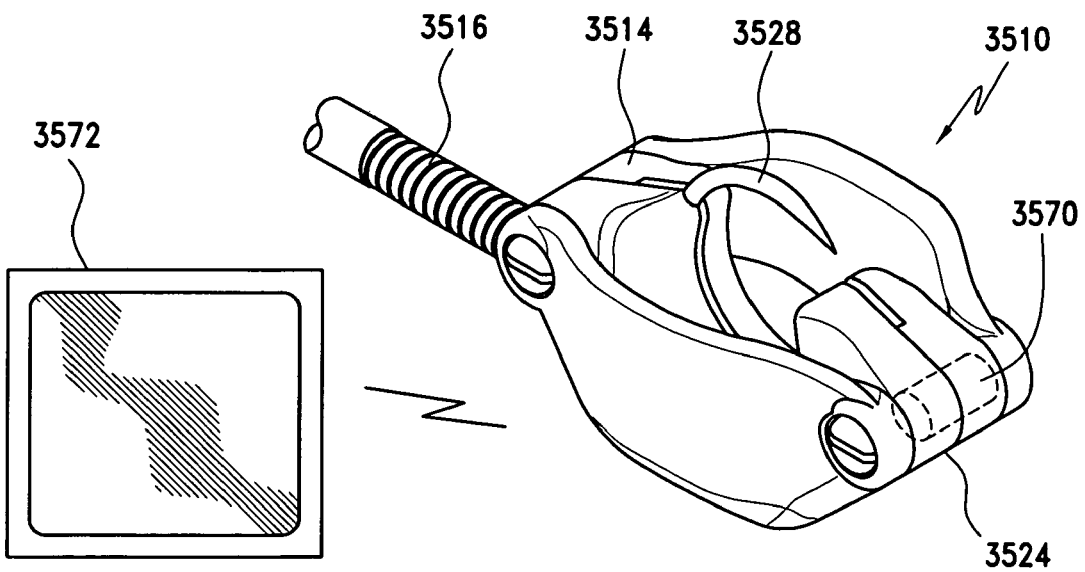

For example, it is contemplated the suturing apparatus 3510 may be modified through implementation of ultrasonic transducers 3570 in the suturing body 3514 (see FIGS. 83 and 84). Similarly, the suturing apparatus 3510 may be modified by the inclusion of a magnetic resonance imaging source transducer based within the suturing body or vacuum chamber to image the local suture site. Further, it is contemplated the endoscopic suturing device may be modified with the inclusion of an infrared based imaging sensor within the suturing body or vacuum chamber to evaluate blood flow to the sutured area post suture deployment or to identify blood rich areas in the interior lining pre-suture deployment for blood flow visualization. The endoscopic suturing device may also include Laser Doppler, oxygen, or carbon dioxide based sensors located within the suturing device to evaluate the blood flow characteristics before or after the suture line is deployed.

These various visualization techniques provide for non-visible (outside the normal visible spectrum) imaging integrated into the suturing apparatus to improve the visualization of the site during suturing. As mentioned above, the contemplated mechanisms could be ultrasonic, infrared, MRI, Laser Doppler, oxygen and carbon dioxide sensors or other sensor system. In addition, the sensors provide for tissue penetration visualization means for viewing the location of surrounding organ geometry and Tissue penetration visualization means for viewing the suture deployment depth and bite size.

Figure 85:
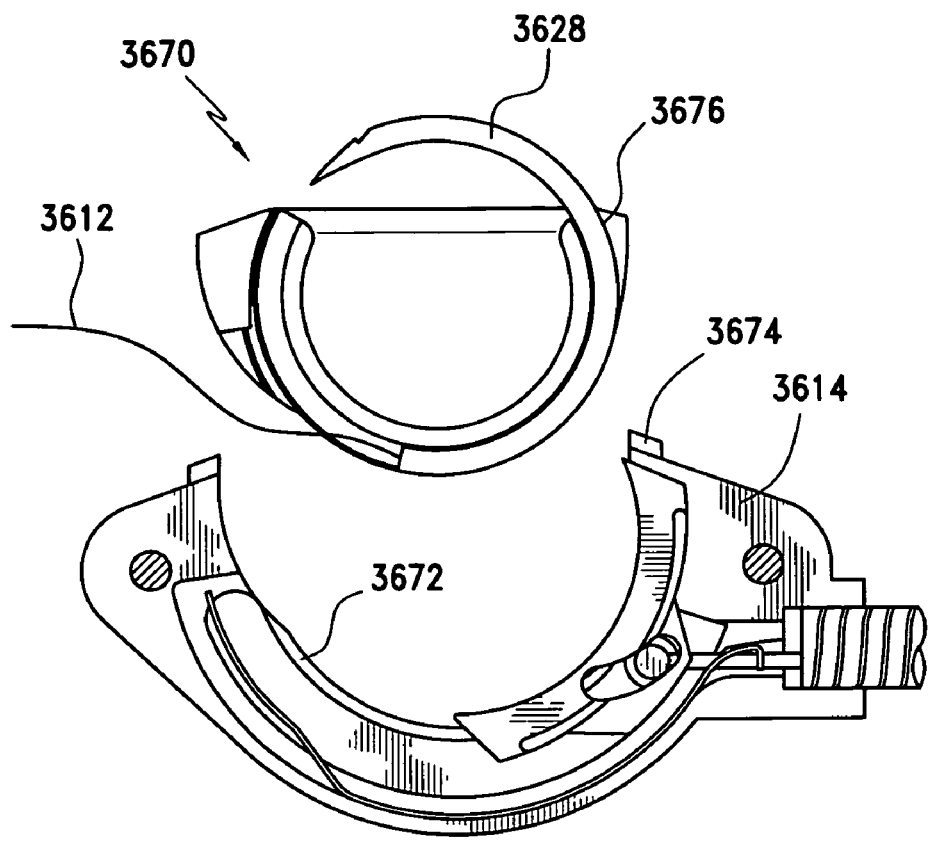
FIG. 85 is a cut away view of the suturing body showing a cartridge mechanism for utilization therewith.

Referring to FIG. 85 a cartridge 3670 for the loading of needles 3628 and sutures 3612 of different sizes is disclosed. In accordance with a preferred embodiment, a reloadable cartridge 3670 is capable of loading differing size needles 3628 and differing size sutures 3612. The cartridge 3670 is shaped and dimensioned for ready attachment within the channel 3672 in which the needle 3628 is mounted in accordance with the embodiment disclosed. In particular, the suturing body 3614 is provided with a cover 3674 providing access to and closure of the channel 3672 in which the needle 3628 is located. Through the implementation of a cartridge based system the detachable cartridge 3670 can be removed and replaced with a fresh needle 3628 and suture 3612 or even a different size of needle or suture.

In accordance with a preferred embodiment, the needle 3628 is supported in a track member 3676, which readily seats within the channel 3672 to create an assembly substantially similar to that disclosed above with reference to FIGS. 3 to 10.

Figure 86:
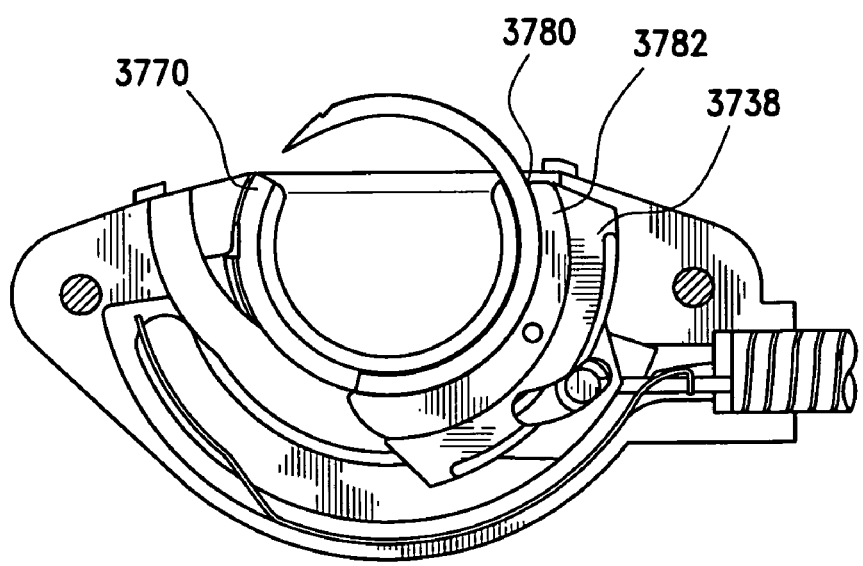
FIG. 86 is a cut away view of the suturing body showing a cartridge mechanism having a smaller needle.

The cartridge based system may further be adapted to allow for the adjustment of the needle size through a simple cartridge replacement. In particular, and with reference to FIG. 86, the track 3780 of the cartridge 3770 is provided with a spacer wedge 3782 taking up the space lost with the inclusion of a smaller needle 3728. The spacer wedge 3782 is shaped and dimensioned to interact with the friction camming member 3738 in a manner allowing the suturing apparatus 3710 to operate in accordance with this spirit of the present invention.

Figure 87:
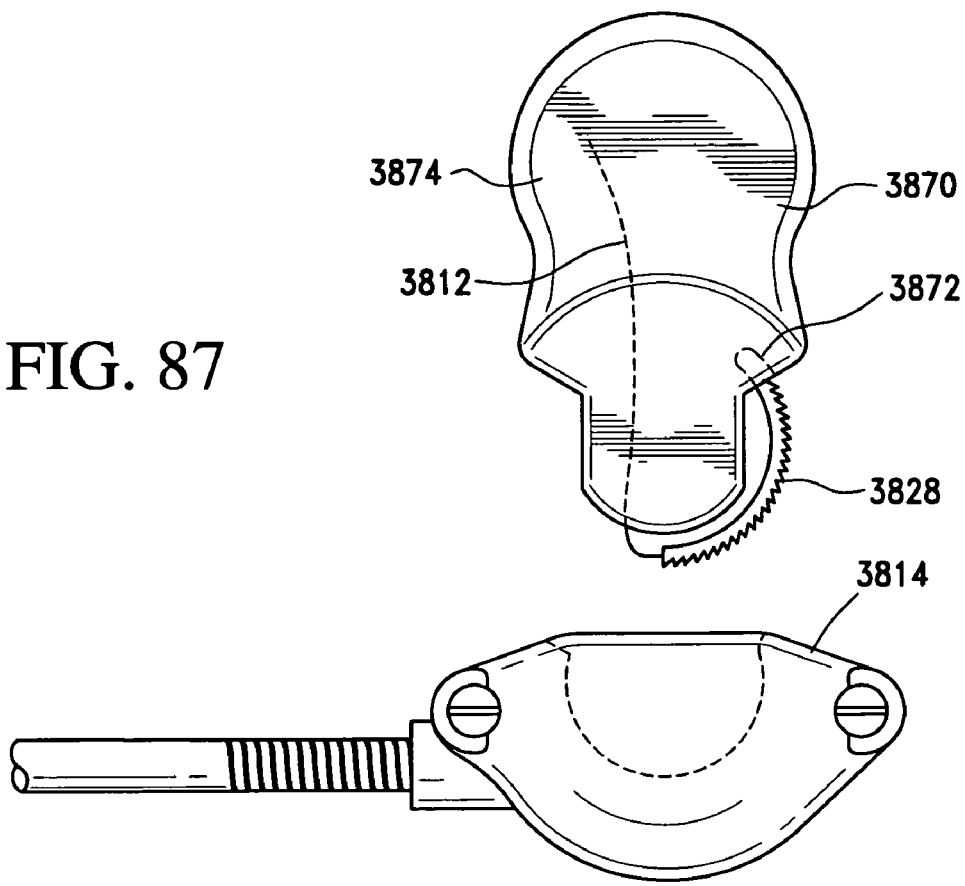
FIGS. 87 and 88 are side views showing a needle loading mechanism in accordance with the present invention.
Figure 88:
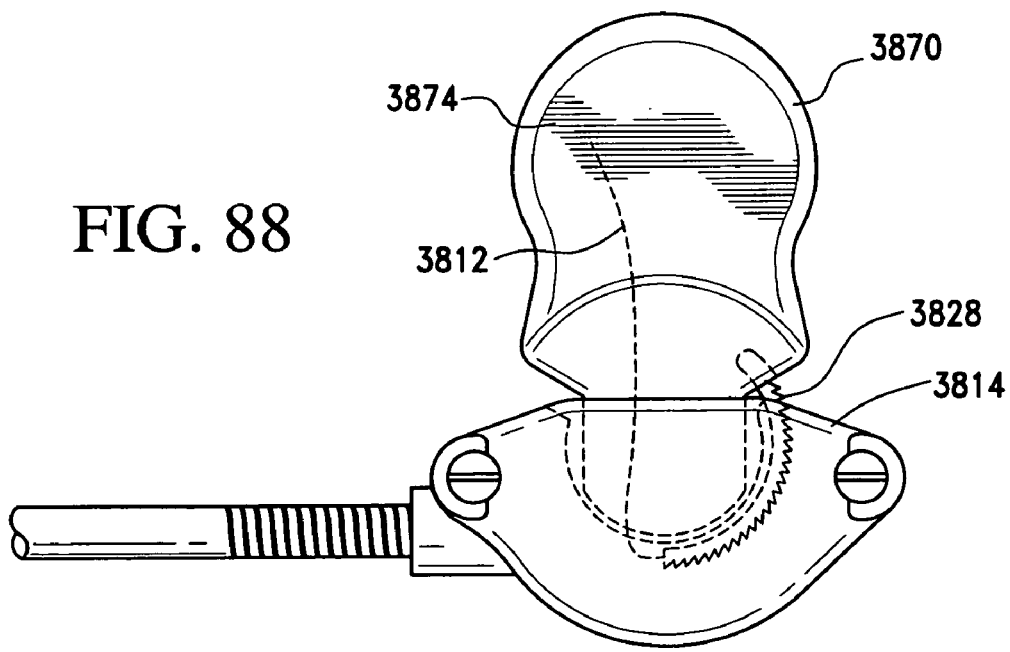

While a cartridge based system is disclosed above, the suturing body of the suturing apparatus could be designed to permit simple replacement of the needle alone. Referring to FIGS. 87 and 88 this is achieved through the provision of an openable suturing body 3814. Rather than having a cartridge based reload, this embodiment for reloading merely controls the needle 3828 and suture 3812, making quick loading of a device without a removable section. The needle 3828 would be coupled to the reloader 3870 via a clamp 3872 that could be released or easily broken and the suture 3812 would be maintained on the handhold section 3874 of the reloader 3870. This would facilitate manipulation of the needle 3828 without touching it directly and would provide some form of suture management prior to being loaded into the suturing apparatus 3828.

One of the difficulties in performing endoscopic procedures is efficiently and securely forming knots once the suturing is completed. It is desired the two ends, or leads, of the suture could be pulled tight simultaneously and a knotting element could then be used to tighten the adjacent ends. This would maximize the number of stitches that could be thrown before the suture needs to be cinched down since both ends of the suture could be pulled in a manner equally cinching from both ends of the suture.

In accordance with a preferred embodiment of the present invention, a suture is secured by inserting the suture through a passageway into the body of a patient. The suture is then thrown into and back out of tissue. Finally a knot is tied along the length of suture in a manner securing the suture in place. The knot is then fused through the application of energy mechanically linking the first and second leads of the suture forming the knot. In accordance with a preferred embodiment, the term "fusing" is meant to refer to any technique by which the suture and/or knotting element are brought together in a manner whereby their material components are fixedly connected.

In accordance with preferred embodiments of the present invention, tying of the knot is achieved in a variety of manners, wherein the first and second leads are entangled in a manner holding the leads relative to each other. As such, those skilled in the art will appreciate that a variety of knotting techniques may be used in accordance with the present invention. For example, a traditional tying technique may be used wherein the first and second leads of the suture are tied in a mechanical knot which is subsequently fused.

In accordance with a preferred embodiment, and with reference to FIG. 62, a suture hooking device 2710 is disclosed for tying first and second leads 2730, 2732 of a suture together. The hooking device 2710 utilizes two parts to lock the suture together in a cap like fashion. The advantage to this method is that the cap 2712 has two extension arms 2714, 2716 that allow it to be twisted about its axis winding the suture 2718 mid-lengths onto its shaft. The cap 2712 would then be crushed into the outside collar 2720 locking the suture ends 2718. This would allow for fine tensioning just prior to locking the suture together.

More particularly, the suture hooking device 2710 includes an outside collar 2720 and a cap 2712 shaped and dimensioned to fit within the outside collar 2720. The outside collar 2720 is generally cylindrical and includes an open upper edge 2722 and a close base 2724. The cap 2712 includes an upper disk 2726 and a downwardly depending central shaft 2728. The upper disk 2726 is shaped and dimensioned to fit within the open upper edge 2722 of the outside collar 2720 such that it is frictionally retained therein. The central shaft 2728 is smaller and functions as a guide for suture 2718 wrapped thereabout.

The cap 2712 further includes opposed downwardly extending extension arms 2714, 2716. These arms 2714, 2716 provide for wrapping of the suture 2718 about the cap 2712 upon rotation of the cap 2712. Once the suture 2718 is wrapped about the cap 2712, the disk 2726 is fixed within the outside collar 2720, securing the suture 2718 in a "knotted" arrangement.

Although various mechanical knotting techniques are disclosed above, it is contemplated other fastening techniques may be used without departing from the spirit of the present invention. For example, and with reference to FIG. 63, fusing of the tied suture is preferably achieved by RF, ultrasonic, or electrocautery for melting of suture knot 2810 to improve knot holding capability. This method would allow for a normal endoscopic knot to be tied adjacent the cinched tissue area. But since it would have a tendency to untie, an energy source (cautery, ultrasonic, RF, or other heat source) would then be applied to the knot fusing the knot together.

The lacing pattern, the cinching method, and the anchoring means of the suture all contribute greatly to ease of use of the device. With this in mind, various suturing techniques have been developed. The present disclosure is meant to detail at least the preferred lacing method and an alternate anchoring method for cinching both ends simultaneously.

In accordance with the various lacing technique described below, the present method is achieved by providing a suture with a needle attached thereto. The suture includes a first lead and a second lead. The needle and suture are then inserted into an organ through a passageway. A single stitch is thrown through a first tissue member and a single stitch is thrown through an opposed and spaced apart second tissue member. The step of throwing stitches is repeated at least once and the first and second tissue members are brought into contact by tensioning the suture, whereby suture drag is minimized during the tensioning and even tissue compression substantially achieved. Finally, the suture is secured in positioned with the first and second tissue members in apposition.

Figure 52:
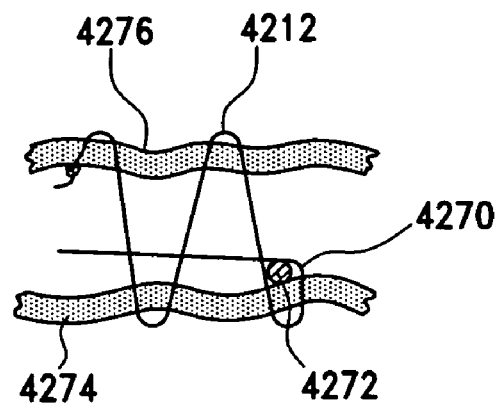

In accordance with a first embodiment shown in FIG. 52, resistance to cinching of a stitched suture 4212 is achieved via a throw reversing pin technique. The technique is initiated using traditional stitching techniques. That is, the needle and suture 4212 are inserted and alternating stitches are thrown along opposed tissue members 4274, 4276. The stitches are consistently thrown in the proximal to distal direction, that is, the stitch is initiated by inserting the needle through the tissue proximally to the point at which the needle stitch is completed by reentering the tissue. Although the terms distally and proximally are used in the present description, those skilled in the art will appreciate that these terms are relative and ultimately the specific direction of stitching may be reversed without departing from the spirit of the present invention.

However, the final throw 4270 of the suture 4212 (that is, the final loop or last stitch of the suture through the tissue) is altered to reduce friction during final cinching of the suture 4212. More particularly, and in accordance with a preferred embodiment of the present invention, drag and friction are reduced by positioning a reversing pin 4272 between the suture 4212 and the tissue wall 4274 after the last stitch 4270 is completed. This allows the suture 4212 to be cinched without it overlapping itself and twisting up. Such an arrangement will significantly reduce the friction necessary to overcome and cinch closed the lacing.

Figure 53:
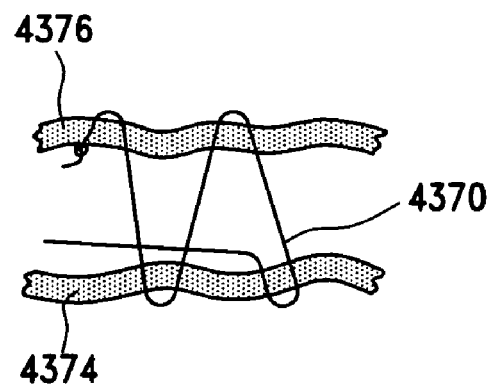

In accordance with another embodiment, and with reference to FIG. 53, resistance to cinching of a stitched suture 4312 is achieved via a throw reverse throw-over technique. The technique is initiated using traditional stitching techniques. That is, the needle and suture 4312 are inserted and alternating stitches are thrown along opposed tissue members 4374, 4376. The stitches are consistently thrown in the proximal to distal direction, that is, the stitch is initiated by inserting the needle through the tissue proximally to the point at which the needle stitch is completed by reentering the tissue. That is, the needle and suture 4312 are inserted and alternating stitches are thrown along opposed tissue members. The stitches are consistently thrown in the proximal to distal direction, that is, the stitch is initiated by inserting the needle through the tissue proximally to the point at which the needle is stitch is completed by reentering the tissue. However, the final throw 4370 of the suture 4312 is reversed to reduce friction during final cinching of the suture; that is, the final throw 4370 is completed by inserting the needle through the tissue in a direction distal to the point at which the needle stitch is completed by reentering the tissue.

More particularly, the final stitch 4370 is reversed in the direction in which it is thrown such that it is directed toward the position from which the surgeon will be pulling upon the suture line to cinch the suture 4312. This allows the suture to be cinched without it overlapping itself and twisting up. Such an arrangement will significantly reduce the friction necessary to overcome and cinch closed the lacing.

Figure 54:
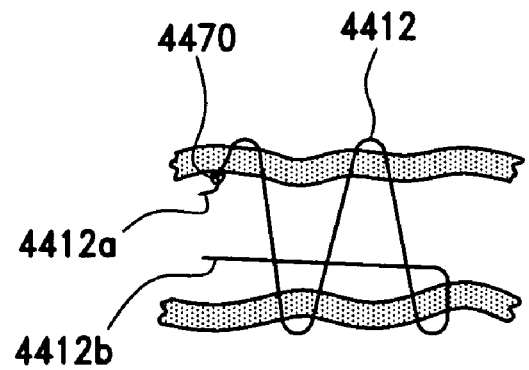
Figure 55:
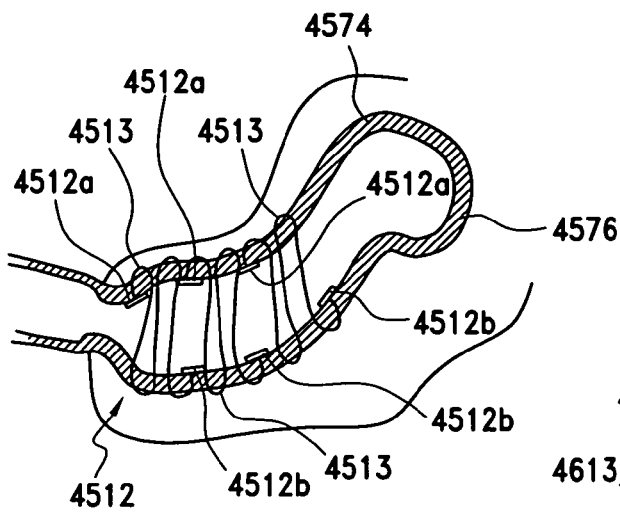

In accordance with an alternate embodiment, and with reference to FIG. 54, an initial locking loop 4470 is employed to enhance the ability of one to cinch the suture 4412 upon completion of the stitching. In particular, a first lead 4412a of the suture 4412 is anchored to the tissue along the first lead 4412a of the suture line rather than needing to have both ends accessed by the user throughout the procedure. More particularly, the first lead, or leading end, 4412a of the suture line is stitched and a portion thereof is anchored to the tissue. Thereafter the stitching is completed, with the final stitch 4470 and the second lead, or trailing end, 4412b of the suture line is accessed for cinching thereof. However, and in contrast to traditional cinching techniques, only the second lead 4412b of the suture line need be pulled to cinch the suture 4412. As shown in FIGS. 52 and 53, such an initial locking may be employed with other lacing techniques within the spirit of the present invention.

It is contemplated each set of sutures may be locally cinched before the next set is deployed from the suturing apparatus. This minimizes, but does not eliminate the need for the last stitch steps discussed above.

As shown in FIGS. 55 to 61, the preceding techniques for lacing opposed tissue members may be expanded in various ways. For example, and with reference to FIG. 55, the suture 4512 may be applied in separate segments 4513 with the first and second ends 4512a, 4512b of each segment 4513 anchored to respective first and second tissue members 4574, 4576. The first end 4512a of the suture 4512 is subsequently tensioned and tied off to cinch the suture. By using segments of stitches in this manner (and as discussed below in accordance with other embodiments), local cinching of each segment of stitches may be performed in a manner which may assist in improving the drawing of tissue together.

Figure 56:
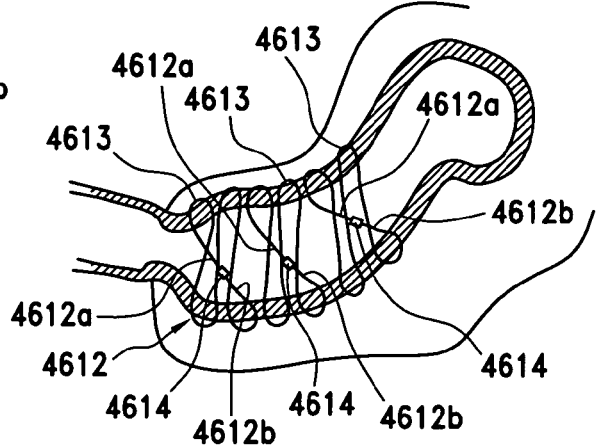

Referring to FIG. 56, the suture 4612 may be applied in separate segments 4613 with the first and second ends 4612a, 4612b of the suture 4612 coupled via a knotting element 4614. The first and second ends 4612a, 4612b are subsequently tensioned to cinch the suture 4612 and the knotting element 4614 and suture 4612 are fused to secure the suture in position.

Figure 57:
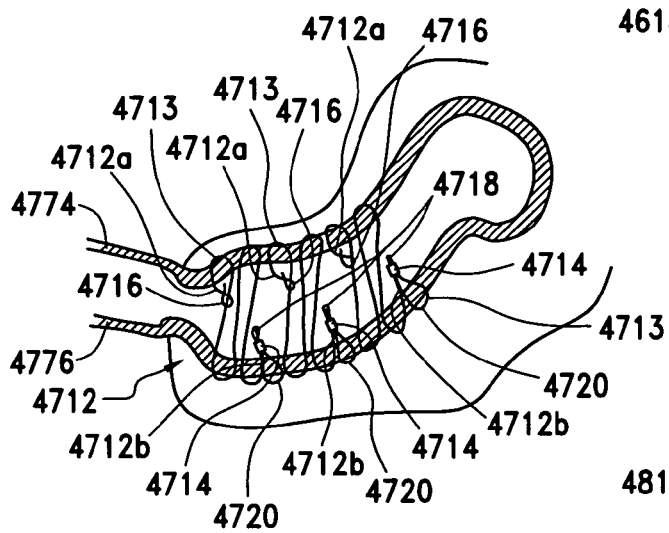

With reference to FIG. 57, the suture 4712 is once again applied in separate segments 4713. The first end 4712a of the suture 4712 is provided with a loop 4716 through which the remaining portion of the suture 4712 is passed to couple the first end 4712a of the suture 4712 to a first tissue member 4774. As to the second end 4712b of the suture 4712, it is secured via a knotting element 4714 as discussed above. More particularly, the second end 4712b is secured to the knotting element 4714 with a looping structure composed of a first loop 4718 which is coupled to the knotting element 4714 while a portion of the second end 4712b passes through the second tissue member 4776 to form a second loop 4720, the end of which is also coupled to the knotting element 4714. Thereafter, the second end 4712b may be tensioned, in particular, the first loop 4718 may be drawn through the knotting element 4714 and the knotting element 4714 and suture 4710 are fused to secure the suture 4710 in position.

Figure 58:
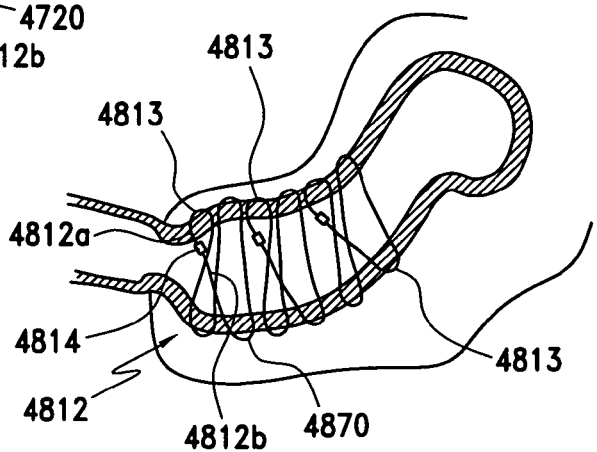

With reference to FIG. 58, the suture 4812 is applied in separate segments 4813 with the first and second ends 4812a, 4812b of the suture 4812 coupled via a knotting element 4814. However, the final throw 4870 of the suture 4812 is reversed as discussed above with regard to FIGS. 53 and 54.

The first and second ends 4812a, 4812b are subsequently tensioned to cinch the suture 4812 and the knotting element 4814 and suture 4812 are fused to secure the suture 4812 in position.

Referring to FIG. 59, the suture 4912 may be applied in separate segments 4913 with the first and second ends 4912a, 4912b of each segment 4913 anchored to respective first and second tissue members 4974, 4976. However, each throw of the suture 4912 is reversed as discussed above with regard to FIGS. 53 and 54, and extends in a distal to proximal direction as the suture is applied in the distal direction. The first end 4912a of the suture 4912 is subsequently tensioned and tied off to cinch the suture 4912. Referring to FIG. 60, the same lacing technique is applied with the exception it is not completed in segments.

As shown in FIG. 61, an overhand knot 5022 may be used to secure the second end 5012b of the suture 5012, while the first end 5012a of the suture 5012 is anchored to the tissue.

In accordance with the present invention, it is preferred to apply medical fluid/sealant for improving the suture lines ability to engage and retain the tissue. Particular, the suture line is subjected to substantial strain for a short period of time after its application while the tissue applies substantial tension in its attempt to retain to its original configuration. This generally lasts for 7-10 days after the surgery is completed, and it is during this time period in which potential suture breaks are more likely. With this in mind, and as the following embodiments disclose, an adhesive, sealant, or medical fluid delivery mechanism can be used in conjunction with the present suturing device to increase the short term strength of the stomach pouch by adhesively binding the opposed tissue. A method of deployment of sealants or other medical fluid changes the stiffness properties of the tissue to improve the suture strength of the gastroplasty by adhesively binding the opposed tissue.

As such, and in accordance with a preferred embodiment of the present invention shown in FIG. 69, adhesive 3210 is used to improve short term strength of the suture line 3213, that is, the line of tissue held together via the suture 3212. A fluid deploying mechanism is utilized to lay down a line of fluid sealant or adhesive 3210 along the suture line 3214 after the suture line 3214 is completed to improve holding strength of the line. Either a thin layer adhesive or a foaming (void filling) adhesive or sealant 3210 can be used in conjunction with the suture 3212.

In accordance with an alternate embodiment, and with reference to FIGS. 70, 71 and 72, the suture 3312 is a hollow tube suture with periodic perforations 3314 along its length. Once the suture line 3313 is finished, the suture 3312 would be pumped full of the sealant or adhesive 3314 allowing it to be distributed all along its length increasing both the effective diameter of the suture, minimizing suture migration as well as providing a complimentary adhesive bond of the tissue together in addition to the suture line 3313.

Referring to FIGS. 73 to 82, yet a further embodiment is disclosed. A liquid polymer extrusion 3350 is used to form a sleeve 3352 around the internal pouch 3353 formed in, for example, the stomach 3354. The entire inside of the small gastroplasy created pouch 3353 and some length of the intestines would be coated with the polymer/adhesive 3350. This not only improves the strength of the pouch suture line, it also potentially creates some form of malabsorption compliment to the procedure that improves weight loss.

More particularly, and with reference to the various figures, a suction and application device 3356 is first transorally inserted within the stomach 3354. A vacuum is then created drawing opposed tissue surfaces 3358, 3360 together as shown in FIGS. 73 and 74. Thereafter, the liquid polymer extrusion 3350 is applied to the opposed tissue surfaces 3358, 3360 while the vacuum continues to be applied in a manner keeping the walls 3358, 3360 of the stomach 3354 in apposition. Eventually, the liquid polymer extrusion 3350 will cure holding the apposed tissue walls 3358, 3360 in apposition. Thereafter, and with reference to FIGS. 79 and 80, the suction and application device 3356 in accordance with the present invention may be withdrawn and the internal profile of the stomach 3354 is reduced to a simple passageway extending therethrough with a substantial portion of the stomach closed off from food absorption. Although the process described above does not employ sutures, the pouch could certainly be formed with suturing of the opposed tissue with the subsequent application of adhesives as described above.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A surgical suturing apparatus, comprising:
a suture housing secured to a distal end of an elongated support structure;
a needle mounted within the suture housing for movement about an arcuate path, the suture housing including a track in which the needle is positioned for movement about a path under the control of a drive assembly;
the drive assembly is operably associated with the needle for controlling movement of the needle with a suture secured thereto about the arcuate path in a manner facilitating application of the suture to tissue; and
wherein the suture housing includes a first housing member and a second housing member, and the suture housing has an open position in which the first housing member is moved away from the second housing member, while the first housing member and the second housing member remain connected to the elongated support structure, exposing the track for removal of the needle and a closed position in which the first housing member and the second housing member are secured together closing the suture housing in a manner holding the needle within the track for operation of the suturing apparatus;
a release structure coupled to the first housing member and the second housing member for selectively permitting movement of the suture housing between the closed position and the open position, the release structure including a cable facilitating user actuation for release of the first housing member from the second housing member, the cable passing through the elongated support structure.

2. The suturing apparatus according to claim 1, wherein the drive assembly moves the needle about a continuous circular path.

3. The suturing apparatus according to claim 1, wherein the suture housing is shaped and dimensioned for insertion through a natural orifice of a patient.

4. The suturing apparatus according to claim 1, wherein the suture housing is shaped and dimensioned for passage through an orifice from approximately 3 mm to approximately 24 mm in diameter.

5. The suturing apparatus according to claim 1, wherein the suture housing is shaped and dimensioned for laparoscopic insertion through a trocar.

6. The suturing apparatus according to claim 5, wherein the suture housing is shaped and dimensioned for passage through an orifice from approximately 3 mm to approximately 18 mm in diameter.

7. The suturing apparatus according to claim 1, wherein the suture housing includes a first housing member and a second housing member, and the first housing member and the second housing member are selectively secured via the cable laced along the first and second housing members.

8. The suturing apparatus according to claim 1, wherein a hinge connects the first housing member and the second housing member at a proximal end of the respective first housing member and the second housing member.

9. The suturing apparatus according to claim 1, wherein the suture housing includes a convex housing outer profile which facilitates closing of the suture housing as it is withdrawn from the body of a patient.

10. The suturing apparatus according to claim 1, wherein a needle may be reloaded within the suture housing when in its open position.

11. The suturing apparatus according to claim 1, wherein the first housing member and the second housing member are biased to the open position.

12. A surgical suturing apparatus shaped and dimensioned for insertion through a natural orifice of a patient, comprising:
a suture housing secured to a distal end of an elongated support structure;
a needle mounted within the suture housing for movement about an arcuate path, the suture housing including a track in which the needle is positioned for movement about a path under the control of a drive assembly;
the drive assembly is operably associated with the needle for controlling movement of the needle with a suture secured thereto about the arcuate path in a manner facilitating application of the suture to tissue; and
wherein the suture housing includes a first housing member and a second housing member, and the suture housing has an open position in which the first housing member is moved away from the second housing member, while the first housing member and the second housing member remain connected to the elongated support structure, exposing the track for removal of the needle and a closed position in which the first housing member and the second housing member are secured together closing the suture housing in a manner holding the needle within the track for operation of the suturing apparatus;
a release structure coupled to the first housing member and the second housing member for selectively permitting movement of the suture housing between the closed position and the open position, the release structure including a cable facilitating user actuation for release of the first housing member from the second housing member, the cable passing through the elongated support structure.

13. The suturing apparatus according to claim 12, wherein the suture housing is shaped and dimensioned for passage through an orifice from approximately 3 mm to approximately 24 mm in diameter.

14. The suturing apparatus according to claim 12, wherein a resiliently biased hinge connects the first housing member and the second housing member at a proximal end of the respective first housing member and the second housing member.

15. The suturing apparatus according to claim 12, wherein the suture housing includes a convex housing outer profile which facilitates closing of the suture housing as it is withdrawn from the body of a patient.

16. A surgical suturing apparatus shaped and dimensioned for laparoscopic insertion through a trocar, comprising:
- a suture housing secured to a distal end of an elongated support structure;
- a needle mounted within the suture housing for movement about an arcuate path, the suture housing including a track in which the needle is positioned for movement about a path under the control of a drive assembly;
- the drive assembly is operably associated with the needle for controlling movement of the needle with a suture secured thereto about the arcuate path in a manner facilitating application of the suture to tissue; and
- wherein the suture housing includes a first housing member and a second housing member, and the suture housing has an open position in which the first housing member is moved away from the second housing member, while the first housing member and the second housing member remain connected to the elongated support structure, exposing the track for removal of the needle and a closed position in which the first housing member and the second housing member are secured together closing the suture housing in a manner holding the needle within the track for operation of the suturing apparatus;
- a release structure coupled to the first housing member and the second housing member for selectively permitting movement of the suture housing between the closed position and the open position, the release structure including a cable facilitating user actuation for release of the first housing member from the second housing member, the cable passing through the elongated support structure.

17. The suturing apparatus according to claim 16, wherein the suture housing is shaped and dimensioned for passage through an orifice from approximately 3 mm to approximately 18 mm in diameter.

18. The suturing apparatus according to claim 16, wherein a resilient hinge connects the first housing member and the second housing member at a proximal end of the respective first housing member and the second housing member.

* * * * *